US008883863B1

(12) United States Patent
King et al.

(10) Patent No.: US 8,883,863 B1
(45) Date of Patent: Nov. 11, 2014

(54) SAFETY OF PSUEDOEPHEDRINE DRUG PRODUCTS

(71) Applicant: Pisgah Laboratories, Inc., Pisgah Forest, NC (US)

(72) Inventors: Clifford Riley King, Hendersonville, NC (US); David William Bristol, Mills River, NC (US); Michael L. English, Pisgah Forest, NC (US)

(73) Assignee: Pisgah Laboratories, Inc., Pisgah Forest, NC (US)

( * ) Notice: Subject to any disclaimer, the term of this patent is extended or adjusted under 35 U.S.C. 154(b) by 112 days.

(21) Appl. No.: 13/723,323

(22) Filed: Dec. 21, 2012

Related U.S. Application Data

(63) Continuation-in-part of application No. 12/080,513, filed on Apr. 3, 2008.

(51) Int. Cl.
*A61K 47/00* (2006.01)
*A61K 31/55* (2006.01)
*A61K 31/5415* (2006.01)

(52) U.S. Cl.
CPC .............. *A61K 31/55* (2013.01); *A61K 31/5415* (2013.01)
USPC ........................................................ 514/784

(58) Field of Classification Search
CPC ...................................................... A61K 8/362
USPC ........................................................ 514/784
See application file for complete search history.

(56) References Cited

U.S. PATENT DOCUMENTS

| | | | |
|---|---|---|---|
| 1,461,407 A | 7/1923 | Trout | |
| 2,925,417 A | 2/1960 | Ekskager et al. | |
| 3,326,896 A | 6/1967 | Holstius et al. | |
| 3,502,661 A | 3/1970 | Kasubick et al. | |
| 3,733,410 A | 5/1973 | Asche et al. | |
| 4,283,408 A | 8/1981 | Harata et al. | |
| 5,120,850 A | 6/1992 | Bod et al. | |
| 5,128,477 A | 7/1992 | Bod et al. | |
| 5,225,205 A | 7/1993 | Orsolini | |
| 5,232,919 A | 8/1993 | Scgeffker et al. | |
| 5,271,946 A | 12/1993 | Hettche | |
| 5,439,688 A | 8/1995 | Orsolini et al. | |
| 5,445,832 A | 8/1995 | Orsolini et al. | |
| 5,736,541 A | 4/1998 | Bunnell et al. | |
| 5,776,885 A | 7/1998 | Orsolini et al. | |
| 6,251,895 B1 | 6/2001 | Larsen et al. | |
| 6,472,563 B1 | 10/2002 | Tanoury et al. | |
| 6,720,453 B2 | 4/2004 | Tanoury et al. | |
| 6,987,111 B2 | 1/2006 | Greco et al. | |
| 7,022,698 B2 | 4/2006 | Hamied et al. | |
| 2005/0079138 A1 | 4/2005 | Chickering et al. | |
| 2008/0085306 A1 | 4/2008 | Nangia et al. | |

FOREIGN PATENT DOCUMENTS

| | | |
|---|---|---|
| EP | 0137600 | 7/1984 |
| GB | 295656 | 11/1929 |

OTHER PUBLICATIONS

Hamlin, William E. et al.; Relationship Between in Vitro Dissolution Rates and Solubilities of Numerous Compounds Representative of Various Chemical Species, Mar. 31, 1965.

*Primary Examiner* — Paul Zarek
(74) *Attorney, Agent, or Firm* — Joseph T. Guy; Perkins Law Firm, LLC

(57) ABSTRACT

A pharmaceutical drug product with at least one drug substance capable of providing immediate release or modified release profiles. The drug substance is selected from an amorphous form with an active pharmaceutical ingredient and a first organic counterion wherein the amorphous form has a phase transition temperature of at least 100° C.; and a morphological form with the active pharmaceutical ingredient and a second organic counterion wherein the morphological form of the drug substance has a phase transition temperature of at least 100° C.

149 Claims, 52 Drawing Sheets

Figure 49. Clomipramine and Sibutramine 2:1 and 1:1 Pamoates Equilibrium Solubility at pH 1.00

SAFETY OF PSUEDOEPHEDRINE DRUG PRODUCTS

CROSS-REFERENCE TO RELATED APPLICATIONS

This application is a divisional application of pending U.S. patent application Ser. No. 11/928,592 filed Oct. 30, 2007 which is related to U.S. patent application Ser. No. 11/595,379 filed Nov. 20, 2006 now U.S. Pat. No. 7,718,649 issued May 18, 2010, U.S. patent application Ser. No. 11/843,890 filed Aug. 23, 2007 now U.S. Pat. No. 8,039,461 issued Oct. 18, 2011, abandoned U.S. patent application Ser. No. 11/805,225 filed May 22, 2007 and divisional applications thereof and U.S. patent application Ser. No. 11/973,252 filed Oct. 5, 2007.

BACKGROUND OF THE INVENTION

The present invention is related to improvements in drug substances, and particularly, in improved dissolution control and dissolution stability through manipulation of morphology.

Co-pending U.S. patent Ser. No. 11/595,379 filed Nov. 20, 2006 entitled "Physical States of a Pharmaceutical Drug Substance" discloses the synthesis, purification and use of imipramine pamoate, the disclosure of which is totally incorporated herein by reference. Co-pending U.S. patent application Ser. No. 11/843,890 filed Aug. 23, 2007 also entitled "Physical States of a Pharmaceutical Drug Substance" discloses the synthesis and isolation of an additional polymorphic form of imipramine pamoate. Co-pending U.S. patent application Ser. No. 11/805,225 filed May 22, 2007 entitled, "Salts of Physiologically Active and Psychoactive Alkaloids and Amines Simultaneously Exhibiting Bioavailability and Abuse Resistance", the disclosure of which is totally incorporated herein by reference, discloses methodology to employ controlled substances for their intended purpose while inhibiting the behavioral act of drug abuse. Co-pending U.S. patent application Ser. No 11/973,252 filed Oct. 5, 2007 entitled, "Improved Drug Safety With Intrinsic Markers" discloses a method for supplying beneficial controlled substances to the commercial market and to those in need of such materials while inhibiting the potential for illicit purposes, the disclosure of which is totally incorporated herein by reference.

The formulation of active pharmaceutical ingredients (APIs) into drug products exhibiting the desired safety, efficacy and release properties is often an arduous process. A pre-formulation investigation is employed to elucidate the physical behavior of the API, also known as the drug substance, to identify its contribution to the formulated dosage characteristics. This assessment provides the formulating practitioner with information necessary to develop a drug product by providing the basis for eliciting a preferred bioavailability response from the drug substance. In other words, the formulation must account for any desired properties not engineered into the drug substance to impart the desired properties by the selection of appropriate excipients or other methodologies. One aspect of the formulation activity is to identify how to decrease, augment or maintain the physical and chemical properties attributable to the drug substance so as to optimize the overall properties of the drug product. In addition, the formulator, with knowledge of the drug substance's physical (and chemical) properties can begin to address the delivery properties of the dosage presentation with respect to a designed pharmacokinetic (PK) and pharmacodynamic (PD) profile.

What is meant by a drug substance is a molecular entity or compound, also known as an active pharmaceutical ingredient (API) that exhibits biological activity for the purpose of providing human or animal medication to treat disease, pain or any medically diagnosed condition. It is possible for a drug substance to be used in combination with one or more different drug substances to ultimately impart a biological response in humans or animals. A drug substance is typically formulated with other, non-biologically active compounds to provide a means of predictable and quantitative dosage delivery, or perhaps to impart acceptable stability features to the drug product.

What is meant by a drug product is a formulation, mixture or admixture of the drug substance with combinations of excipients, processing aids, buffers and perhaps other inert ingredients that allow delivery of the drug substance by the selected dosage form and administration route to the patient. Various dosage forms include, for example, pills, tablets, capsules, solutions, suspensions, and transdermal patches to name a few. Various routes of administration may include oral, nasal, rectal, vaginal, inhalation or injection along with numerous others. Such routes of administration dosage form descriptions may be found in tablature format in the Red Book, Pharmacy's Fundamental Reference, 2005 Edition, published by Thomson on pages 177 and 178, respectively. The dosage is the actual concentration delivered to the patient, and depending upon many factors and the actual delivery system selected, the dosage may be available for essentially immediate release, release over time, or manipulated by additional means for stimulated release (for example, by irradiation).

For solid oral dose or suspension presentations, and where the drug substance is a solid, a polymorph evaluation must be performed on the API. For drug substances capable of existing in one or more polymorphic forms (and perhaps in an amorphous form), a polymorphic evaluation must be performed to determine the equilibrium solubility profile of each crystalline form and to identify the stability profile of each polymorph. One aspect of the stability profile is to demonstrate the selected polymorph retains its polymorphic characteristic as a function of time, temperature and humidity. If the selected polymorph represents a meta-stable state and upon exposure to time and temperature it converts to a different morphological form, the dosage presentation, i.e. the formulated product, may behave differently from its intended pharmaceutical application.

The United States Food and Drug Administration (FDA) has recognized the necessity to clearly define an API's polymorphic specifications when used in a drug product. In the FDA's Guidance for Industry, ANDAs: Pharmaceutical Solid Polymorphism, the impact of drug bioavailability and bioequivalence are discussed with respect to a drug substance's polymorphic behavior. References abound for the formulating practitioner that teach the advantages of the amorphous state of a drug product for providing enhanced solubility and dissolution rates versus the polymorphic (i.e. crystalline) states of the same compound. For example, in the "Handbook of Pharmaceutical Salts; Properties, Selection and Use" (Wiley-VCH, 2002, p. 49), the amorphous state of a drug substance leads to increased bioavailability compared to a polymorphic form. This behavior is attributed to enhanced solubility and dissolution rate. Similarly in "Polymorphism in Pharmaceutical Solids", (Marcel Dekker, 1999, p. 281), the polymorphs identified as having comparative less crystalline composition will exhibit higher solubility and dissolve more quickly than more stable polymorphs of the same compound. Polymorphic forms and their comparative aqueous solubility are also discussed in "Drug Bioavailability; Estimation of Solubility, Permeability, Absorption and Bioavailability", (Wiley-VCH, 2003, p. 218-19). "Drug Bioavailability" states that the highest-melting point polymorph (most stable) exhibits the least solubility, and as a rule, holds for solubility measurements performed at either room temperature or body temperature.

An important issue surrounding the current unprecedented activity in generic drug development is the evaluation of existing pharmaceutical products to identify their polymorphic behavior and to incorporate the correct polymorph (or one with associated bio-equivalence or defined behavior) into a generic commercial offering. Simultaneously, the generic product must exhibit a favorable impurity profile compared to the original, innovator product. Frequently for older drug products, the degree to which the active ingredient may be present in one or more polymorphic forms has not been explored or well characterized (if at all). Different polymorphic forms can radically influence a drug's release properties and result in a dramatically altered pharmacokinetic behavior for the patient.

To demonstrate the preceding assertion, U.S. Pat. No. 3,326,896 [Holstius] is illustrative, and the disclosure is totally incorporated herein by reference. The author discloses three embonic (pamoic acid) addition salts free from unpleasant taste and local anesthetic properties, and useful for the treatment of depression. The addition salt of 5-(3-dimethylaminopropyl)dihydro-5H-dibenz-[b,f]-azepine, (imipramine), was absorbed more slowly than the corresponding hydrochloride salt. Processes for making the embonic acid addition salts in aqueous and organic media were also disclosed. A review of the reported laboratory work reveals an anomalous observation in that the same "melting point" was reported for the pamoate salt of 5-(3-dimethylaminopropyl)-10,11-dihydro-5H-dibenz[b,f]azepine as for 5-(3-methylaminopropyl)-10,11-dihydro-5H-dibenz[b,f]azepine derivative. Both "melting points" were reported as 125-150° C. even though they are different compounds prepared under the same aqueous conditions. Melting ranges of this magnitude are generally associated with the presence of impurities and/or the presence of solvates/hydrates. In connection with the material the authors isolated, no crystalline forms were observed or claimed, and indeed, no attempt was made to characterize crystalline forms through techniques such as microscopy or X-ray powder diffraction patterns. Further, no calorimetry was performed thus clues gleaned from heats of fusion or heats of hydration were not provided. Interestingly, the author claims the embonic acid addition salt of 5-(3-dimethyl-aminopropyl)-10,11-dihydro-5H-dibenz[b,f] azepine, however the salt is not characterized as the 1:1 salt or as the 2:1 salt or some mixture thereof. Perhaps the broad melting point reported in the specification suggests the presence of impurities and/or the presence of unidentified solvates or hydrates.

In addition to the indefinite polymorphic issues associated with the API as described above in Holstius, the impact on the drug's in vivo (rat) behavior yielded a conclusion from the investigators that, "there is a slower rate of absorption of the embonate, but that at 8 hours, the levels attained with the embonate exceed those of the hydrochloride". It should also be noted here that an embonate is an alternative name for pamoate. Additionally, the investigators evaluated the embonates and analogous hydrochloride salts for toxicity ($LD_{50}$ comparison of intraperitoneal and peroral administration of each salt type). Here too a "surprising finding" of reduced acute toxicity was observed for the embonates compared with the hydrochlorides. The two findings appear to be in contradiction since the embonates ultimately reached levels exceeding those of the hydrochloride.

A number of drug substance and drug product development, manufacturing, pharmacological performance and stability features must be addressed to adequately commercialize a drug product. In the course of drug product development, a perplexing and paradoxical dilemma occurs when an API exhibits the ability to exist in different polymorphic forms and may through time, and/or temperature and humidity effects, convert to another crystalline form. It is well known that these changes in a defined polymorphic form can lead to significant differences in the physiological response the drug exhibits. At a minimum, the dissolution rates (in vitro or in vivo) are expected to change, and the release properties of the active ingredient from its crystalline matrix or from the formulated drug product are also likely to change. As dissolution, or in vivo solubility changes, the overall bio-availability of the active ingredient may also change. The consequence is that too many variables are introduced to fully or adequately evaluate the drug's beneficial properties.

To provide a step-wise presentation of the necessary activities occurring during drug product development, basic toxicity and pharmacological studies are implemented to evaluate the drug's potential safety and efficacy. Ideally, the drug substance's chemical stability is sufficient so as not to complicate the evaluation through non-metabolic impurity-generating degradation pathways. Equally important is that the drug substance exhibit physical stability throughout the final stages of its manufacture, formulation to a drug product, packaging, storage, distribution and use (e.g. clinical trial testing, etc.). For APIs which may exist in multiple polymorphic forms, this potential for physical (form) transformation has huge technical, medical and financial implications. It is estimated that only one in ten thousand drug candidates are ever commercialized with the vast majority of candidates having early failures (for toxicity, efficacy, safety, etc.). It is unclear if the high failure rate is the result of an improper assessment of the data, or a correct assessment of the results but under false assumptions. In other words, the compound and its formulation did not represent what was actually evaluated. Similarly, the literature contains numerous examples of approved drug products "drifting" to less than effective materials because of polymorphic issues arising and altering the bio-availability domain of the API.

This logic also extends into the actual manufacture of the drug substance. Early in drug substance process development, it may be unknown or poorly understood what process factors influence a drug substance's physical form. Further, little to no expenditure has been allocated to evaluate the substance's propensity for existing in multiple polymorphic forms (including amorphous material). Typically, the business goal is to prepare adequate quantities of API at reasonable purity and to quickly perform a screening evaluation for toxicity and therapeutic effect. The intention of these activities is to quickly ascertain if the intended drug is worthy of the significant financial expenditure to commercialize the product. With favorable toxicity results and a positive indication to expect reasonable therapeutic benefit, a more detailed technical investigation ensues. Again, the literature abounds with post-commercialization polymorphic issues arising and disrupting the expected benefit of a drug product. It is reasonable to conclude that an exhaustive investigation of potential physical forms of drug substances is typically absent from the drug substance development process. Indeed, an "exhaustive investigation" is not practical and inherently requires violating the philosophical principle of proving a negative condition. Simply stated, it is not possible to prove that an API has a fixed number of polymorphic or solvatomorphic forms under all circumstances and conditions.

The practical solution to the polymorphic possibilities associated with a drug substance is to establish stable process conditions which yield a singular and analytically defined physical form of the drug substance. This form is then subjected to challenging environments to which the API may be reasonably exposed during its manufacturing process and subsequent down-stream manipulations (i.e. formulation and tableting/(en)-capsulating, etc.). These tests also may include evaluating the chemical and physical stability of the drug substance. The drug substance is also likely to be tested under routine and accelerated stability storage conditions. Here, the API is packaged and subjected to 25° C./60% relative humidity and 40° C./75% relative humidity conditions. The formulated drug product is also packaged and stored under these conditions to determine its chemical and physical stability also. Accelerated storage stability testing typically occurs for at least three months, and routine stability testing, upon commercialization, may extend for multiple year periods. Obviously, investment in these activities is often restricted until the basic toxicity and therapeutic effect screening has been performed.

The findings from the challenge tests and the stability storage tests for the API can have a number of ramifications. First, the simplest conclusion is presented when the physical and chemical analysis of the API remains unchanged from the time-zero point. All other findings may have varying levels of consequences to the drug development program. To focus on the physical form, if the polymorphic purity changed beyond that attributable to chemical degradation, the resulting polymorphic form may no longer exhibit the therapeutic properties concluded from previous evaluations. The bio-availability of the drug substance is likely altered and few, if any, definitive conclusions can be drawn. This occurrence represents a lost investment, lost time and a return to nearly the beginning of the drug evaluation process.

Clearly, there remains a technical challenge for improving the drug development process to better assure definitive toxicity and therapeutic findings from drug substances capable of exhibiting polymorphism. One approach is to provide stable polymorphic materials early in the drug development process and thereby eliminate multiple inter-related factors in the drug evaluation process. If the various and essential physical and chemical properties (e.g. stable and predictable morphology) of a drug substance could be pre-determined, tailored or engineered to meet or augment the dissolution properties of the drug substance's corresponding mineral acid salt while improving upon the unpredictable features associated with the mineral acid or simple organic acid salts, significant commercial benefit would be realized. Similarly, by intentionally engineering performance features into the drug substance which have traditionally been imparted by formulation of the drug substance by the addition of excipients, the value of the drug substance is enhanced. In effect, the drug substance will also act as a drug delivery vehicle by assuming properties most often associated with formulation techniques, for example, modified release properties.

In an article by Mike Zaworotko, "Crystal Engineering of the Composition of API's: Understanding Polymorphs and Designing Pharmaceutical Co-Crystals", published in American Pharmaceutical Outsourcing, 5(4), 216, 2004, the author discusses the "growing field of crystal engineering" and its potential impact on "the formulation side of the pharmaceutical industry". Zaworotko relates polymorphism as a manifestation of supramolecular assemblies that are formed as a result of molecular components within a molecule having a predisposition to align into a greater aggregate. Different polymorphs can then arise from supramolecular isomerism. The article provides an overview analysis of two APIs (Indomethacin® and Tegretol®) possessing molecular constituents which act as supramolecular synthons and impact the polymorphs, solvates and co-crystals available to these compounds. The author identifies that the physical properties desired of an API are critically dependent upon the supramolecular chemistry and ultimately, that those physical properties of greatest importance in a formulated drug product can be obtained ("in principle") through crystal engineering of the API. Of particular relevance for which API crystal design could add value are on those APIs that exhibit poor solubility or permeability.

SUMMARY OF THE INVENTION

It is an object of the present invention to provide a selection guide for the formation of organic acid addition salts of amine containing drug substances for the purpose of engineering a desired dissolution profile. The selection guide offers organic acids containing at least one aromatic ring and substituted with a hydroxyl moiety and a carboxylic acid functionality wherein the substituents are in a 1,2 or ortho relationship to one another on the at least one aromatic ring.

It is a feature of the present invention to selectively prepare organic acid addition salts of amine-containing drug substances in polymorphic and amorphous forms. Similarly, preparation of these forms may be predetermined for a given stoichiometric ratio of 1:1 and/or 2:1 (amine containing drug substance:organic acid) dependent upon the number of ortho hydroxy carboxylic acid units contained within the organic acid component.

Yet another feature of the invention is to prepare polymorphic salts having phase transitions greater than 100° C., said polymorphic salts stable to exposure to heat and moisture, yet polymorphic forms exhibiting more rapid dissolution profiles than the amorphous form.

Another aspect of the invention is for the selection of an organic acid salt such that release of the drug substance can selectively occur in the stomach or in the intestine of a human or animal.

The present invention also provides an oral delivery mechanism for acid labile drug substances to the intestine without undergoing degradation processes in the acid environment of the stomach. In essence, the invention potentially obsoletes enteric coating processes for amine-containing drug substances.

An advantageous feature of the present invention is the preparation of a pharmaceutical drug substance wherein the polymorphic solid states available to the drug substance are engineered or tailored to simultaneously meet a predetermined dissolution profile, phase transition temperature, and morphological stability. The engineering steps include selection of an organic acid residue to be incorporated into the drug substance wherein the organic acid is selected from the group consisting of having at least one aromatic ring and substituted with at least one hydroxyl group and at least one carboxyl group wherein a hydroxyl and a carboxyl group are in an ortho relationship.

Yet another feature of the invention is to provide and/or to improve drug delivery mechanisms for the treatment of urinary incontinence and irritable bowel syndrome. The present invention may also be employed to deliver drug substances having anti-convulsant, anti-depressant, analgesic, anesthetic, anxiolytic, psychotropic, hallucinogenic, hypnotic, anorexic, cough remedy, cold remedy, sinus remedy, anti-neoplastic, anti-emetic, anti-biotic or adjuvant therapy.

It is a feature of the invention to obtain controlled release, extended release, immediate release, sustained release and targeted release of drug substances wherein the release property is imparted by the selection of the organic acid from which the organic acid addition salt of the amine containing drug substance is prepared.

These, and other embodiments as will be realized, are provided in a pharmaceutical drug product comprising at least one drug substance selected from the group consisting of: an amorphous form comprising an active pharmaceutical ingredient and a first organic counterion wherein the amorphous form has a phase transition temperature of at least 100° C.; and a morphological form comprising the active pharmaceutical ingredient and a second organic counterion wherein said morphological form of the drug substance has a phase transition temperature of at least 100° C.

Yet another embodiment is provided in a pharmaceutical drug product comprising: an amorphous drug substance comprising an active pharmaceutical ingredient and a first organic counterion wherein the amorphous drug substance has a phase transition temperature of at least 100° C.; and at least one of a morphological form of the drug substance comprising the active pharmaceutical ingredient and a second organic counterion wherein the morphological form of the drug substance has a phase transition temperature of at least 100° C.

Yet another embodiment is provided in a method of administering drug product to a patient comprising: providing the drug product to the patient as an oral dose wherein the drug product comprises a drug substance comprising an active pharmaceutical ingredient and an organic counterion; administering the oral dose to a patient wherein no more than 50%, by weight, of the active pharmaceutical ingredient releases in a stomach and at least 50%, by weight, of the active pharmaceutical ingredient releases in an intestine.

Yet another embodiment of the present invention is provided in a method of administering an active pharmaceutical to a patient comprising: providing a drug substance to the patient wherein the drug substance comprises the active pharmaceutical and an organic counterion in a ratio of 2:1 respectively; introducing the drug substance to a first drug absorption location of the patient wherein a portion of the active pharmaceutical in the drug substance is released from the drug substance yielding a dissolved active pharmaceutical and a modified drug substance comprising a second ratio of the active pharmaceutical to the organic counterion of less than 2:1; introducing the modified drug substance to a second drug absorption location of the patient wherein a remainder of the active pharmaceutical is dissolved yielding an absorbable active ingredient and a free organic counterion Yet another embodiment is provided in a pharmaceutical drug product comprising: 10-90 wt % of a first drug substance comprising a first active pharmaceutical ingredient and a first organic counterion in a stoichiometric ratio of 1:1; 10-90 wt % of a second drug substance comprising said active pharmaceutical ingredient and said first organic counterion in a second stoichiometric ratio of 2:1; and wherein said first organic counterion and said second organic counterion are independently defined by

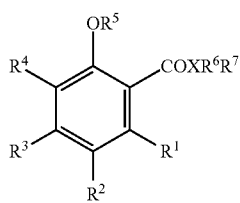

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6$+$R^7$ may represent an alkali earth cation, ammonium or together form a heterocyclic moiety.

Yet another embodiment is provided in a pharmaceutical drug product comprising: a first drug substance comprising a first active pharmaceutical ingredient and a first organic counterion wherein said first drug substance has a first release rate; and a second drug substance comprising a first active pharmaceutical ingredient and a second organic counterion wherein said second drug substance has a second release rate; and wherein said first organic counterion and said second organic counterion are independently defined by

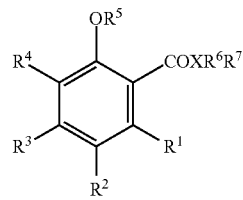

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6$+$R^7$ may represent an alkali earth cation, ammonium or together form a heterocyclic moiety.

Yet another embodiment is provided in a pharmaceutical drug product comprising: an amorphous drug substance comprising an active pharmaceutical ingredient and a organic counterion; and a morphological drug substance comprising said active pharmaceutical ingredient and said organic counterion; wherein said first organic counterion and said second organic counterion are independently defined by

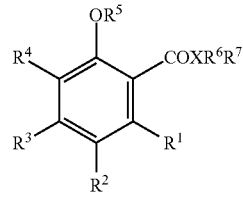

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6$+$R^7$ may represent an alkali earth cation, ammonium or together form a heterocyclic moiety, and said morphological drug substance has a faster dissolution rate than said amorphous drug substance.

DESCRIPTION OF INVENTION

Figure 1:
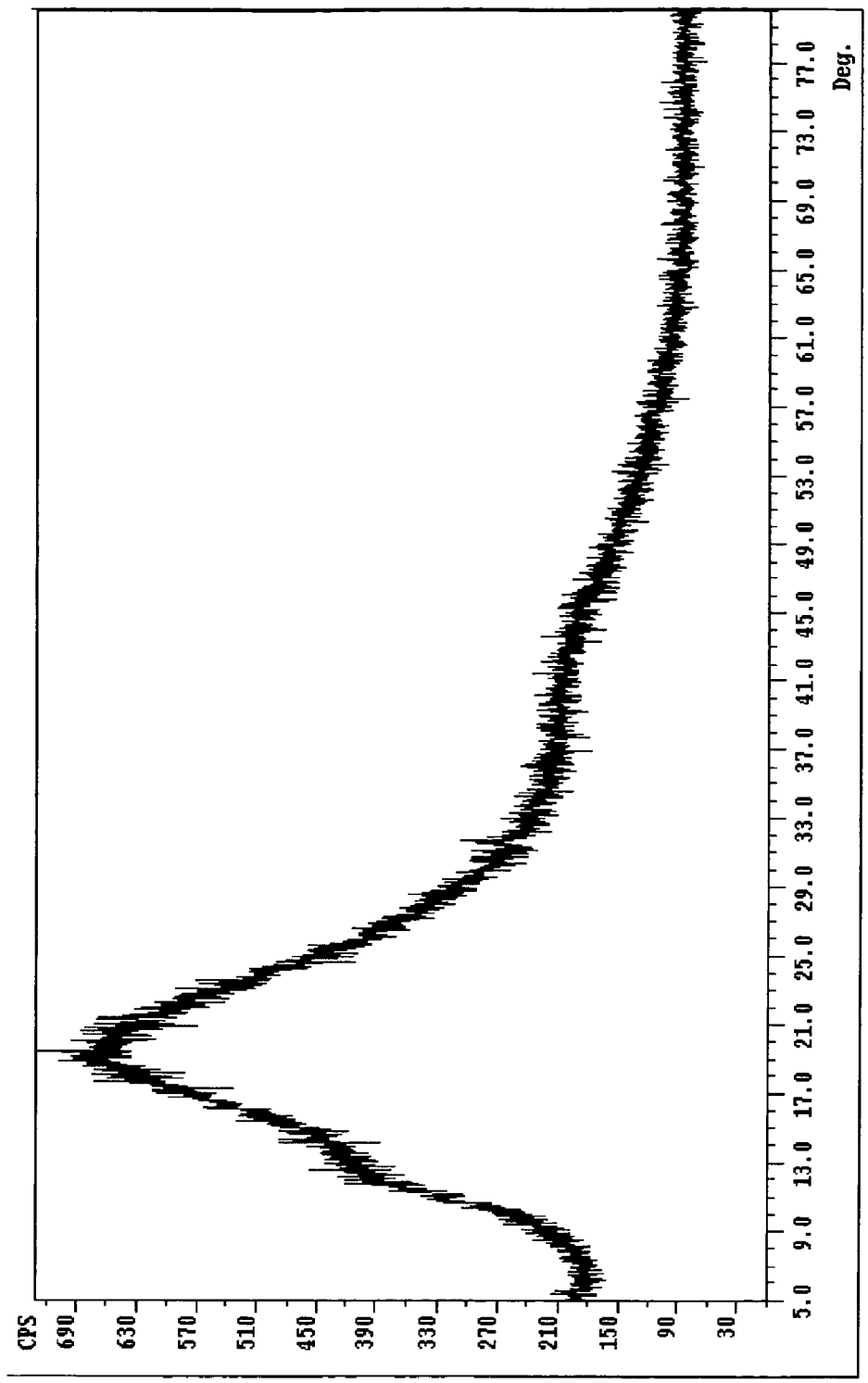
FIG. 1 is a PXRD diffractogram of sibutramine pamoate Form I.

The present invention is directed to novel drugs, and drug applications, wherein the dissolution rates are in direct conflict with the prior teachings in the art. The dissolution rate of certain amorphous salts is unexpectedly lower than specific morphologies thereby allowing for novel drugs, methods of administration and improved control over the location and rate of release of an active pharmaceutical ingredient.

Many drug substances contain amine functionality and indeed, it is a common practice to isolate the drug substance as its mineral acid salt. The mineral acid salts are typically very water soluble (although some are very poorly soluble, e.g. phenoxybenzamine HCl). The mineral acid salts often exhibit a propensity to be deliquescent or hygroscopic. This characteristic is detrimental to stable physical forms of a drug substance and hence complicate the drug development process. Methodologies eliminating the hygroscopic or deliquescent properties of an API would be beneficial.

Interestingly, and has been shown in commonly assigned patent application Ser. No. 11/843,890 filed Aug. 23, 2007 an annealing process can be employed to convert a polymorph exhibiting a phase transition at one temperature to a second polymorph exhibiting a phase transition at a higher temperature. These transitions were shown to occur at temperatures in excess of 100° C. Obviously, the energies of activation to convert one polymorph to the second polymorph are substantially above those typically available under normal laboratory or body temperatures (i.e. 37° C.). It has also been reported that the amorphous imipramine pamoate exhibits a phase transition above 100° C. and that it remains in its physical form without significant crystallization for an indefinite period under ambient conditions or conditions which mimic physiological conditions.

A number of polymorphic phase transitions were measured using DSC methodology for a host of amine-containing organic acid addition salts wherein the organic acid component comprises at least one aromatic ring substituted in an ortho relationship with a hydroxyl group and a carboxyl group. In all cases, these compounds exhibited phase transitions greater than 100° C. In the case of pamoate salts, amine to pamoate ratios of 1:1 or 2:1 (molar ratios), all provided amorphous or polymorphic phase transitions greater than 100° C. Additionally, the organic acid addition salts of amine containing APIs all exhibited hydrophobic properties and did not undergo significant physical change when simply exposed to moisture. Together, these characteristics of organic acid addition salts of amine-containing APIs provide stable polymorphs for drug evaluation. Older drugs (i.e. generics or those potentially becoming generic) are also susceptible to this strategy to improve their stability and delivery features. Most interestingly, it has been observed that the pamoate salts and similar organic acids exhibit varied dissolution profiles depending upon the organic acid component selected, the particular polymorph prepared and on the acid's stoichiometric relationship within the salt. Hence, the beneficial properties of polymorphic stability can be obtained while engineering the release properties required.

The findings of the invention described herein clearly indicate a negative teaching with respect to the solubility and dissolution rates of amorphous compounds and of their polymorphic analogs compared with the body of literature. Indeed, the literature indicates a priority focus has been placed on obtaining stable amorphous exemplars of drug substances as the preferred route to obtaining enhanced solubility and dissolution rates when employed in a drug product. In some respects a focus on obtaining amorphous drug substance is an over-simplification of the more complex issues. Most certainly, formulations require polymorphic stability of the drug substance and any morphological changes occurring during drug product (or substance) storage are undesired and can lead to unpredictable results in a drug's efficacy. Consequently, formulation activities include equilibrium solubility comparisons between morphological forms of a given drug substance.

In a surprising discovery it was determined that amorphous imipramine pamoate was less soluble and had a much slower dissolution rate than polymorphic forms of the same substance wherein the polymorphic forms were characterized as having a high degree of crystallinity. These findings provide for an alternative mechanistic approach away from traditional formulation methodologies. Further experimentation was conducted to determine the extent to which the dissolution profiles of organic acid polymorphic salts of amine containing drug substances varied as a function of organic acid selection, the polymorph(s) obtained and by the stoichiometric outcome of the salt. The findings indicate, without limiting the scope of the invention, immediate release, extended release, controlled release, sustained release and targeted release dosage formulations can be prepared by employing stable combinations of amorphous and polymorphic forms of the API. Further, the findings indicate that the delivery of a drug substance to its intended point of release can be engineered or manipulated by the selection of the drug substance as a particular organic acid salt. For example, an organic acid addition salt that exhibits poor dissolution under simulated stomach pH conditions can be delivered to the intestines without employing an enteric coating. Alternatively, amine containing drug substances exhibiting high rates of degradation under simulated stomach pH conditions can be protected as their organic acid addition salt wherein the drug substance is ultimately released in the intestine.

For the purposes described herein, on page 337 of Martin's Physical Pharmacy and Pharmaceutical Sciences, $5^{th}$ Ed., Patrick J. Sinko, (c) 2006, published by Lippincott Williams and Wilkins, the concepts of various drug release properties are defined. To add clarity to the discussion, these definitions are repeated in their entirety.

"Drug release is the process by which a drug leaves a drug product and is subjected to absorption, distribution, metabolism and excretion (ADME), eventually becoming available for pharmacologic action. Drug release is described in several ways. Immediate release refers to the instantaneous availability of drug for absorption or pharmacologic action. Immediate release drug products allow drugs to dissolve with no intention of delaying or prolonging dissolution or absorption of the drug. Modified release dosage forms include both delayed and extended release drug products. Delayed release is defined as the release of a drug at a time other than immediately following administration. Extended release products are formulated to make the drug available over an extended period after administration. Finally, controlled release includes extended release and pulsatile release products. Pulsatile release involves the release of finite amounts (or pulses) of drug at distinct time intervals that are programmed into the drug product."

In immediate release (IR), also referred to as immediately released and similar terms, approximately 85% of the therapeutic dose is released in less than 30 minutes.

Often release properties are controlled and attributable to specific formulation activities (e.g. enteric coating for passage through the stomach prior to dissolution). The behavior exhibited by the various polymorphic and amorphous forms of imipramine pamoate indicate release properties of the drug substance within a formulation could be dominated more by the selection of the polymorph/amorphous combination than by a specific formulation technique. It is not uncommon for instance to use a surfactant within the product formulation to alter the dissolution rate of the API. Surfactants such as sodium laurel sulfate and the like are used to accelerate the dissolution features of APIs exhibiting hydrophobic (i.e. lipophilic) characteristics.

As set forth herein the relative dissolution rate of specific morphologies, amorphous materials and salts with differing numbers of counterions is unexplained, and in many cases contrary, to the expectations in the art. These unexpected findings provide additional understanding to, and clarify the previously observed behavior of imipramine pamoate (i.e.

embonate of Holstius). Further, the experimental results indicate new and useful products can be formulated which primarily rely upon the polymorphic and amorphous properties of the API rather than on formulation methodologies to obtain a targeted delivery or dissolution profile.

Similarly, the unpredictable findings of Holstius, perhaps due to varying dissolution profiles of polymorphic species, have analogy to products evaluated for antischistosome and anthelmintic value. For instance, in "Burger's Medicinal Chemistry and Drug Discovery, Volume 4: Therapeutic Agents, $5^{th}$ Edition, edited by Manfred E. Wolff, A Wiley-Interscience Publication, copyrighted 1997 by John Wiley & Sons, pp. 384, 403-404, and 406-407, the pamoate salts tris (p-aminophenyl)carbonium (TAC) pamoate, pyrantel pamoate, and pyrvinium pamoate, respectively are discussed. The pamoate of TAC was developed to overcome the emesis and gastritis observed in dogs as compared with the more soluble chloride salt. Since the drug as its pamoate was found effective, it had to reach the dog's intestine to exert its anticholinesterase inhibition in the nervous system of the intestinal worms. In contrast, the chloride salt was likely released in the stomach where it was ineffective and led to undesirable side effects. Similarly, the therapeutic effects of pyrantel pamoate, described in Burger as the very insoluble pamoate salt, are attributable to the drug substance reaching the intestine wherein it was very effective against gastrointestinal nematodes. Pyrvinium pamoate was noted for its nearly insoluble nature and is not absorbed from the gastrointestinal tract. In fact the cyanine dye is known for its post-treatment stool-staining propensity. As with the TAC chloride, pyrantel chloride is more soluble and has "marked nauseating properties". Interestingly, no stoichiometric correlation was made between these drug products and their observed dissolution profiles or point of action. TAC and pyrantel pamoates are isolated as their 1:1 salts wherein one potential salt forming site on the pamoate moiety remains unoccupied. In contrast, pyrvinium pamoate is described as its 2:1 salt.

From the FDA's Guidance for Industry, Waiver of In Vivo Bioavailability and Bioequivalence Studies for Immediate-Release Solid Oral Dosage Forms Based on a Biopharmaceutics Classification System and the Biopharmaceutics Classification System (BCS) Guidance, a framework is provided for classifying drug substances based on aqueous solubility and intestinal permeability. Further, in conjunction with dissolution testing, the rate and extent of drug absorption from an IR solid oral dosage form can be predicted. The classification system has four categories as indicated:
Class 1: High Solubility/High Permeability
Class 2: Low Solubility/High Permeability
Class 3: High Solubility/Low Permeability
Class 4: Low Solubility/Low Permeability It is reported in an article by Cynthia K. Brown, et al. entitled "Acceptable Analytical Practices for Dissolution Testing of Poorly Soluble Compounds" published in Pharmaceutical Technology, December 2004, that for Class 2 compounds the rate of drug solubilization is much lower than the rate of drug absorption and consequently, in vitro—in vivo relationship or correlations may be possible to establish. In vitro—in vivo correlation is defined on page 338 in Martin's Physical Pharmacy and Pharmaceutical Sciences $5^{th}$ Ed; by Patrick J. Sinko,©2006 and published by Lippincott Williams and Wilkins, as: "A predictive mathematical model describing the relationship between an in vitro property of an oral dosage form (usually the rate or extent of drug dissolution or release) and a relevant in vivo response (e.g. plasma drug concentration or amount of drug absorbed)." In vitro—in vivo relationships may have a more qualitative character. For Class 4 compounds, Brown recognized that these compounds are likely to have solubility and permeability limited absorption.

"Poor Aqueous Solubility—An Industry Wide Problem in Drug Discovery", by Christopher Lipinski, published in the Fall 2002 edition, p. 82 of the American Pharmaceutical Review, the author discusses the chemical structural factors and physicochemical properties which portends the likelihood of poor absorption or permeation. These factors have become known as "Lipinski's Rule of 5" (but which really only contains four rules) and can be stated simply as
 1) More than 5-Hydrogen bond donors
 2) The molecular weight is over 500
 3) The Log P is over 5, and
 4) The sum of N's and O's is over 10.

The author then contrasts solubility and permeability of drug substances with respect to organization approaches to rational drug design. In general, Merck has tended toward improving the solubility of drug substances by improving the hydrogen bond interactions between the drug and water. Pfizer, by comparision, has tended to improve the lipophilicity of the drug substance to improve permeation. Either approach has limitations since improved lipohilicity will reduce water solubility and hence the drugs' availability for permeation. The other approach, improved solubility, may limit a drug's ability to pass the gastrointestinal wall. Each approach has implications during the clinical stage of drug evaluation and particularly may influence results obtained from fed or fasting patients.

In the January/February 2007, Volume 10, Issue 2 of the American Pharmaceutical Review, Julius F. Remenar provided an article entitled "Improving Oral Bioavailability Through Inhibition of Crystallization After Dosing". The author reports of the disastrous commercial consequences of a drug substance undergoing a marked decrease in bioavailability due to the drug substance crystallizing to an unacceptable solubility (different polymorph) after ingestion of the drug product. In particular, in vitro dissolution testing of several formulations allowed detection of amorphous and crystalline materials being observed depending upon the presence of formulation diluents. The author concludes that the meta-stable amorphous form is available for absorption; whereas inhibiting crystallization of the least soluble form (by diluents) provides the best overall absorption of the drug substance.

It is appropriate to apply the preceding categorizations and observations to the present invention. In connection with the BCS, the accepted teaching is for amorphous materials to be more soluble than their polymorphic relatives. Further, pamoate salts of active pharmaceutical ingredients were prepared having low solubility but exhibited reasonable permeability. For instance, imipramine pamoate was prepared at dosage levels corresponding to commercial products containing imipramine hydrochloride wherein the actual amount of amine-containing API in the dosage presentation is identical. Another set of approved FDA drug products, hydroxyzine pamoate and hydroxyzine hydrochloride, deliver equivalent amounts of the active ingredient within the dosage form (tablet). The FDA's market approval process requires the dosage forms to exhibit this type of equivalency or to indicate why there is a difference and for what purpose. Consequently, these compounds and others are subject to the BCS Class 2 hypothesis wherein an in vitro/in vivo relationship or correlation could be established.

In addition, the present invention is in conflict with the literature teachings and perhaps explains the very few FDA approved pamoate salt drugs (FDA's Orange Book presently lists only three). Conclusive observations indicated the amorphous form was less soluble under equilibrium dissolution conditions at pH 1 than the polymorphic forms. Explanation of this observed behavior (and the medicinal action of pyrantel, pyrvinium and TAC pamoates) is well beyond the standardized Lipinski rules. The in vivo (re)-crystallization process may be operative in some pamoate salts however, this possibility can be effectively evaluated by in vitro dissolution testing and analysis of the graphical presentation of the results. By way of example, an amorphous form subject to dissolution testing may crystallize and its dissolution profile altered to that resembling one or more of its comparable polymorphic forms.

While the above described pamoate salts were developed to overcome undesired side effects associated with conventional salts, there does not appear to be evidence indicating the release properties associated with a given stoichiometric ratio and polymorph analysis of a pamoate salt were investigated or even considered. Clearly, there remains a need in the practice of drug substance and drug product development to establish the operative mechanisms governing the dissolution profiles of pamoate salts and of the related families of organic acid addition salts.

Formulation methodologies abound for the preparation of drug products exhibiting various release properties. Few, if any, of these technologies rely upon the release property being designed into the API beyond recognition of the influence particle size and a given polymorph may have on the rates of release. The invention described herein provides a mechanism to impart the desired release property into drug products through the pharmaceutical drug substance by selecting an organic acid addition salt of an amine containing drug substance under pre-determined selection criteria expected for polymorphic and dissolution behavior. The anticipated release properties are primarily attributable to the organic acid component of the formed salt.

Alone, the stability features of the various polymorphs are a valuable commercial finding; however, the ability to blend amorphous and polymorphic forms has additional commercial benefit. As will be seen from the results of the dissolution studies, a blend of amorphous and polymorphic forms yields a dissolution profile resembling the results one would expect to obtain by measuring the concentration of a drug substance in the blood plasma generated from a sustained release product. To describe such a generalized profile, the drug substance is released and essentially (immediately) yields a spike in the blood plasma. This maximum concentration ($C_{max}$) diminishes but plateaus for an extended period sufficient that the concentration plateau remains within the range required for therapeutic efficacy for an anticipated duration based on dosing studies. As the blood plasma concentration decreases to where a therapeutic effect is compromised, a second dose may be administered. The present invention provides such a profile by the blending, in a predetermined ratio, appropriate amounts of the amorphous and polymorphic forms of imipramine pamoate to yield a sustained release product. By definitions employed herein, such an imipramine pamoate blend would yield a controlled release, targeted release, extended release and sustained release product. The blend is a controlled release product due to the effect of gastric fluid triggering the precipitation of the organic acid portion from which the drug substance is liberated. The blend exhibits targeted release, as expected, in the gastric environments. The extended release and sustained release properties result from the particular blend of imipramine pamoates to yield a $C_{max}$ and plateau concentration within the desired therapeutic efficacy.

Imipramine pamoate is characterized in various forms listed as Form I through Form VII in U.S. patent application Ser. Nos. 11/595,371 and 11/843,890. The same nomenclature is utilized herein.

Figure 39:
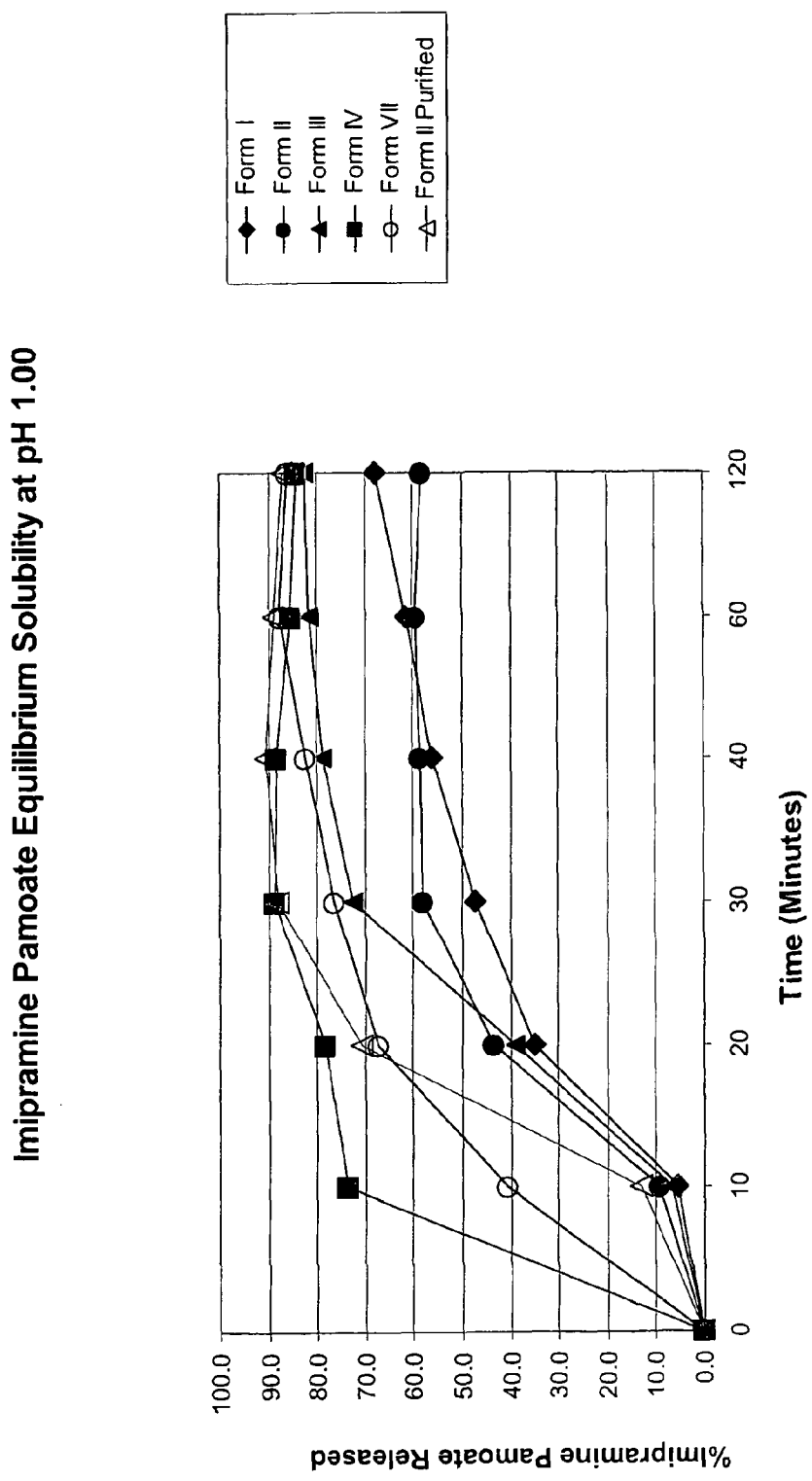
FIG. 39 is a graphical representation of the equilibrium solubility at pH 1.00 of imipramine pamoate morphological forms.
Figure 40:
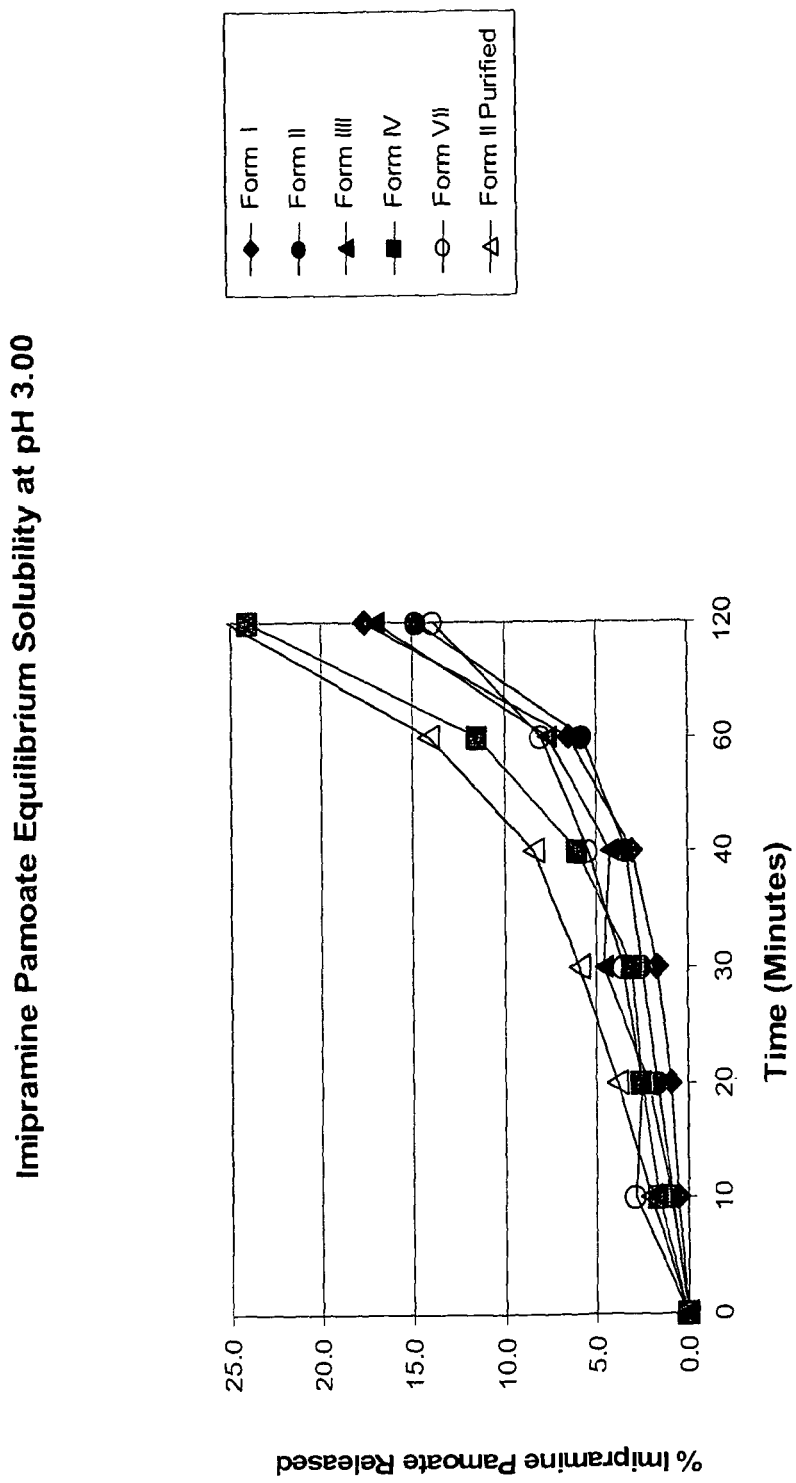
FIG. 40 is a graphical representation of the equilibrium solubility at pH 3.00 of imipramine pamoate morphological forms.
Figure 41:
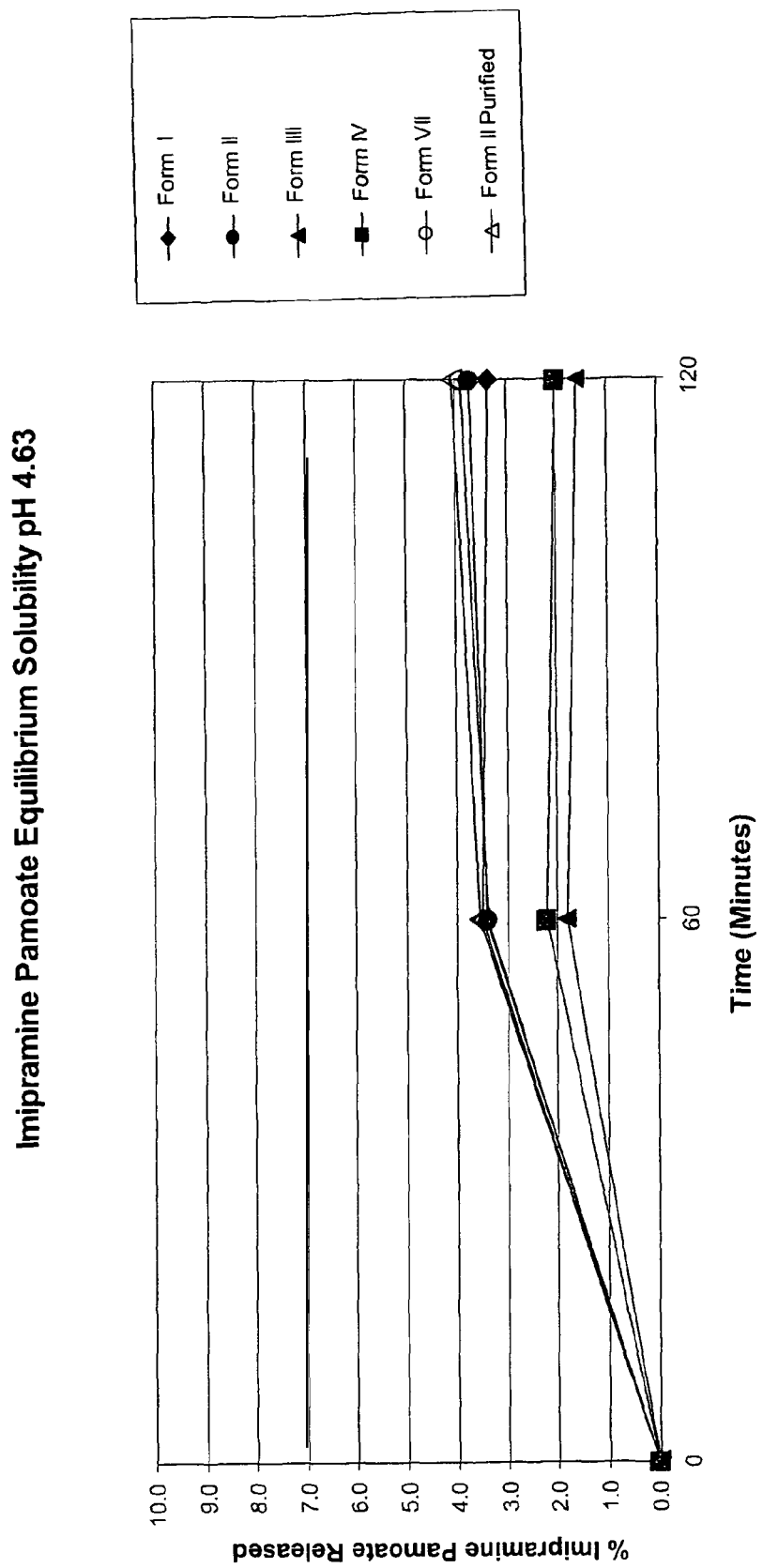
FIG. 41 is a graphical representation of the equilibrium solubility at pH 4.63 of imipramine pamoate morphological forms.
Figure 42:
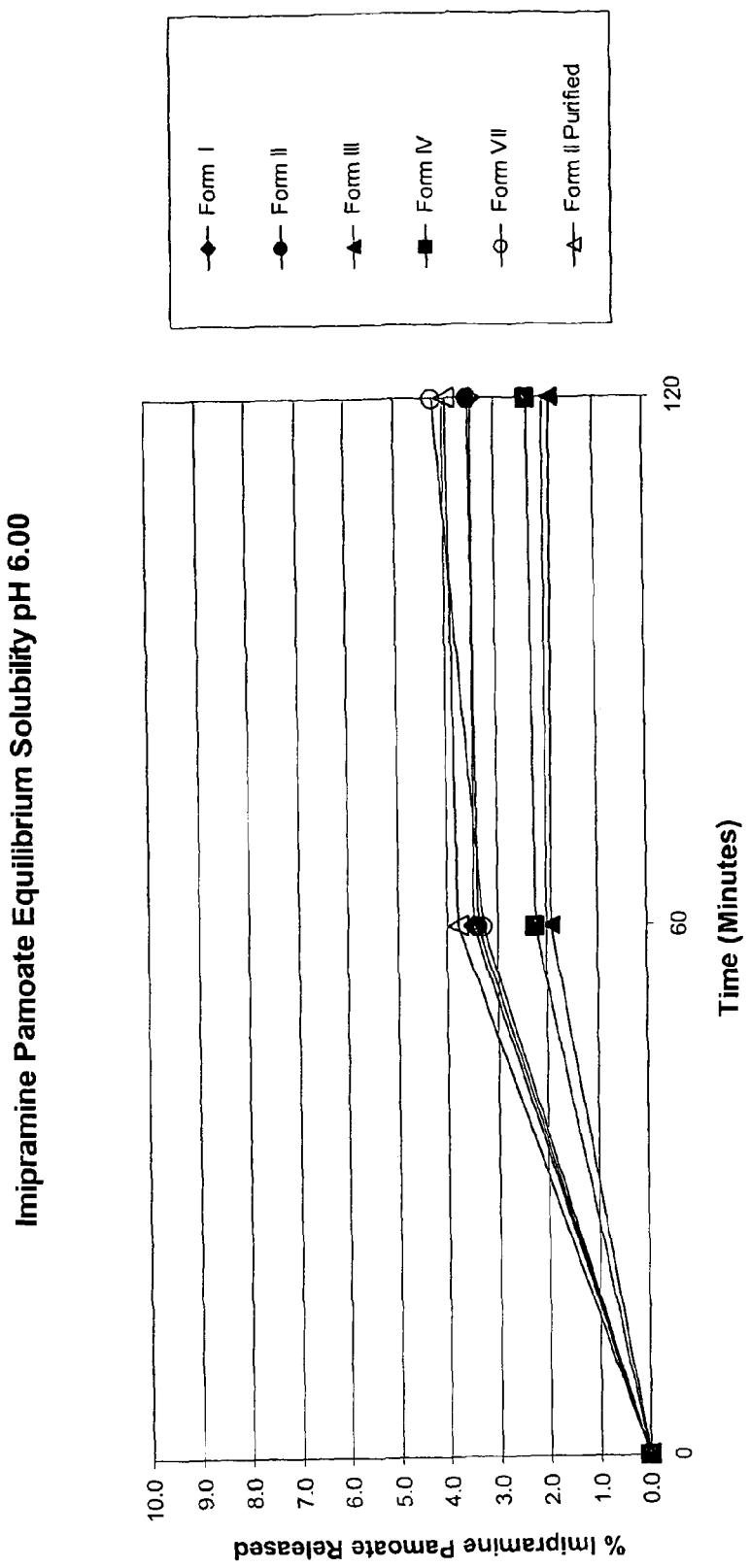
FIG. 42 is a graphical representation of the equilibrium solubility at pH 6.00 of imipramine pamoate morphological forms.
Figure 43:
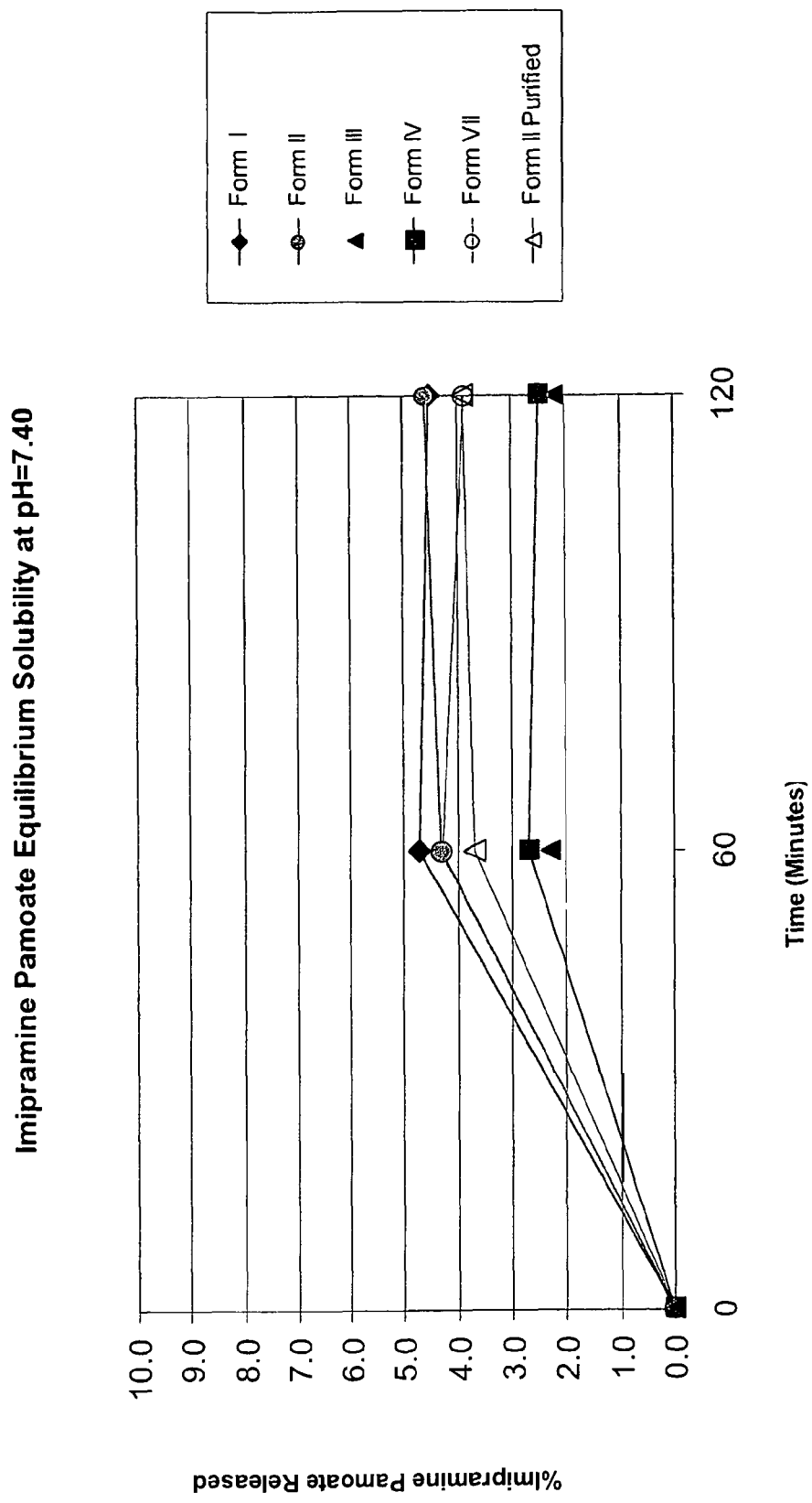
FIG. 43 is a graphical representation of the equilibrium solubility at pH 7.40 of imipramine pamoate morphological forms.

Contrary to the anticipated observation, amorphous imipramine pamoate (Form I) exhibited slow release properties under acidic conditions in a dissolution test procedure. Likewise, the most stable polymorph (defined as that polymorph having the highest phase transition temperature), exhibited essentially immediate release properties under the same test conditions. This trend continued with two additional forms (Forms II and III). From the graphed dissolution profiles (concentration as a function of time, FIG. 39), Forms I and II behaved very differently and unexpectedly as compared to Forms III and IV. Forms I and II exhibited somewhat linear release characteristic over the course of the test procedure whereas Forms III and IV exhibited unexpectedly quick release rates.

To elaborate on the testing details, the dissolution procedure was executed on each polymorphic form individually and under identical conditions. The specific procedure is designed to evaluate the equilibrium solubility of each form by providing sufficient concentration of the API in a defined volume such that an equilibrium concentration of API is obtained, i.e. the maximum concentration attainable from dissolution of that particular polymorph over an extended period was identified. For Forms I and II, equilibrium concentrations were not observed in the time frame allowed for test comparisons and the results are therefore indicative of slow release behavior from these polymorphic forms. The data for all forms, Forms I-IV and VII, are plotted as a percent weight/weight of the analyte released.

The results obtained from dissolution testing of each individual polymorphic form and of the amorphous material presented an interesting opportunity for achieving sustained release formulations uniquely dependent upon the polymorphic form of the API and not on formulation techniques. A blend of polymorphic (and amorphous) forms in a predetermined ratio was envisioned to provide an immediate release response attributable to the polymorphic form, while the slow release amorphous form would develop as a function of time under simulated gastric conditions. Consequently, this hypothesis was tested by performing the dissolution testing (equilibrium solubility method) by subjecting a blend of Form II and IV to the procedure outlined above. Indeed, the experimental findings supported the conceived additive results hypothesized and the dissolution tests indicated a sustained release formulation of imipramine pamoate could be achieved by the polymorphic blend described. It is important to recognize this achievement was enabled by the original finding that dissolution performance of the amorphous material was in contrast to the scientific teaching and the expected behavior of amorphous compounds.

It is interesting to note that the phase transition temperatures of amorphous imipramine pamoate and of its polymorphs are greater than 100° C. This observation indicates that stable polymorphic blends of imipramine pamoate could be achieved. It was further hypothesized that the conformational rigidity available through the chelation characteristic of the pamoate moiety may lead to similar findings with other drug substances. Consequently, a number of pamoate salts were prepared including sibutramine pamoate, clomipramine pamoate, and nortriptyline pamoate in amorphous and at least one polymorphic form. These drug substances were subjected to the identical dissolution tests as were the imipramine pamoate materials. With these compounds, additional unexpected results were obtained which confirmed the hypothesis that pamoate salts provided a dissolution profile and mechanism contrary to the accepted teachings. In general, these pamoates yielded dissolution profiles wherein the amorphous material had a slower release rate than the polymorphic forms.

For the purposes of the present invention a stable polymorph, also referred to as a thermodynamically stable polymorph is one which satisfies the spirit and intent of the US Food and Drug Administration in their Guidance for Industry, ANDAs: Pharmaceutical Solid Polymorphism; Chemistry, Manufacturing and Controls Information dated July 2007. This cited document outlines the impact API polymorphism may have on providing safe and efficacious medications into commerce. Indeed, predictable API polymorphic stability (as bulk API or in finished dosage form), is a requisite to obtaining reproducible in vivo dissolution and absorption profiles. In vitro dissolution testing is routinely used to evaluate the API and associated product manufacturing robustness to assure the API has not undergone a polymorphic conversion which may lead to a modified (and potentially undesired or ineffective) in vivo dissolution and absorption. Generally, the most thermodynamically stable polymorph is that crystalline form of a compound having the highest melting point. Within the context of the present invention, this view of stability can be expanded to include amorphous and morphological forms of a compound having, a) phase transition temperatures greater than 100° C.; and b) resistance to morphological conversion due to the presence of excipients, processing aids, adventitious moisture, and the like. Such amorphous and morphological forms are considered stable wherein morphological conversion due to manufacturing processes, inventory, storage and logistical operations (shipping), temperature excursions and actual product administration to a human or animal does not promote conversion. The observed phase transition temperatures of API product families herein are each above 100° C. and well above normal body temperatures (37° C.) or routine temperatures encountered during storage and transport.

Clearly, the unprecedented results appear to be attributable to properties associated with the specific counterions defined herein, particularly the pamoate moiety. Experiments were performed to elucidate and quantify the performance and observed morphological features the sub-structure provides when the specific counterion described herein is reacted to form an organic acid addition salt with an amine-containing drug substance. In the interests of providing methodology to tailor or engineer the multitude of physical and chemical features required of a commercially successful drug substance (and product), identification of the attributes imparted by the counterion would allow the selection of additional organic acids for the design engineering of pharmaceutical substances.

To further investigate the findings observed with pamoate, the dissolution profiles for related drug substances containing the xinafoate and salicylate moieties were obtained. Additionally, dissolution profiles were obtained on pamoate-containing drug substances wherein the stoichiometry was 1:1 (amine:organic acid). It was an unexpected finding that the dissolution profiles for various organic acid salts of amine containing drug substances yielded a dissolution distribution which upon analysis exhibited a consistency in behavior. Indeed, for a given amine-containing drug substance, a predictive dissolution profile model was now available depending upon the organic acid selected in which to form the drug substance's salt.

Historically the selection of an organic acid counter-ion for an amine-containing drug substance has taken a "hit or miss" approach to obtaining desired performance characteristics. The unexpected results from the imipramine pamoate dissolution studies provided a potential gateway for a design engineering approach to obtaining drug substances with enhanced features due to the synergistic effect of the organic acid and the amine-containing drug substance (as its free base) forming an organic acid addition salt.

The organic acid, also referred to herein as the counterion, is defined by the following Structures A through G wherein Structure A represents the general family embodied within the invention. Structure B represents the subset of salicylic acid and its derivatives conceived as a component of this invention. Structures C, D and E are regio-isomeric variations on Compound A wherein two adjacent substituents on Compound A form a fused aryl ring (i.e. $R^1+R^2$; $R^2+R^3$; and $R^3+R^4$). Structures F and G represent a further sub-category of dimer-like compounds derived from Structure A. In Structure F, dimerization has occurred through $R^4$ of two Structure A compounds with both possessing fused-aryl ring systems formed via $R^2+R^3$. In Structure G, dimerization has again occurred through $R^4$ of two Structure A compounds however both Structure A residues possess fused-aryl ring systems formed via $R^1+R^2$.

Structure A

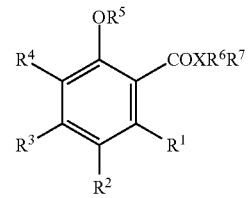

wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6+R^7$ may represent an alkali earth cation, ammonium or together form a heterocyclic moiety.

Particularly preferred organic acids include Structures B through E.

Structure B

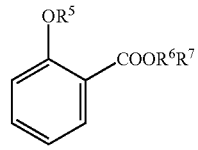

wherein $R^5$, $R^6$ and $R^7$ remain as defined above for Structure A;

Structure C

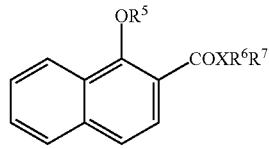

wherein X, $R^5$, $R^6$ and $R^7$ remain as defined above for Structure A and more preferably X is O;

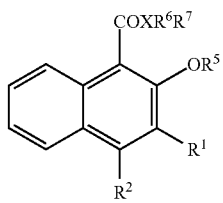

Structure D wherein X, $R^1$, $R^2$, $R^5$, $R^6$ and $R^7$ remain as defined above for Structure A and more preferably X is O; $R^1$ and $R^2$ are hydrogen;

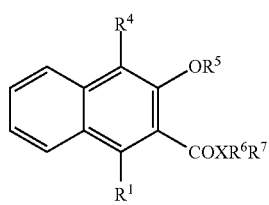

Structure E wherein X, $R^1$, $R^4$, $R^5$, $R^6$ and $R^7$ remain as defined above for Structure A and more preferably X is O, $R^1$ and $R^4$ are hydrogen;

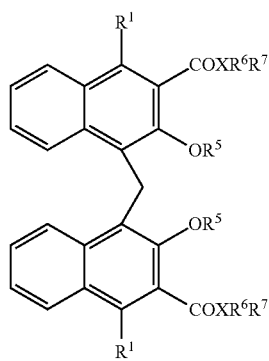

Structure F wherein X, $R^1$, $R^5$, $R^6$ and $R^7$ are independently defined as above for Structure A and more preferably at least one X is O and at least one $R^1$ is hydrogen; and

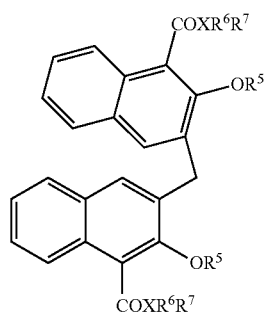

Structure G wherein X, $R^5$, $R^6$ and $R^7$ are independently defined as above for Structure A and more preferably X is O and $R^5$ is hydrogen.

Pamoic acid, or a synthetic equivalent of pamoic acid, is the preferred embodiment. Pamoic acid has a formula corresponding to Structure F wherein X is O; $R^5$, $R^6$ and $R^7$ are hydrogen.

A synthetic equivalent of pamoic acid is a material that provides the structural moiety independent of its particular salt, ester, or amide form and that upon pH adjustment yields pamoate functionality suitable for reaction, optionally with one or two equivalents of an amine-containing active pharmaceutical ingredient to form a pamoate salt. Examples of synthetic equivalents of pamoic acid capable of manipulation to produce pamoate salts include but are not limited to, disodium pamoate, di-ammonium pamoate, di-potassium pamoate, lower molecular weight di-alkyl and/or di-aryl amine pamoate, lower molecular weight di-alkyl and/or di-aryl esters of pamoic acid, and lower molecular weight di-alkylacyl and/or di-arylacyl O-esters of pamoic acid, i.e. those alkylacyl and arylacyl esters formed using the hydroxyl moiety of pamoic acid and not the carboxylic acid functional group. The descriptor phrase "lower molecular weight" used above means the indicated moiety has a molecular mass contribution within the pamoate derivative of less than about 200 amu.

For clarity, the use of lower molecular weight di-alkyl or di-aryl amine pamoate allows for the exchange of higher molecular weight amines, or drug free bases, to be exchanged for the lower molecular weight amine component during the salt formation reaction. Similarly, the use of lower molecular weight di-alkylacyl and/or di-arylacyl pamoates allow for their conversion through ester hydrolysis to the pamoic/pamoate moiety followed by reaction with the desired drug free base.

By analogy, beta-oxy-naphthoic acid (BON acid, 2,3-hydroxy naphthoic acid) and its isomers (1,2, and 2,1-hydroxyl naphthoic acid) are well suited for chelation and providing an intermediate step to conformational rigidity between salicylate and pamoate-like moieties. By employing a salicylate, naphthoate or pamoate and/or their related derivatives, a flexible toolbox is available to engineer the desired physicochemical properties of morphological stability and selective dissolution of drug substances. An important comparison supporting the current invention is the performance functionality of other organic acids compared to those disclosed herein. The organic acids that do not possess the synergistic duality of chelating ability and a conformational rigidity contribution do not provide a rational pathway for morphological design.

These concepts were developed in concert with dissolution tests on other amine-pamoate drug substances after obtaining the unexpected dissolution profile for imipramine pamoate. Analogous to the imipramine pamoate dissolution results, the amorphous forms of these drug substances exhibited the slowest rates for reaching equilibrium dissolution while the polymorphic forms were more readily released.

Beyond the anomalous dissolution behavior displayed by the ensemble of amorphous API pamoate salts, a laboratory observation was made identifying pathways controlling the 2:1 versus 1:1 ratio (amine equivalents to moles pamoate). For clarity, disodium pamoate (or its synthetic equivalents) possesses two chelating sites within one molecule, wherein chelation is defined as the amine (from the API) forming a complex through the carboxyl and phenolic residues on the pamoate moiety. Laboratory experiments were performed with the intent of converting an amorphous material to a polymorphic form. Indeed a physical transformation was accomplished, however in some cases a chemical composition change was observed. The original amorphous form was identified as the 2:1 amine:pamoate salt whereas the polymorphic form isolated was the 1:1 amine; pamoate salt. This observation also provides a mechanism for an altered release drug product designed and engineered wherein the release property is available from the API pamoate salt (or other appropriately selected organic acid salt).

Consequently, the amorphous (2:1 pamoate) was evaluated for its dissolution properties under acid conditions. The findings were consistent with the negative teaching expounded upon above, yet the results provide a further refinement to the invention. It was observed that for the following amine pamoate salts, particularly those with a lipophilic character, one equivalent of amine was immediately released. This led to a morphological change in the remaining 1:1 amine:pamoate complex. This new complex exhibited a modified release profile with the amine concentration slowly increasing. The amines particularly exhibiting this property were sibutramine and clomipramine.

The laboratory manipulation of the API (2:1) with the intent of yielding a 2:1 polymorphic form has significant implications with respect to drug product clinical trial testing and evaluation. The intended laboratory physical transformation was conducted under lipophilic conditions and resulted in a chemical change. The dissolution profile experiments confirmed this phenomena would provide modified release characteristics. With respect to clinical trials, drug release, permeability and absorption is evaluated under fed and fasting conditions. Drugs anticipated to face challenges with respect to fed and fasting conditions can now be evaluated using the 2:1 to 1:1 API:pamoate conversion. Under fasting conditions, the 2:1 form allows for immediate release in the gastrointestinal tract. In contrast, under fed conditions, drug absorption is also available via the 2:1 API:pamoate salt since the oleophilic character of the gastrointestinal tract allows for the release of one equivalent of the API followed by the slower release of the second equivalent.

Studies on promethazine pamoate yielded a conflicting result to the trends observed herein in that an amorphous form exhibited an equilibrium solubility profile consistent with the traditional expectation (essentially immediate release). However, the observation has a significantly more complex explanation when characterization data for the three forms are more carefully analyzed. Both forms I and II reported herein were analyzed by DSC and PXRD to ascertain their levels of crystallinity. Initially, it was observed that Form I had a phase transition occurring at about 126° C. and a heat of fusion of about 6 Joules per gram. Further the PXRD diffractogram exhibited characteristics of an amorphous material. The two analyses supported the conclusion that Form I was indeed amorphous. In contrast, the DSC profile of Form II was quite different in that the phase transition was observed at about 230° C. with a heat of fusion of about 74 Joules per gram. These characteristics were indicative of Form II being a more crystalline polymorphic form of promethazine pamoate. It was disturbing therefore to obtain a PXRD diffractogram of Form II that was virtually identical in appearance to Form I. Indeed, Forms I and II, while different by DSC are both amorphous forms of the organic acid addition salt. Form III exhibits a phase transition at about 240° C. with a heat of fusion of about 108 Joules per gram. The corresponding PXRD diffractogram of Form III clearly indicates its highly crystalline, polymorphic state.

In considering the saturation profiles of the three forms, it would be reasonable to expect Forms I and II to behave similarly, and indeed at pH 1 their profiles are essentially identical. However at about pH 4.6 their dissolution profiles begin to diverge and at pH 7.4 their profiles have noticeably separated and to the extent that Form II has begun to behave similarly to that of Form III.

The stoichiometric composition of the three polymorphs was then reviewed more closely. Forms I and II were subjected to proton and C-13 NMR (FIGS. 35, 36, 37 and 38) confirming that Forms I and II were indeed 2:1 salts (promethazine base:pamoate residue). By HPLC assay, Form III was also a crystal habit affording the 2:1 salt. Consequently, the data indicates Form II, while amorphous, has some crystalline nature (as demonstrated by its DSC thermogram). As form II is evaluated for its dissolution properties, a digestion occurs particularly at a pH greater than about 4 wherein Form II is transfigured to Form III. Clearly, the release properties for the promethazine family of organic acid salts exhibit dissolution profiles reflective of rapid morphological changes potentially occurring in the intestinal tract. In this manner, the kinetics of morphological change can be employed to achieve an extended release profile of the drug substance.

The observed equilibrium solubility characteristics of amine-containing organic acid addition salts provides a mechanism to tailor and/or engineer the release properties of drug substances in a human or animal gastrointestinal tract. Often these release properties are accomplished by formulation techniques; this body of work indicates release properties can be an imparted to the API by selection of the appropriate organic acid.

The impact of the organic acid component on the release properties of the API salts, the salt's morphological form, the stoichiometry of the API salt and the response to pH are evidenced in FIG. 39 through FIG. 52 inclusive. Each material was evaluated under equilibrium solubility conditions and it is worthwhile to review the trends observed from these studies. For instance, imipramine pamoate's equilibrium solubility was evaluated at pH 1.00, 3.00, 4.63, 6.00 and 7.40 in FIGS. 39, 40, 41, 42 and 43. It was observed that at pH 1, amorphous or forms with amorphous content exhibited lower amounts of API released than do their polymorphic counterparts. At pH 3.0, the equilibrium solubility profiles clearly indicate a substantial decrease in active ingredient dissolving into solution. Repeating the testing at pH 4.63 indicated only a few percent of each form are available in solution after 2 hours. When the procedure was performed at pH 6.00, the solubility of the various forms, including the amorphous form, exhibited very lithe solubility. And finally, at pH 7.4, the solubility profile has not significantly changed from the condition at pH 4.63.

Figure 44:
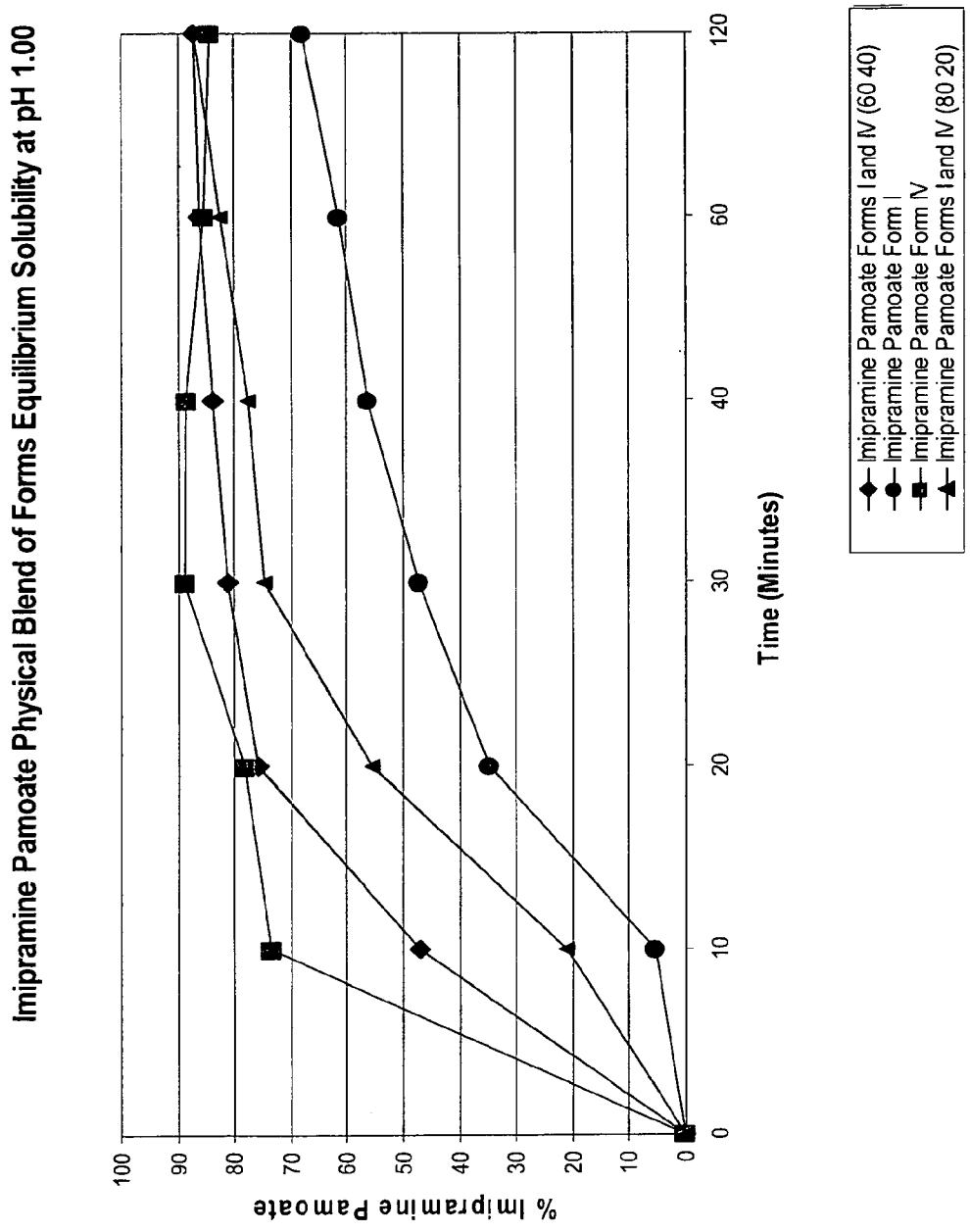
FIG. 44 is a graphical representation of the equilibrium solubility at pH 1.00 of blends of imipramine pamoate morphological forms.

FIG. 44 summarizes the results of evaluating the equilibrium solubility of blends of amorphous and polymorphic imipramine pamoate. The results obtained indicate that at pH 1.00, 60/40 and 80/20 blends of Form I with Form IV yielded solubility profiles reasonably proportional and intermediate to the independent Forms. This observation allows for the formulation of controlled release or extended release products wherein the behavior of the release property is dominated by the organic acid component of the API salt.

As realized the present invention allows for development of a pharmaceutical drug substance with a dissolution profile wherein no more than 50% of the drug substance is released at pH of 1.0 in 2 hours. More preferably, no more than 50% of the drug substance is released at pH of 1.0 in 1 hour. Even more preferably no more than 85% is released at pH of 1.0 in 20 minutes.

Figure 45:
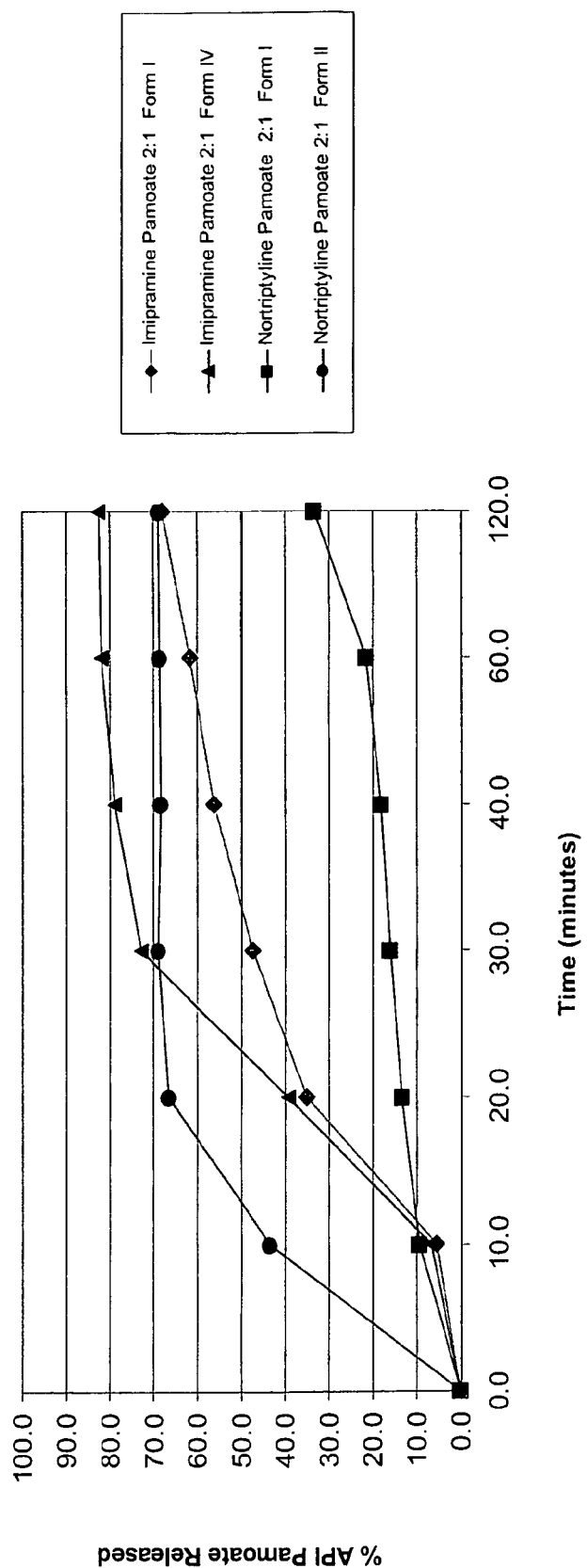
FIG. 45 is a graphical representation of the equilibrium solubility of amorphous 2:1 API pamoate salts versus a polymorphic form of each at pH 1.00.

This conclusion is further supported by the unexpected observation that the amorphous salts of amine containing APIs exhibited an equilibrium solubility profile considerably less than their polymorphic forms. FIG. 45 summarizes these findings at pH 1.00 for 2:1 API-pamoate salts (recalling that the 2:1 refers to the number of API equivalents per molecule of organic acid component).

Figure 46:
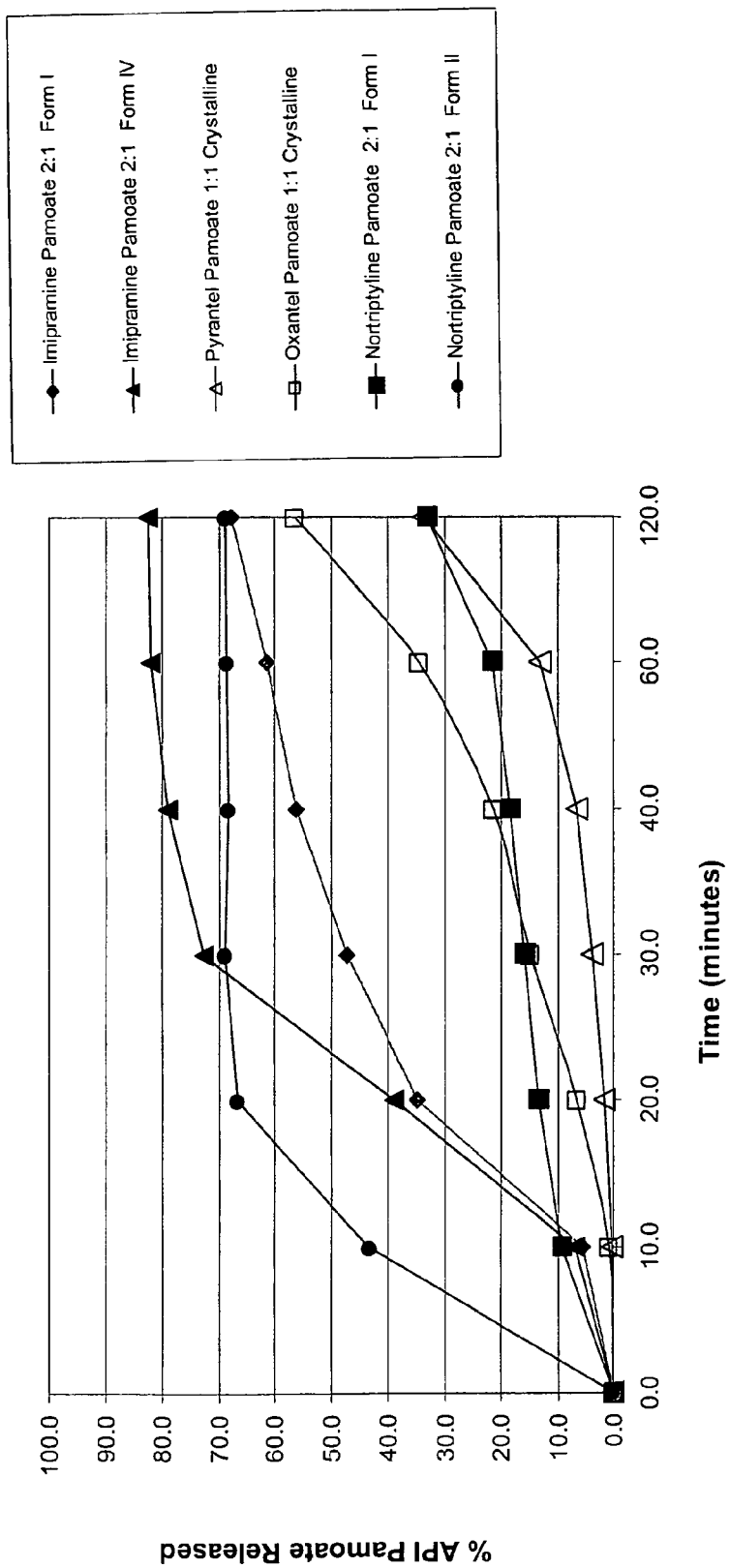
FIG. 46 is a graphical representation of the equilibrium solubility of amorphous and polymorphic forms of 2:1 API pamoate salts versus 1:1 crystalline salts at pH 1.00.
Figure 47:
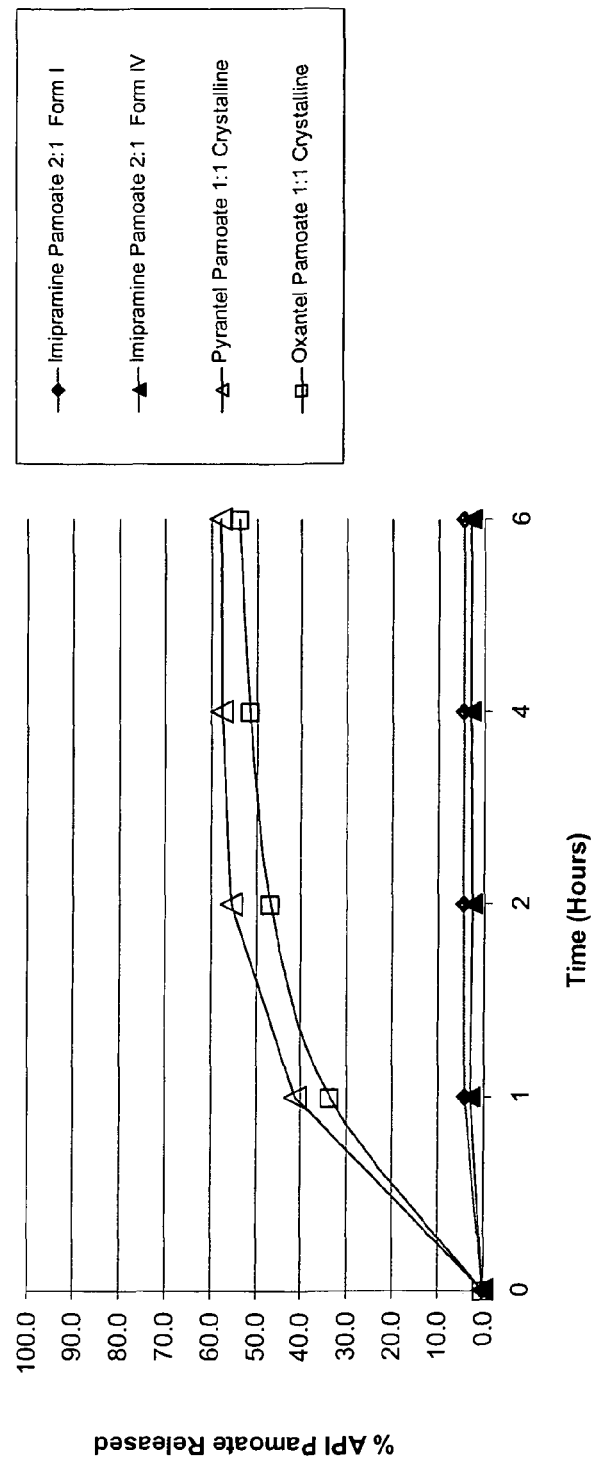
FIG. 47 is a graphical representation of the equilibrium solubility of amorphous and polymorphic forms of 2:1 API pamoate salts versus 1:1 crystalline salts at pH 7.40.

To evaluate the stoichiometric factor contributing to variations in equilibrium solubility profiles, 2:1 pamoate salts were compared to salts exhibiting a 1:1 stoichiometric relationship. As can be seen in FIG. 46 at pH 1.00, the 1:1 pamoate salts exhibit a markedly different profile than the 2:1 salts such that the 1:1 salts are substantially less soluble than the polymorphic forms of the 2:1 salts. The 1:1 salts have a solubility profile more resembling the amorphous forms of the 2:1 salts. Further, a very valuable observation is found in FIG. 47 wherein at pH 7.4, the solubility profiles of the 1:1 salts "reverse" as compared to the 2:1 amorphous and polymorphic forms. This reverse response provides for a mechanism to deliver APIs directly to the intestine. This design feature for a drug substance may be particularly useful for drug substances which may be unable to withstand the highly acidic conditions of the stomach.

Figure 48:
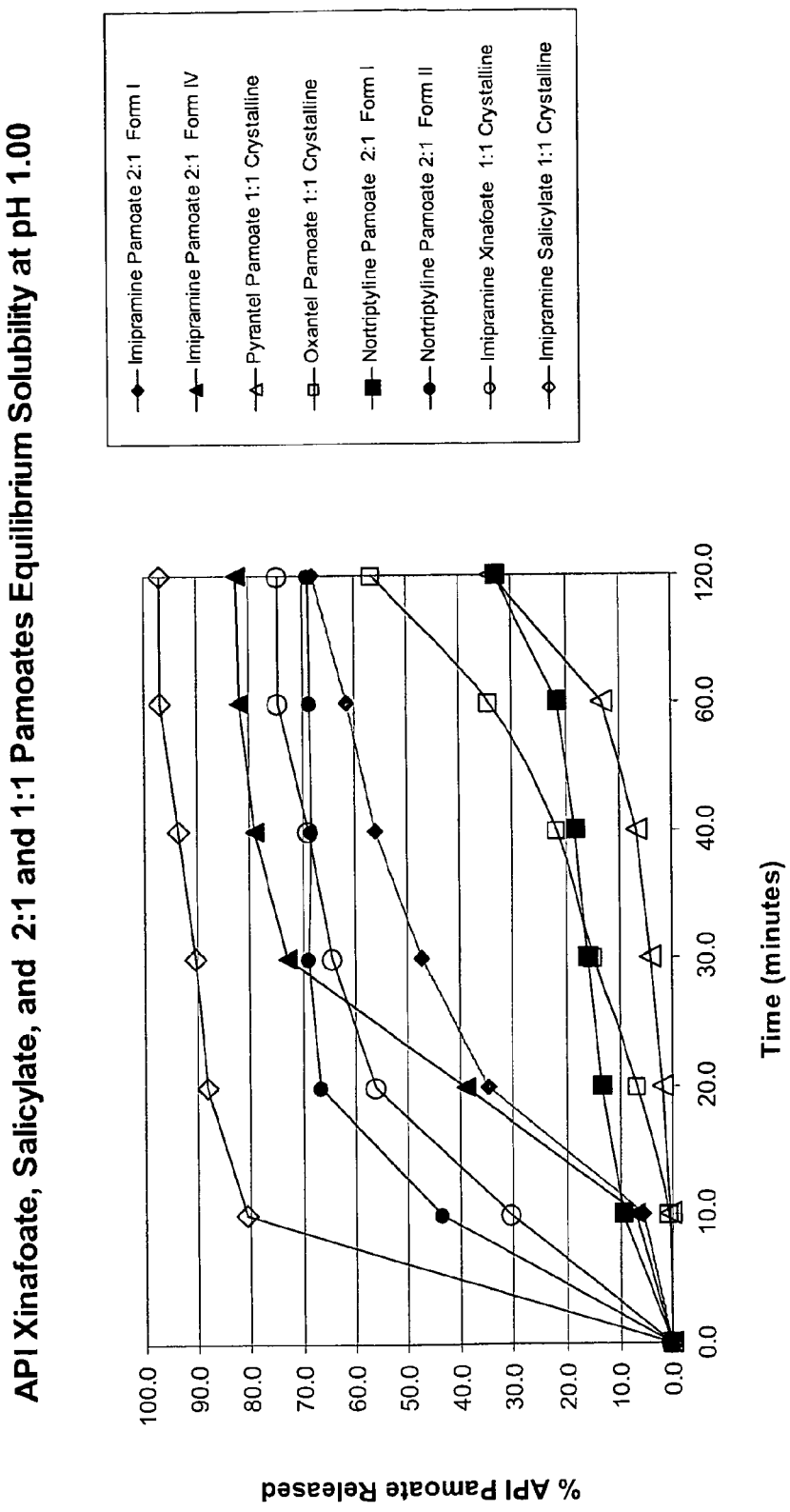
FIG. 48 is a graphical representation of the equilibrium solubility of amorphous and polymorphic forms of API xinafoate, salicylate, and 2:1 and 1:1 pamoates at pH 1.00.

Besides pamoates, other families of analogous organic acid salts are described previously herein and include xinafoate and salicylate salts. Stoichiometrically, only 1:1 salts are available using these organic acid components. FIG. 48 provides an equilibrium solubility comparison of amorphous and polymorphic forms of API—xinafoate, -salicylate, and 2:1 and 1:1 pamoates at pH 1.00. At pH 1.00 there are essentially four families of equilibrium solubility profiles depending on the particular salt formed with an API (a salicylate, xinafoate or pamoate) and depending upon the amorphous or crystalline character of the salt. These families of salts can be ranked in decreasing order of solubility at pH 1.0: the API-salicylate salt is the most soluble >xinafoate and pamoate crystalline forms >amorphous pamoates (2:1), >crystalline pamoates (1:1). The 2:1 amorphous pamoates and the 1:1 crystalline pamoates share an overlap region in the dissolution profile.

Figure 49:
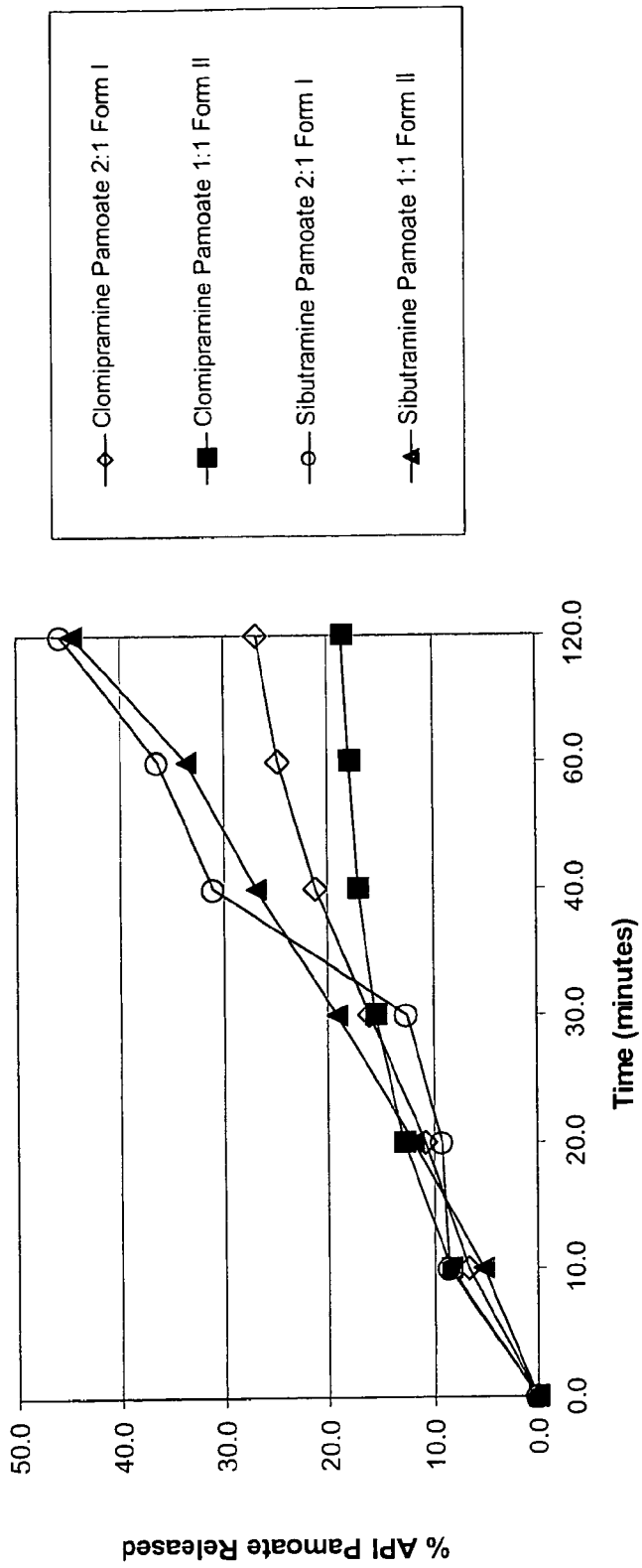
FIG. 49 is a graphical representation of the equilibrium solubility of clomipramine and sibutramine as their amorphous (2:1) and polymorphic (1:1) pamoate salts at pH 1.00.
Figure 50:
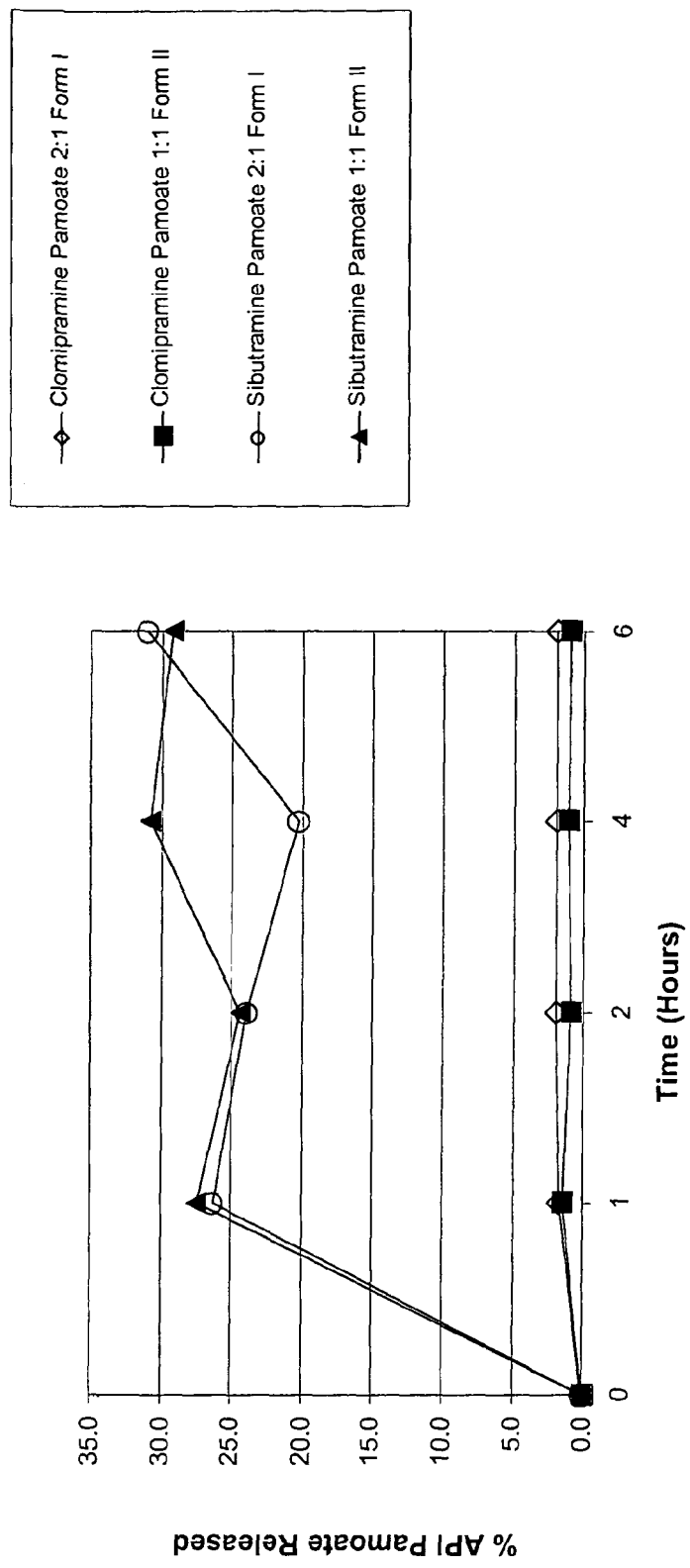
FIG. 50 is a graphical representation of the equilibrium solubility of clomipramine and sibutramine as their amorphous (2:1) and polymorphic (1:1) pamoate salts at pH 7.40.
Figure 51:
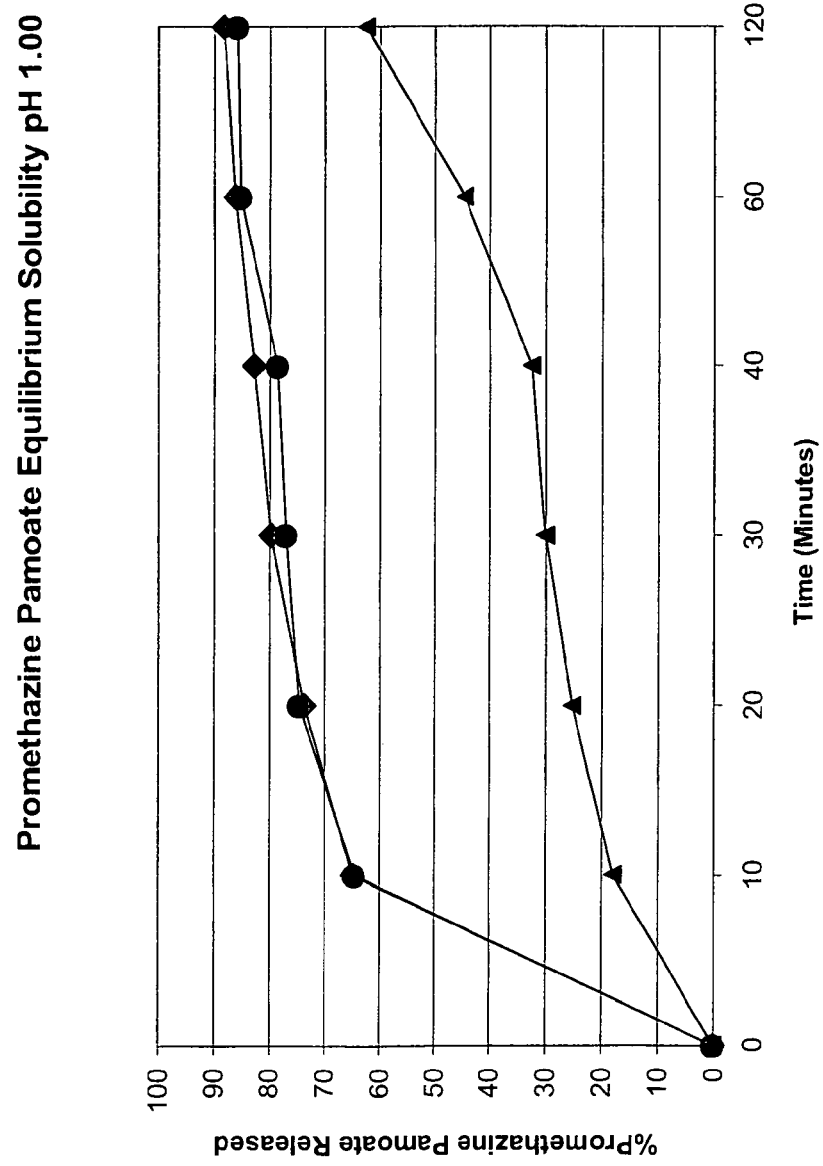
FIG. 51 is a graphical representation of the equilibrium solubility of amorphous and polymorphic forms of promethazine pamoate at pH 1.00.

In an effort to challenge the observed findings, two APIs were selected which have more lipophilic character in order to determine the equilibrium solubility response of these materials as their organic acid addition salts. Clomipramine and sibutramine were selected due the presence of a chloro substituent on an aryl moiety within their chemical structures. Interestingly, their amorphous salts are isolated as the 2:1 salt whereas a polymorphic form is isolated as the 1:1 pamoate. FIG. 49 summarizes the equilibrium solubility profiles for these two APIs. At pH 1.00, the equilibrium solubility profile overlap between the 2:1 amorphous pamoates and the 1:1 crystalline pamoates is apparent. However, here too the general trend continues. The amorphous (2:1) pamoates of clomipramine and sibutramine are more soluble than their polymorphic (i.e. crystalline) 1:1 pamoates. At pH 7.4, (see FIG. 50), the discrepancy between specific compound behavior is magnified, however, the general trend follows. The selection of these two compounds was with purpose in that the presence of the chloro substituent on an aryl group within both APIs' structures was anticipated to lower their overall solubility. Despite this substituent effect (correlating to Log P within Lipinki's Rules), the general trends associated with a selected family of conjugate salt remained true.

Figure 52:
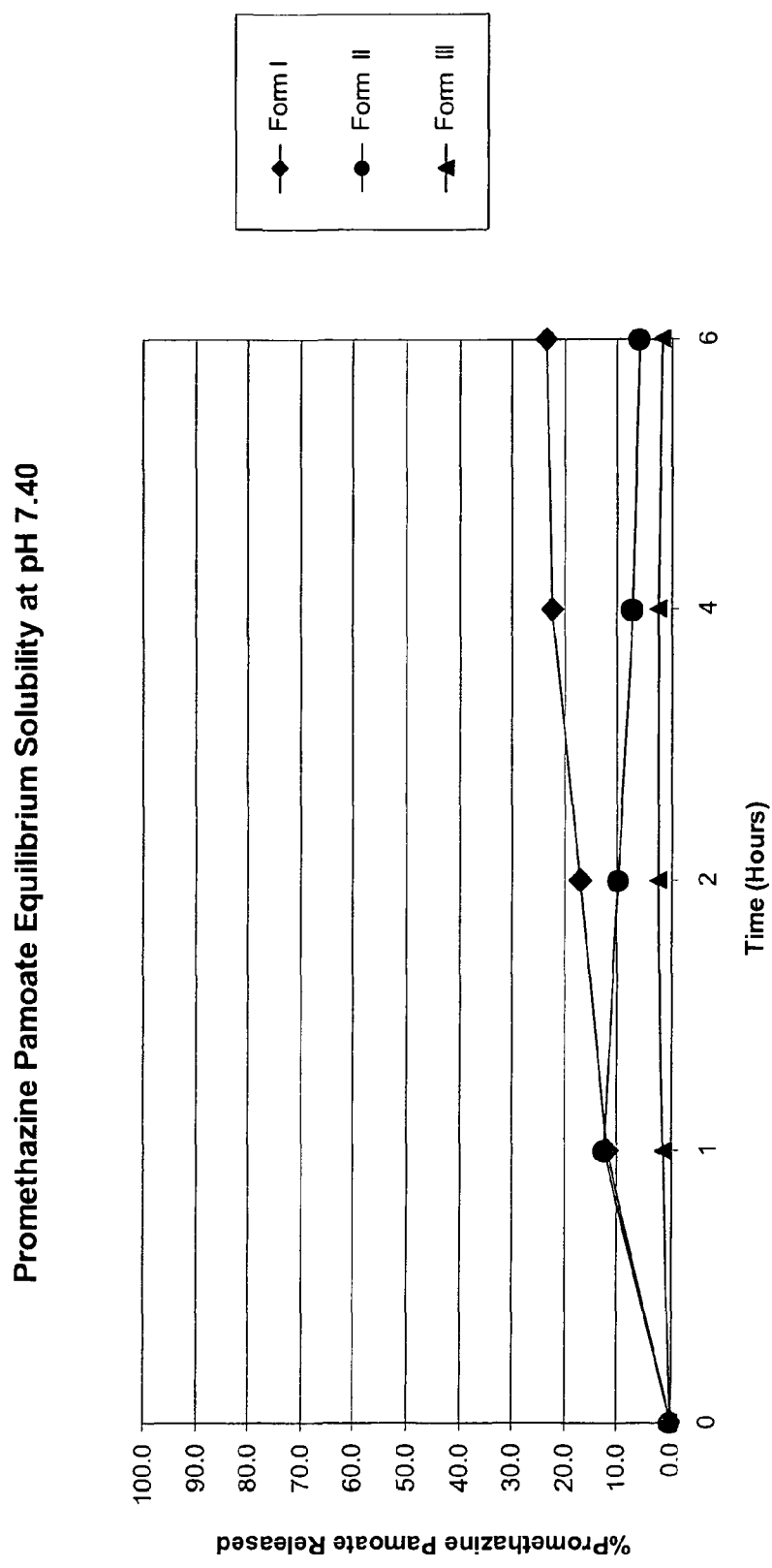
FIG. 52 is a graphical representation of the equilibrium solubility of amorphous and polymorphic forms of promethazine pamoate at pH 7.40.

Similarly, the study of promethazine pamoate was undertaken to challenge the impact of aryl-heteroatom effects on equilibrium solubility as a function of polymorphic form. Historically, imipramine was developed to be bio-isosteric to promethazine in that the ethano-bridge within imipramine is essentially the same size as the sulfur atom within promethazine, (Burger's Medicinal Chemistry and Drug Discovery, Volume 5, 5$^{th}$ ed., p. 263, edited by Manfred E. Wolff, © 1997 by John Wiley & Sons). While the cycloheptyl ring of imipramine has some conformational flexibility, the central ring of promethazine (a phenothiazine) is essentially locked into a boat conformation. The boat conformation provides a 1,4-chelation ability of the thiazine portion of the molecule. This conformation provides for an enhanced crystalline lattice of the pamoate polymorphic forms isolated. Consequently, the aryl-heteroatom effects within promethazine contribute to the observed, comparatively high phase transition enthalpies (e.g. >100 Joules/gram) observed for promethazine pamoate Form III. Indeed, DSC analysis can provide insight into API pamoate, xinafoate and salicylate salt equilibrium solubility profiles and can be correlated to the unexpected results obtained from the promethazine pamoate equilibrium solubility studies. Hence, the API salts formed from these families of organic acids that exhibit phase transition enthalpies greater than about 75 Joules/gram yield equilibrium dissolution profiles comparable to the overly-generalized conventional expectation: namely, amorphous compounds are more soluble than their polymorphic forms. In actuality, the highly crystalline pamoates with phase transition enthalpies greater than about 75 Joules per gram behave more like the 1:1 salts. FIG. 52 indicates the limited solubility of the promethazine pamoate forms at pH 7.4.

The observed trends have valuable commercial application in the development of new drug products and the re-engineering of generic offerings. As is seen in the co-pending application, Salts of Physiologically Active and Psychoactive Alkaloids and Amines Simultaneously Exhibiting Bioavailability and Abuse Resistance, the preparation of organic acid addition salts of amine-containing APIs can retain the intended pharmacological response of the drug substance yet impart an anti-abuse feature to the product. Herein, it has been demonstrated that the dissolution response of a given drug substance can be modified, engineered or tailored to meet a given requirement depending upon the family of organic acid selected to form the salt.

By way of example, there are a number of FDA approved drugs useful in gastroenterology treatments. The compounds are: lubiprostone, palonosetron, aprepitant, oxybutynin, rabeprazole sodium, nitazoxanide, oxaliplatin/5-fluorouracil/leucovorin, imatinib mesylate, adefovir dipivoxil, nitisinone, peginterferon alfa-2a, pantoprazole sodium, secretin, tegaserod maleate, mesalamine, budesonide, esomeprazole magnesium, ribavirin, balsalazide disodium, alosetron HCl, lansoprazole, prilosec, cimetadine HCl, prochlorperazine, ranitidine, ciprofloxacin, meropenem, cyanocobalamin, omeprazole, and iodixanol. There are also several drugs in development for the treatment of irritable bowel syndrome (IBS) and include renzapride, cilansetron, asimadoline, and talnetant. Within this recitation are drug substances containing a benzimidazole or indole functionality as part of the pharmocophore. Of the benzimidazole variety are rabeprazole, pantoprazole, lansoprazole, omeprazole and esomeprazole. Within the indole family of drug substances are alosetron and tergaserod. The findings of the present invention are most applicable to delivering amine containing APIs to the intestine without reliance on enteric coatings, for example by preparation of the 1:1 organic acid addition salt, and thereby avoid ineffective or detrimental processes of drug release in the stomach. As such the current invention provides a mechanism to engineer targeted release in either the stomach or intestine.

Another IBS drug currently entering Phase III trials is the product Rezular which contains Arverapamil a single enantiomer of the drug substance Verapamil (a Class IV controlled substance). This announcement, observed in Drug Pipeline Alert™ Thursday, Oct. 2, 2007, Vol. 5, No. 195, published by RxTrials Institute, indicates the continued interest in obtaining effective drugs for the treatment of this disease. The active ingredient contains a tertiary nitrogen center, as part of a phenethyl amine residue within the molecule. The present invention is well suited for providing the organic acid addition salt of either enantiomer (or the racemate) to provide both delivery to the intestine and eliminate any potential for abuse.

The treatment of urinary incontinence also receives considerable attention. Two drug product exemplars in this class are Vesicare® containing the active ingredient solifenacin succinate, and Enablex® containing the active ingredient darifenacin hydrobromide. While both compounds would be susceptible to the features of the present invention, the development of darifenacin hydrobromide is worth comment. The FDA's Orange Book identifies U.S. Pat. No. 5,096,890 and U.S. Pat. No. 6,106,864 (both patents incorporated herein by reference) with associated Patent Use Codes of U-631 and U-630, respectively. Patent Use Code U-630 corresponds to "treating urinary incontinence by administering an extended release form of darifenacin". In the '864 patent, the authors report that a pharmaceutical dosage form of darifenacin was "adapted for administration to the gastrointestinal tract of a patient" and that "the formulation minimizes unwanted side-effects and increases the bioavailability of darifenacin". Indeed, the extended release formulation methodology described within the '864 patent are characteristics available through the API when subject to the present invention. Similarly, the concepts of the present invention are easily applied to solifenacin succinate to yield enhanced properties.

As opposed to the extended release or targeted release features, immediate release products can be prepared from polymorphic forms of an API (particularly with the pamoates or salicylates). A controlled or extended release product can be prepared using mixtures of stable amorphous and polymorphic blends of API pamoate salts, and or mixed salts. The mixed salts may include any of the pamoate, xinafoate, salicylate families of organic acids used to form the salt with the API. In this manner, a specific pharmacokinetic profile can be engineered into the drug substance. These approaches provide for obtaining immediate, controlled, extended, sustained and targeted release embodiments by preparing the appropriate organic acid addition salt of amine-containing APIs.

A particular advantage of the present invention is that the phase transition activation energy of the materials is unaffected by the catalytic presence of normal materials typically incorporated during the manufacturing and distribution process or which are absorbed from the environment. Particular materials of interest wherein it is preferred that the phase transition activation energy is not affected include water, organic solvents, non-nucleophilic excipients, fats and oils. Therefore, materials which may normally be incorporated, either purposefully or by environmental alterations do not impact the morphological stability of compounds employing the present invention.

Yet another advantage of the present invention is that the activation energy for phase change exceeds the energy normally imparted by mechanical alterations typically employed in the manufacturing environment such as milling, granulation, compaction, mixing, stirring, agitating and packaging. This greatly increases the manufacturing robustness and decreases losses due to morphological phase transitions during manufacture or which occur as a result of manufacture.

Throughout the disclosure the terms 1:1 and 2:1 refer to the nominal ratio of active pharmaceutical ingredient and counterion which is defined to be within the normal manufacturing tolerance. Therefore, any reference to 1:1 is inclusive of ratios between about 0.95:1 and about 1.05:1. Similarly, any reference to 2:1 is inclusive of ratios between about 1.95:1 and about 2.05:1.

Throughout the disclosure all measurements are done at ambient temperatures and pressures in aqueous solution unless otherwise specified. Any reference to an physiological conditions refer to standard physiological properties including temperature and pH in unless otherwise specified.

Throughout the disclosure references to a specific measurement, such as pH, temperature, time and the like includes the standard deviation consistent with the measurement in standard laboratory conditions as indicated by the number of significant figures.

EXPERIMENTAL

Methods

Differential Scanning Calorimetry
Samples were evaluated using a Differential Scanning Calorimeter from TA Instruments (DSC 2010). Prior to analysis of samples, a single-point calibration of the TA Instruments DSC 2010 Differential Scanning Calorimeter (DSC 2010) with the element indium as calibration standard (156.6±0.25° C.) was completed.
Infrared Spectroscopy
IR Spectra were obtained in a KBr disc using a Perkin Elmer Spectrum BX Fourier Transform Infrared Spectrophotometer.
Powder X-Ray Diffraction
Powder X-Ray diffraction patterns were acquired on a Scintag XDS2000 powder diffractometer using a copper source and a germanium detector.
HPLC
HPLC analyses were performed on a Waters 2695 HPLC system equipped with a Waters 2996 photo diode array detector.
$^1$H and $^{13}$C NMR Spectroscopy
Proton ($^1$H) and carbon-13 ($^{13}$C) NMR spectra were obtained on a JEOL ECA 500 NMR Spectrometer with samples prepared as solutions in deuterated solvents.
Dissolution
Dissolution testing was performed using a Distek Dissolution System 2100 consisting of six 1000 mL dissolution vessels with covers containing sampling ports, six stainless steel paddles and spindles, RPM control unit, and a Distek TCS0200C Water Bath, Temperature Controller Unit.

Example 1

Preparation of Imipramine Pamoate Polymorphs

Imipramine pamoate Forms I, II, III, and IV were prepared according to the procedures found in U.S. patent application Ser. No. 11/595,379 filed on Nov. 29, 2006. The preparation and isolation of imipramine pamoate Form VII was performed according to the procedure of U.S. patent application Ser. No. 11/843,690 filed Aug. 23, 2007 which is incorporated by reference.

Example 2

Preparation of Sibutramine Pamoate Form I

Figure 3:
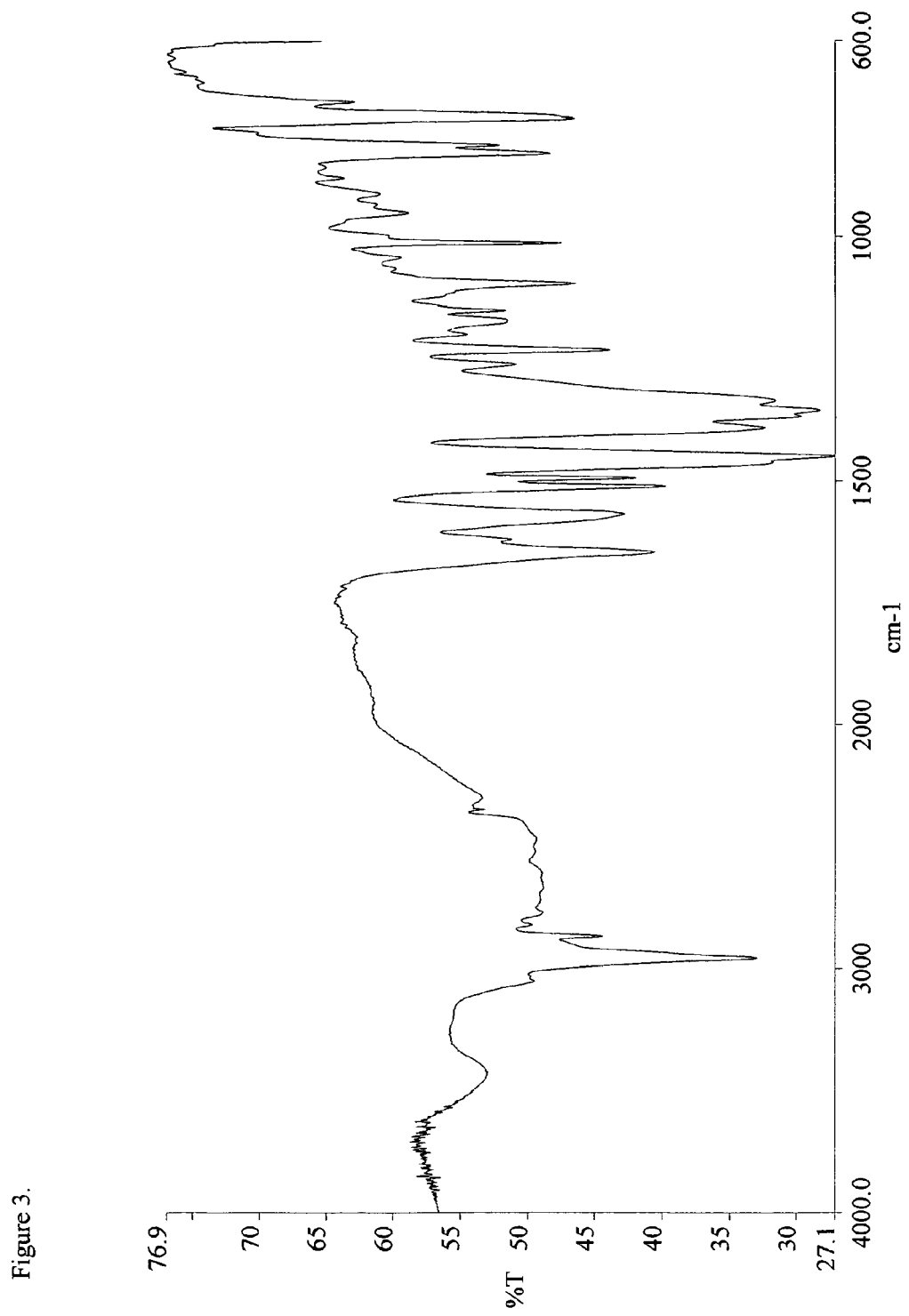
FIG. 3 is a FTIR spectrum of sibutramine pamoate Form I.
Figure 5:
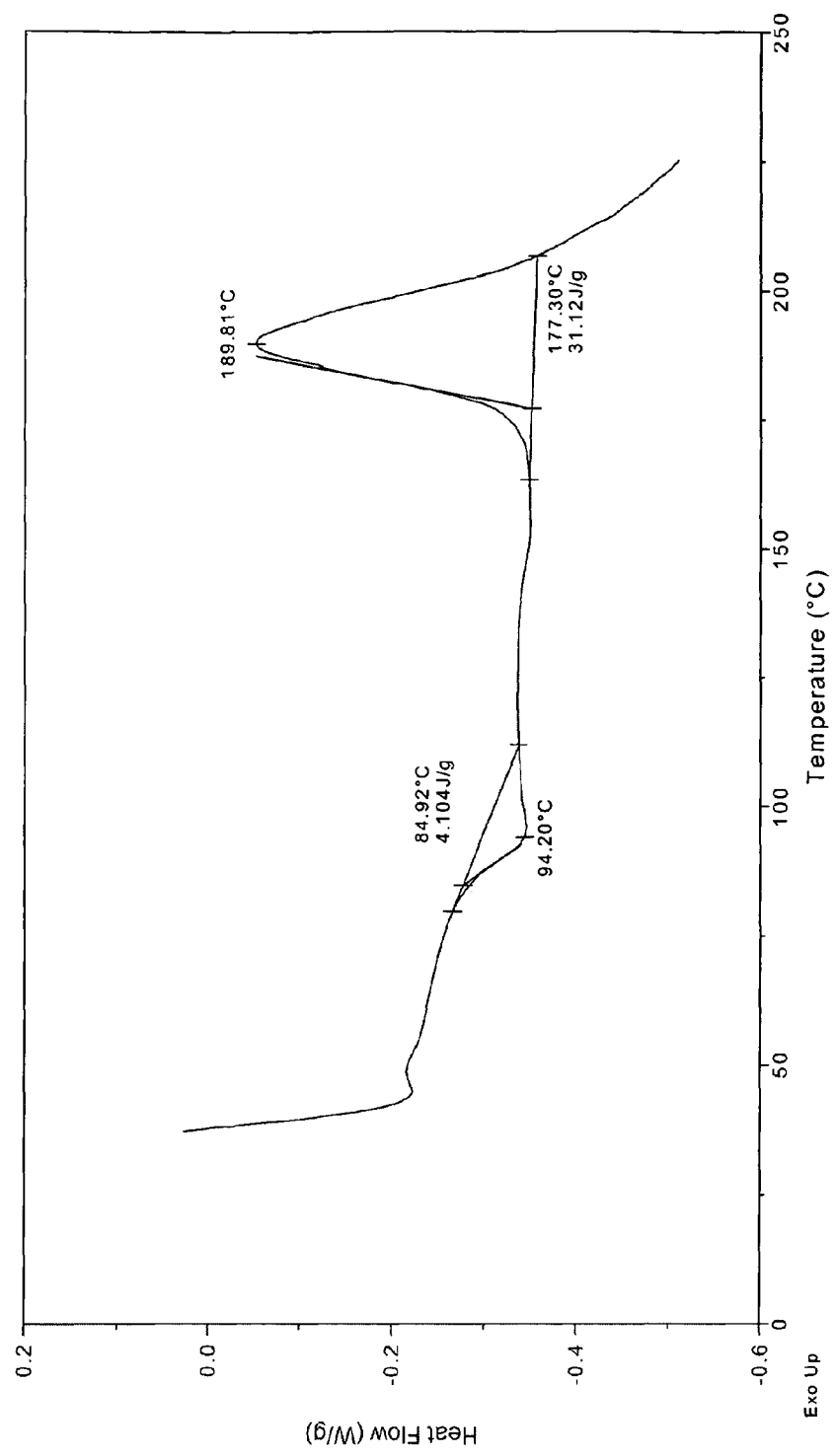
FIG. 5 is a DSC thermogram of sibutramine pamoate Form I.
Figure 7:
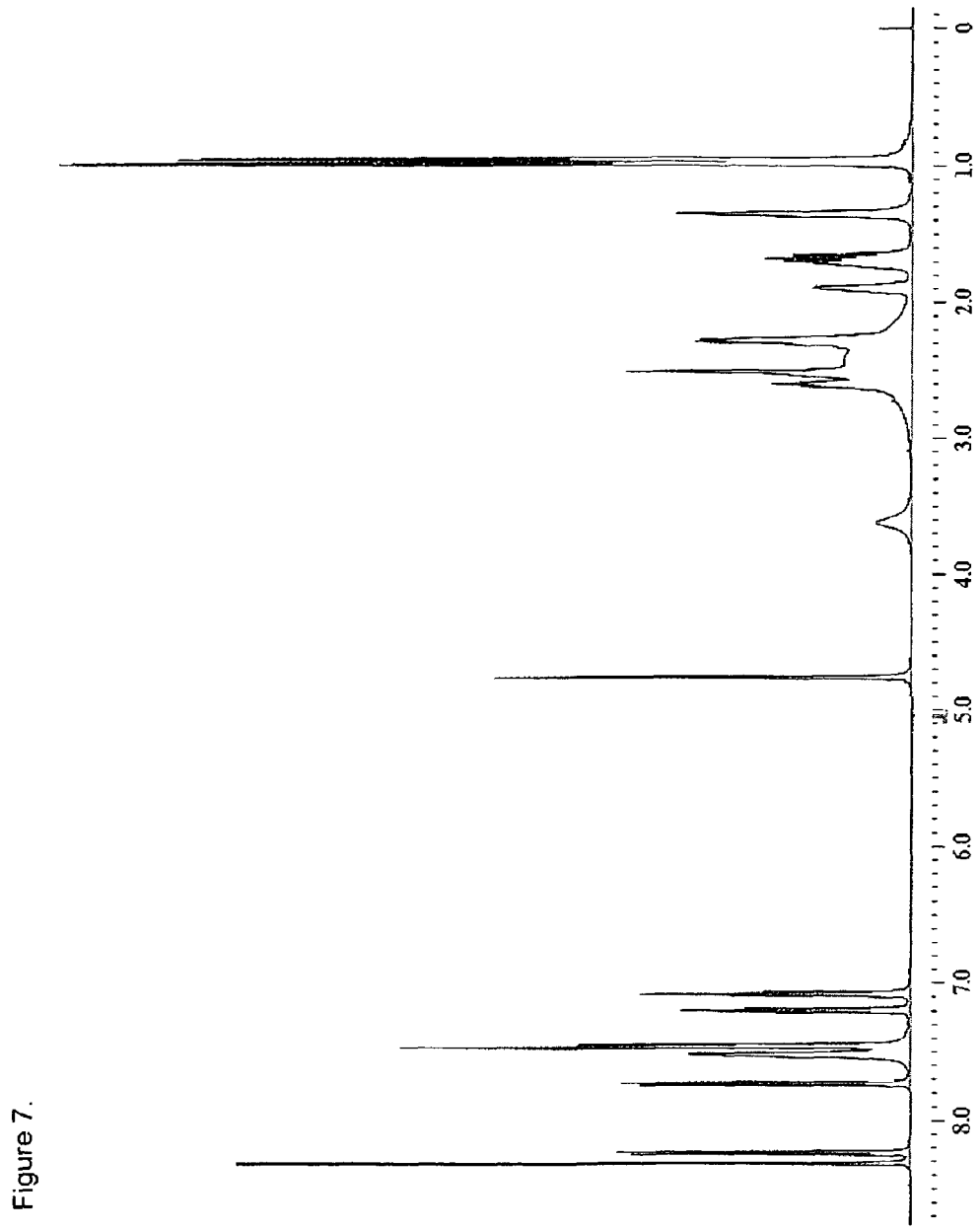
FIG. 7 is an $^1$H NMR spectrum of sibutramine pamoate Form I

To a solution containing 30.96 g of disodium pamoate in 370 g of water was added a dilute HCl or NaOH solution to adjust the solution to about pH 9.4. To a second solution of 50.52 g of sibutramine HCl in 102.0 g of ethanol and 320 g water was added dilute HCl or NaOH solution to adjust the solution to about pH 4.5. The sibutramine HCl solution was added to the disodium pamoate solution over a period of about 2 h. The mixture was stirred and held at about 50° C. for approximately 18 h. The mixture was cooled to below about 25° C. and the solids were collected by filtration. The solid cake was washed with heptanes. The solid cake was dried at about 60° C. under vacuum to yield a powder (32.0 g). By $^1$H NMR (FIG. 7) this characterized as the 2:1 pamoate salt and defined as amorphous Form I by PXRD (FIG. 1), IR (FIG. 3) and DSC (FIG. 5).

Example 3

Preparation of Sibutramine Pamoate Form II

Figure 2:
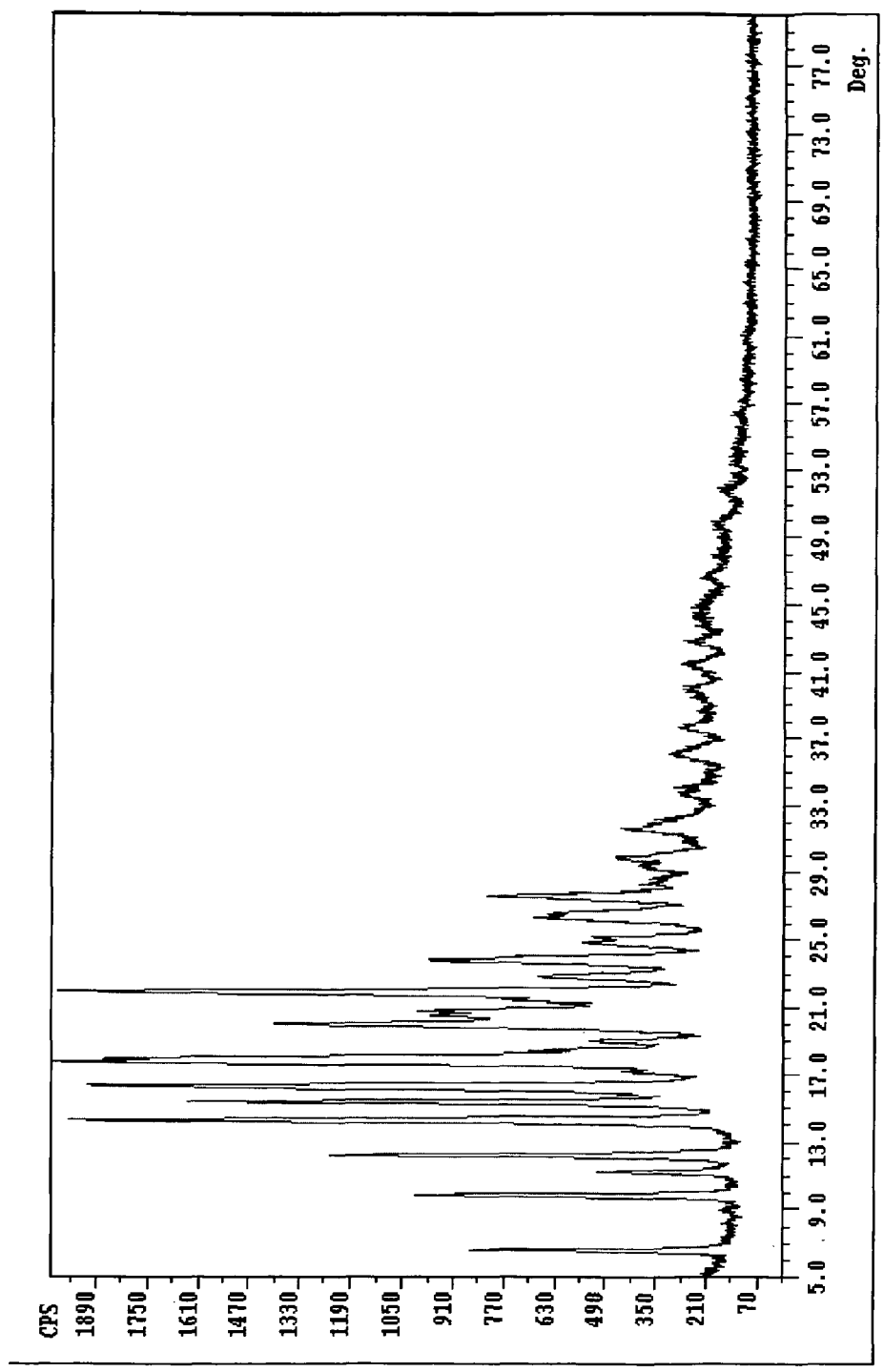
FIG. 2 is a PXRD diffractogram of sibutramine pamoate Form II.
Figure 4:
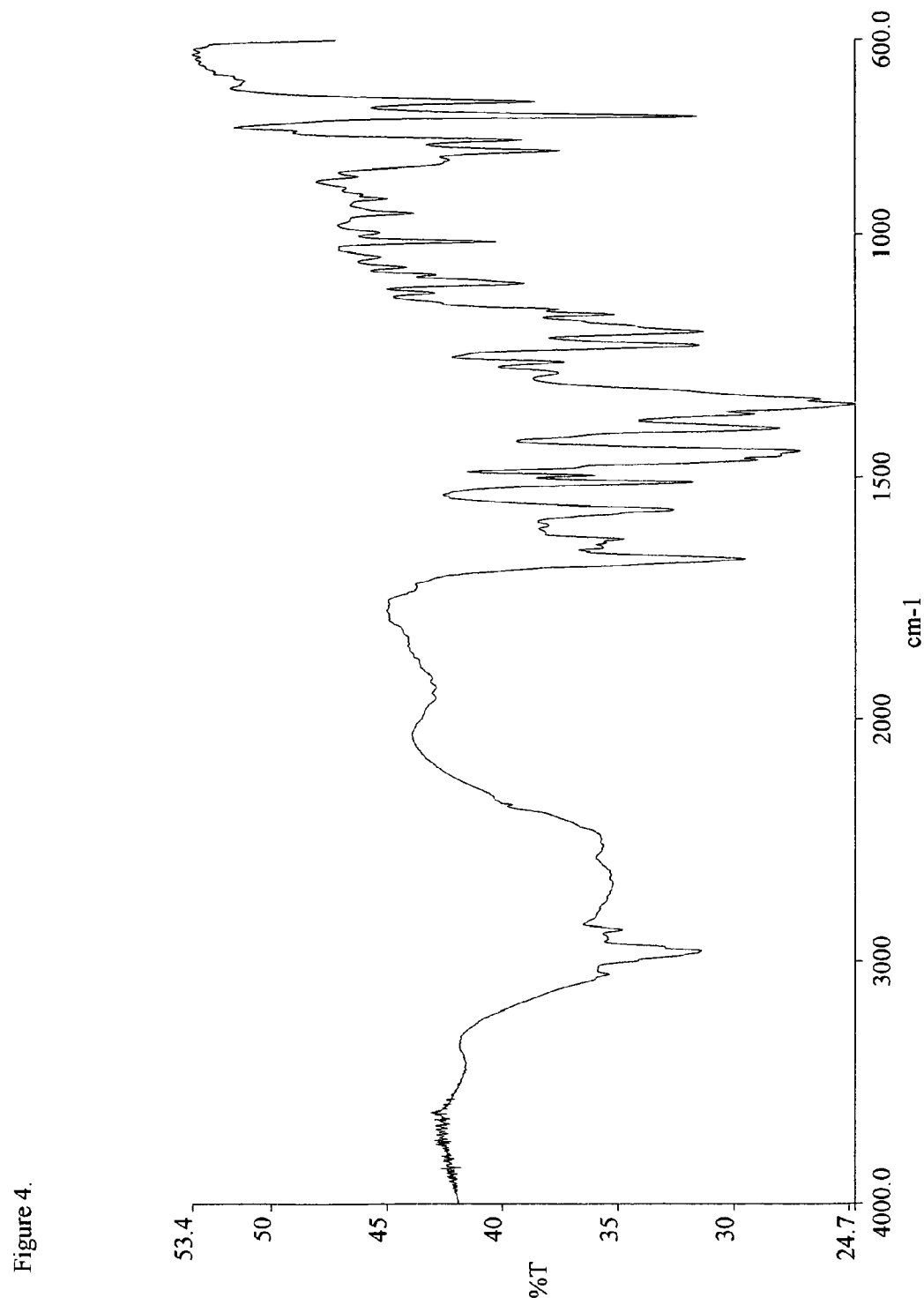
FIG. 4 is a FTIR spectrum of sibutramine pamoate Form II.
Figure 6:
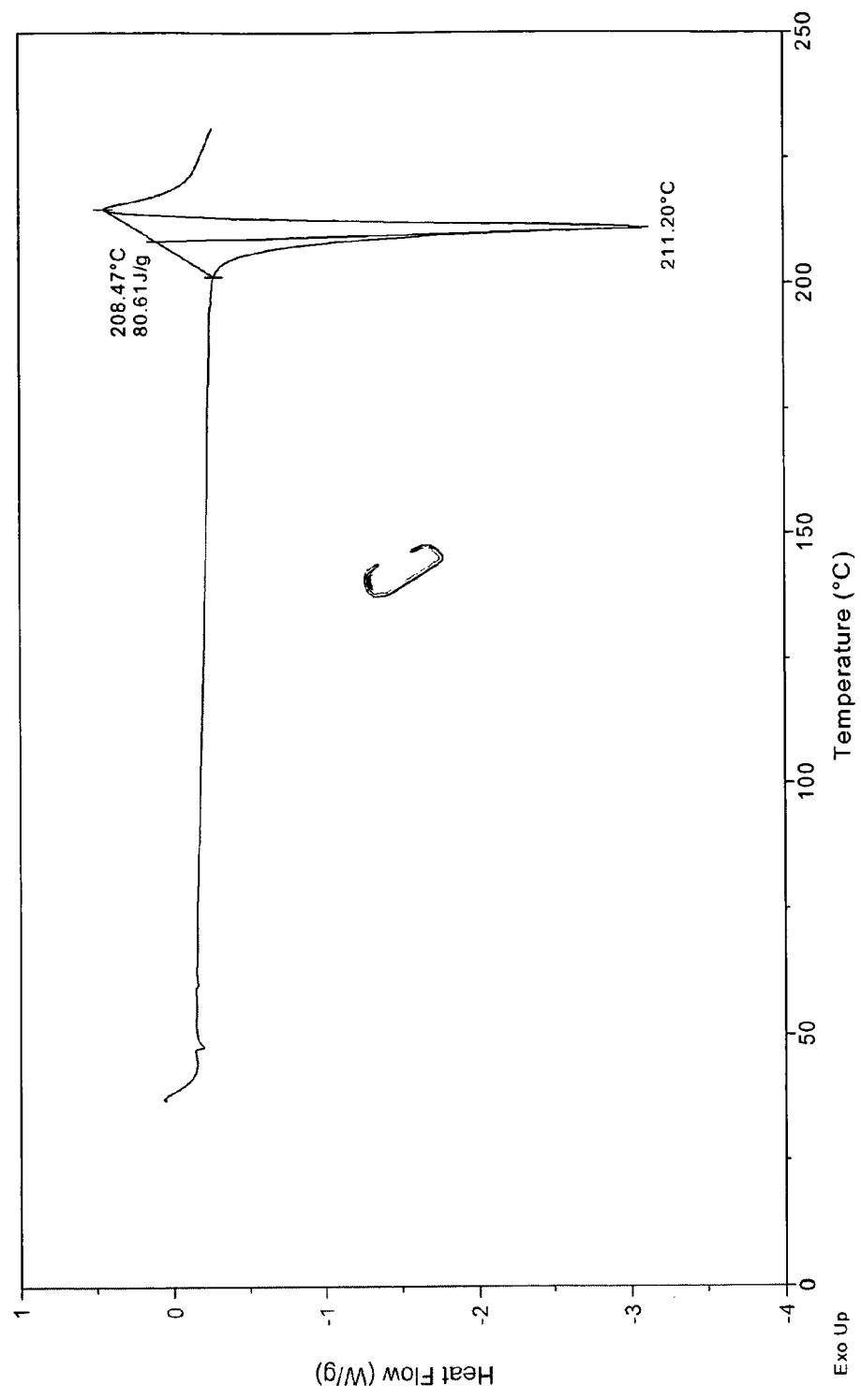
FIG. 6 is a DSC thermogram of sibutramine pamoate Form II.
Figure 8:
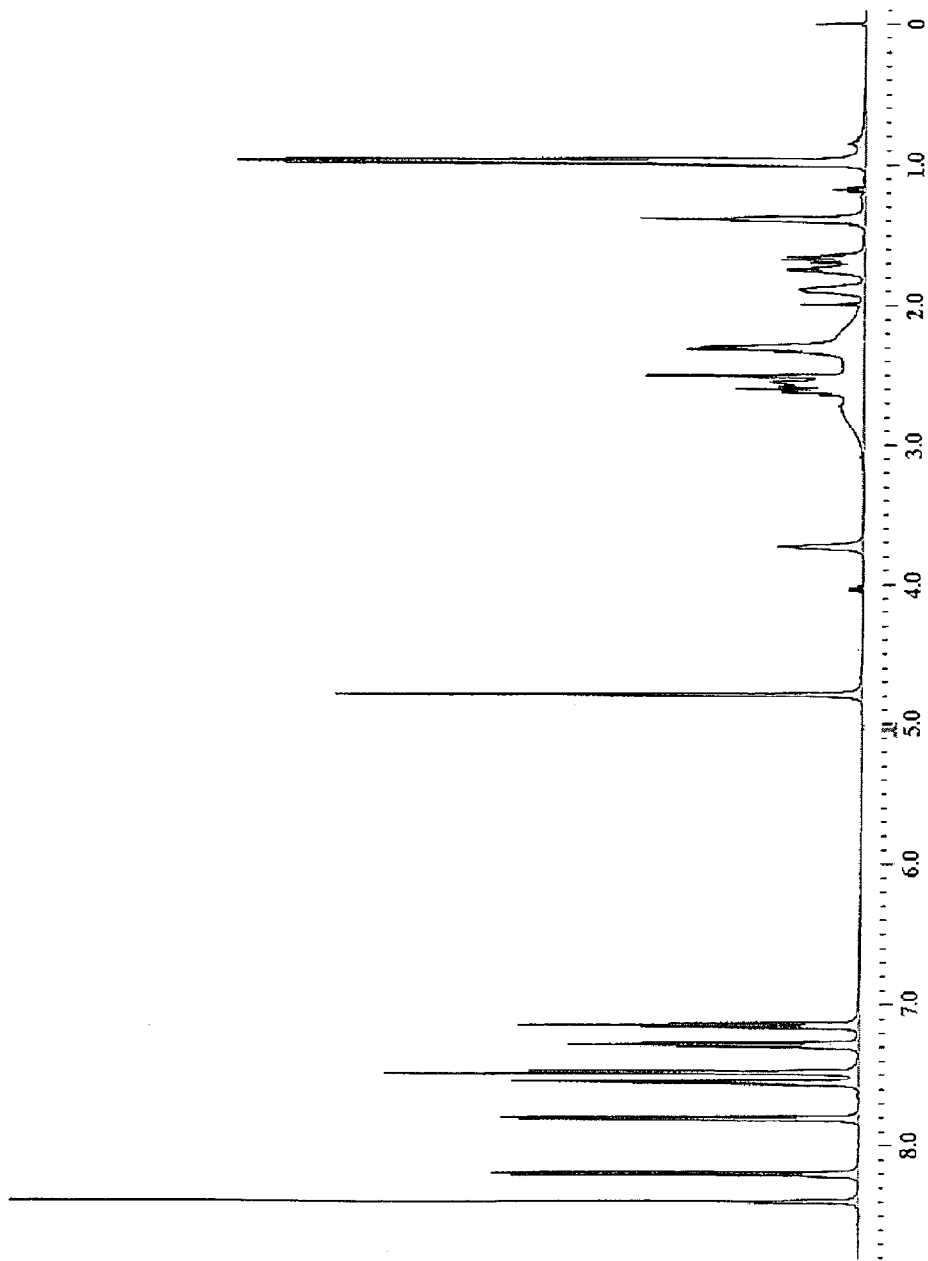
FIG. 8 is an $^1$H NMR spectrum of sibutramine pamoate Form II.

A solution containing 1 g of sibutramine pamaoate (Form I; prepared as in Example 2 above) and 9 g of ethyl acetate was charged to 48 g of heptanes over about 2 minutes at around 25° C. The resulting suspension was held at about 25° C. for approximately 4 h. The solids were collected by filtration. The solid cake was washed with water and then dried at 80° C. under vacuum to yield a powder (0.6 g). By $^1$H NMR (FIG. 8), the material was characterized as the 1:1 pamoate salt and defined as polymorphic Form II by PXRD (FIG. 2), IR (FIG. 4) and DSC (FIG. 6).

Example 4

Preparation of Nortriptyline Pamoate Form I

Figure 9:
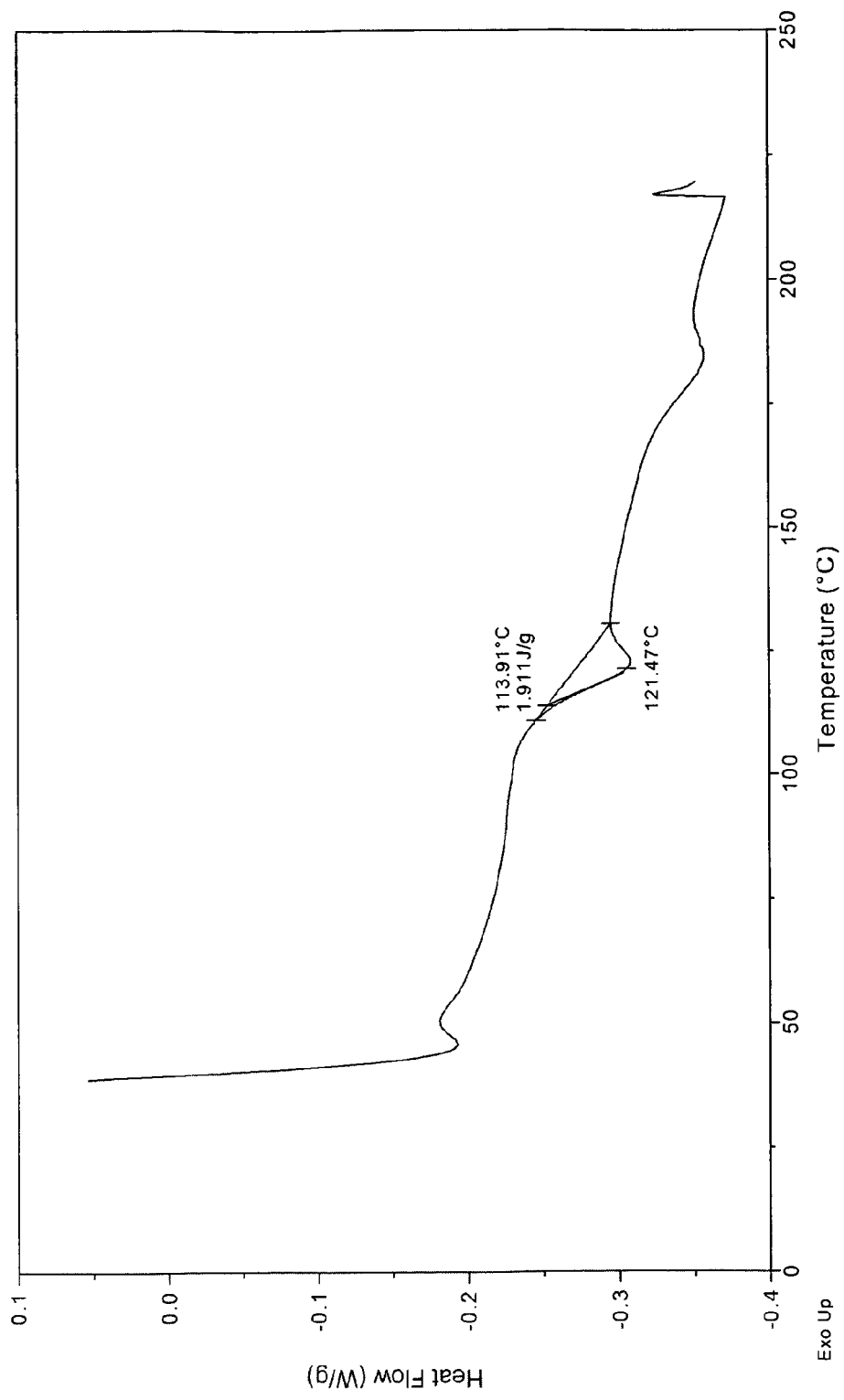
FIG. 9 is a DSC thermogram of nortriptyline pamoate Form I.
Figure 11:
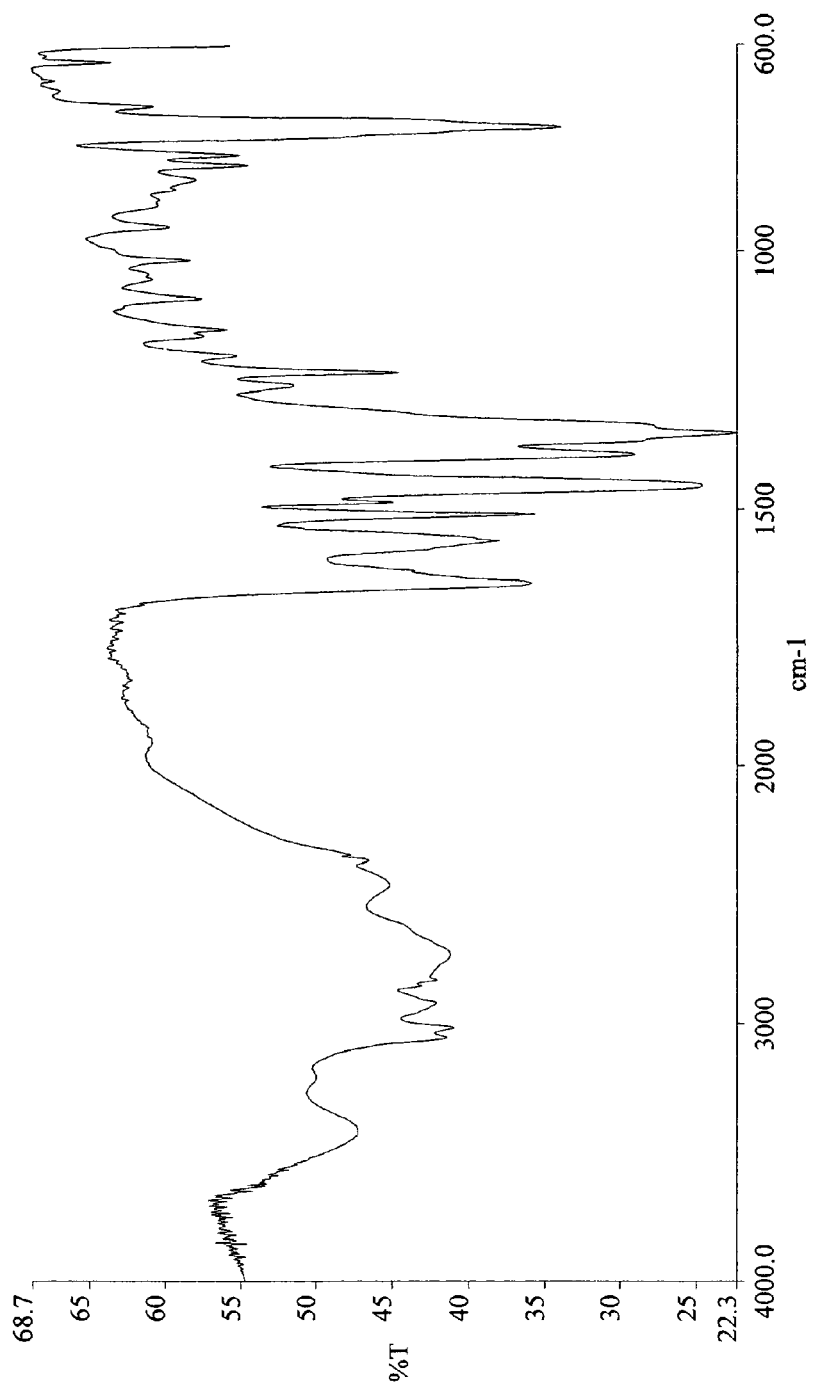
FIG. 11 is a FTIR spectrum of amorphous notriptyline pamoate Form I.

To a solution containing 14.25 g of disodium pamoate in 171.0 g of water was added a dilute HCl or NaOH solution to adjust the solution to about pH 9.4. To a second solution of 20.0 g of nortriptyline HCl in 118.0 g of water and 40 g of EtOH was added dilute HCl or NaOH solution to adjust the solution to about pH 4.5. The nortriptyline HCl solution was added to the disodium pamoate solution over a period of about 3 h. The mixture was stirred and held at about 53° C. for approximately 8 h. The mixture was cooled to below about 25° C. and the solids were collected by filtration. The solid cake was washed with USP purified water. The wet cake was dried at about 70° C. under vacuum to yield a solid (27.0 g). The material was characterized as the amorphous 2:1 pamoate salt; DSC (FIG. 9) and FTIR (FIG. 11).

Example 5

Preparation of Nortriptyline Pamoate Form II

Figure 10:
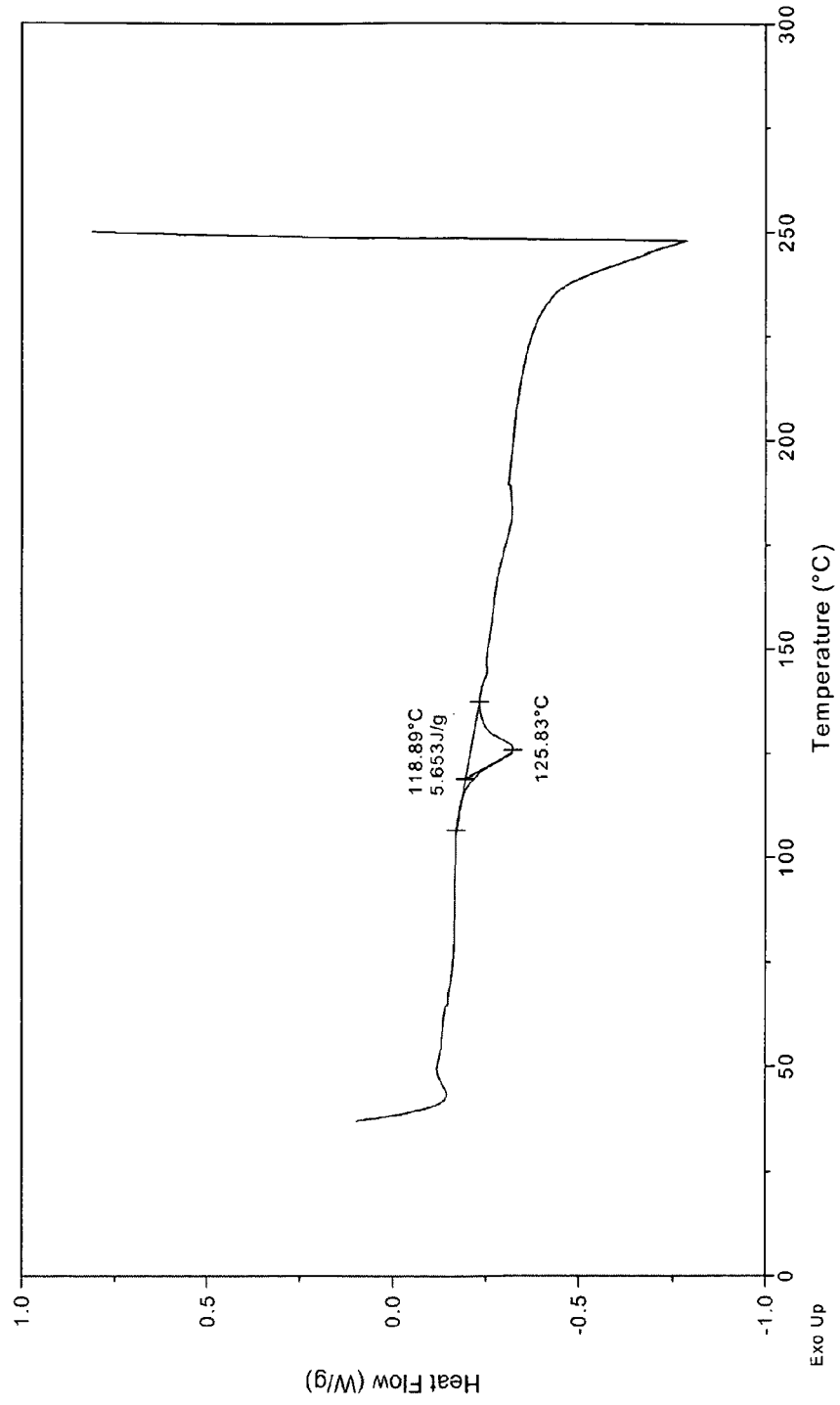
FIG. 10 is a DSC thermogram of nortriptyline pamoate Form II.
Figure 12:
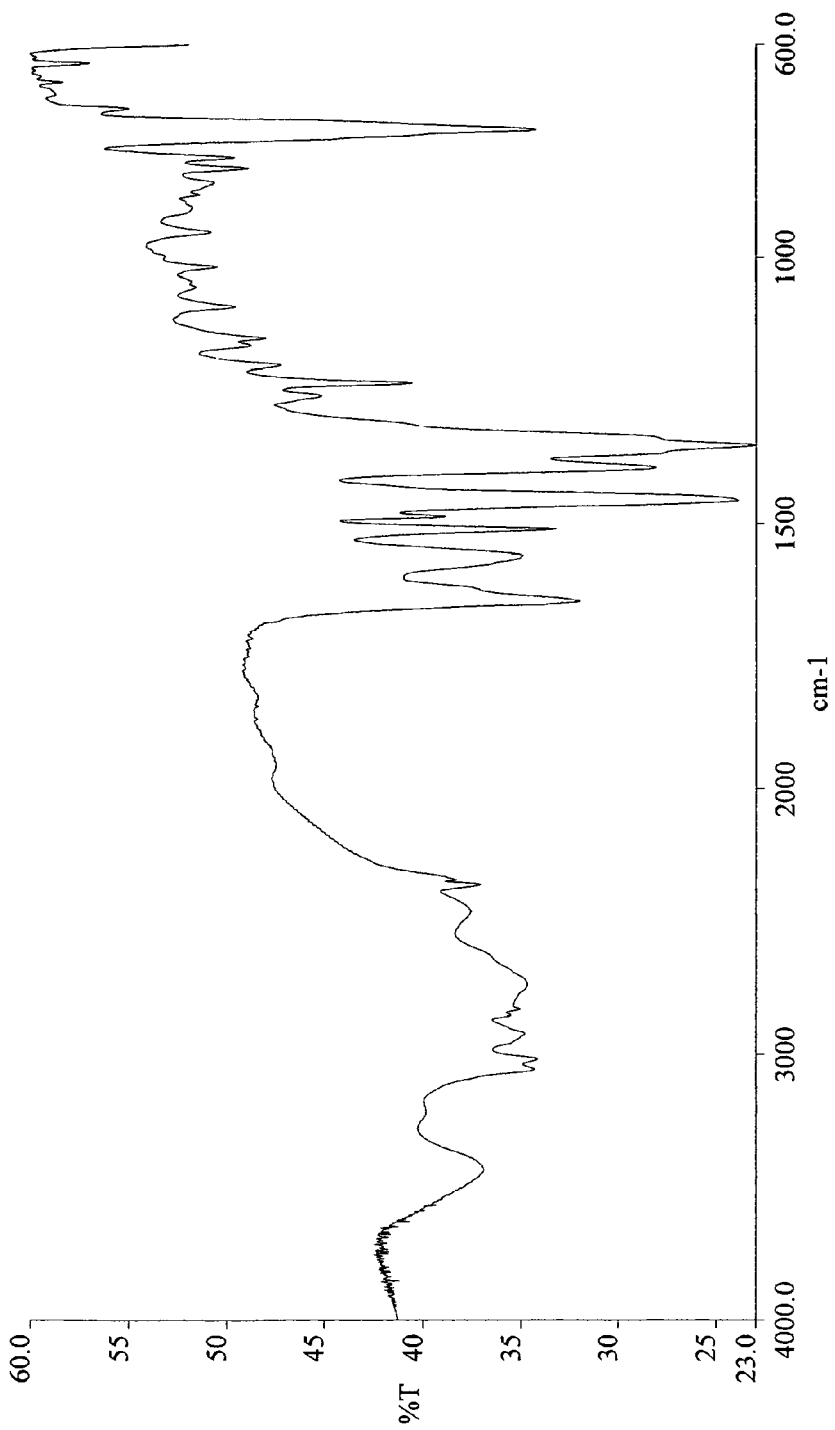
FIG. 12 is an FTIR spectrum of nortriptyline pamoate Form II.

An iso-propanol solution (45 mL) containing 1.0 g of nortriptyline pamoate (Form I prepared according to Example 4 above) was warmed to around 45-50° C. The resulting solution was held for approximately 30 minutes, then cooled to room temperature. The solution was poured into heptanes (400 mL) to precipitate the product. The solids were collected by filtration. The solid cake was washed with heptanes. The wet cake was dried at about 25° C. under vacuum to yield a solid (0.9 g). The material was characterized as its 2:1 pamoate salt and defined as Form II; DSC (FIG. 10) and FTIR (FIG. 12).

Example 6

Preparation of Imipramine Xinafoate

Figure 13:
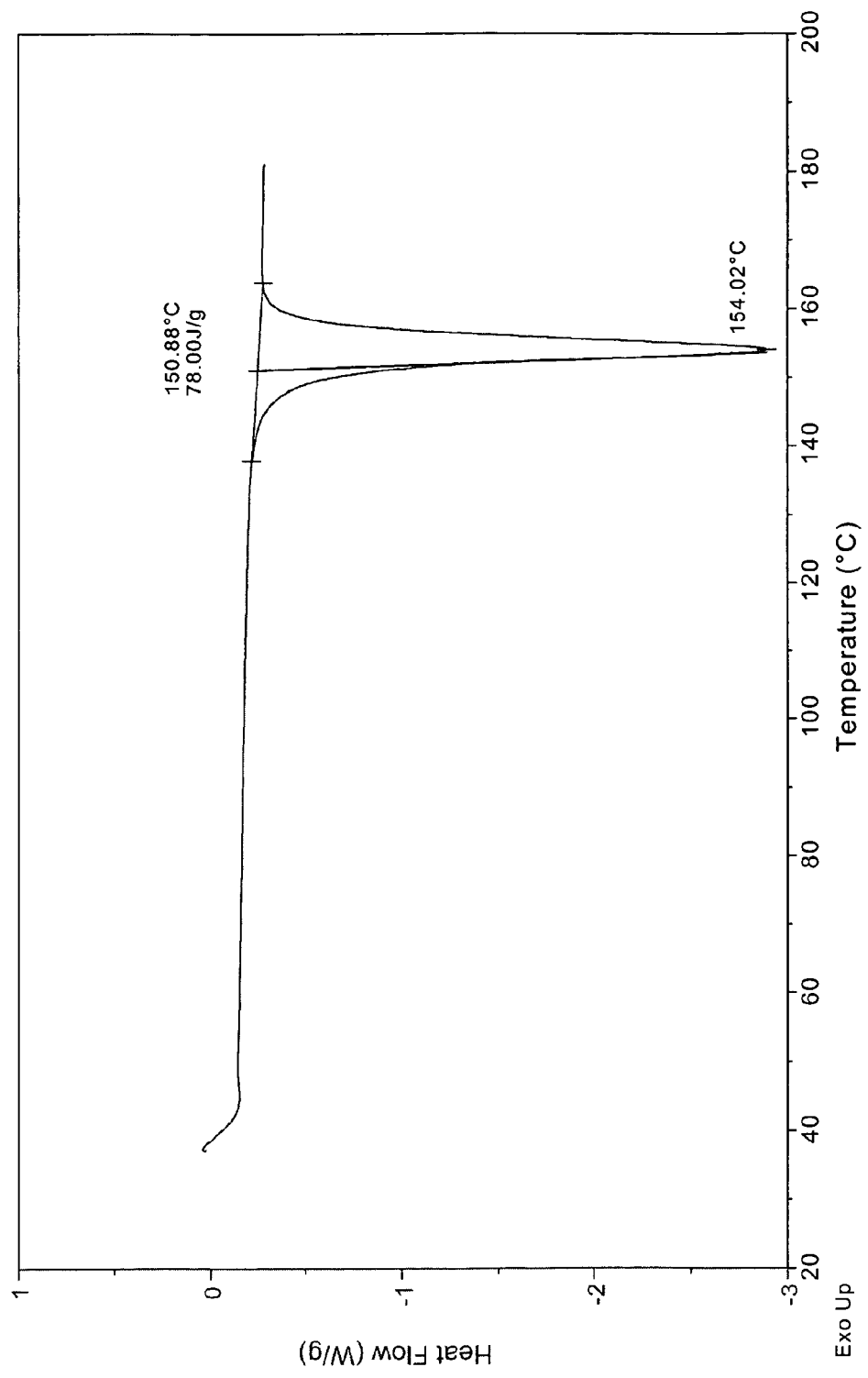
FIG. 13 is a DSC thermogram of imipramine xinafoate.
Figure 14:
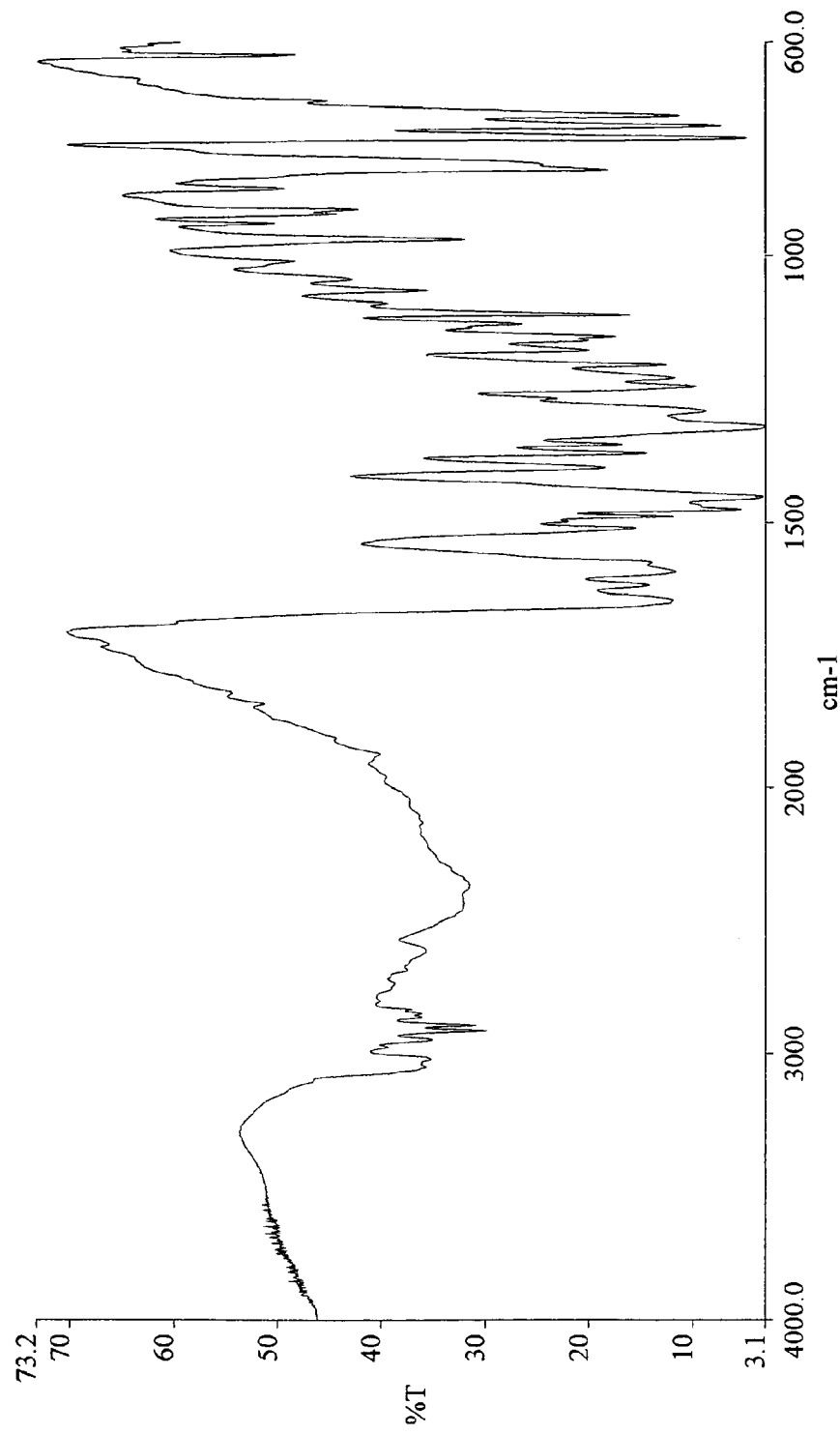
FIG. 14 is a FTIR spectrum of imipramine xinafoate.
Figure 15:
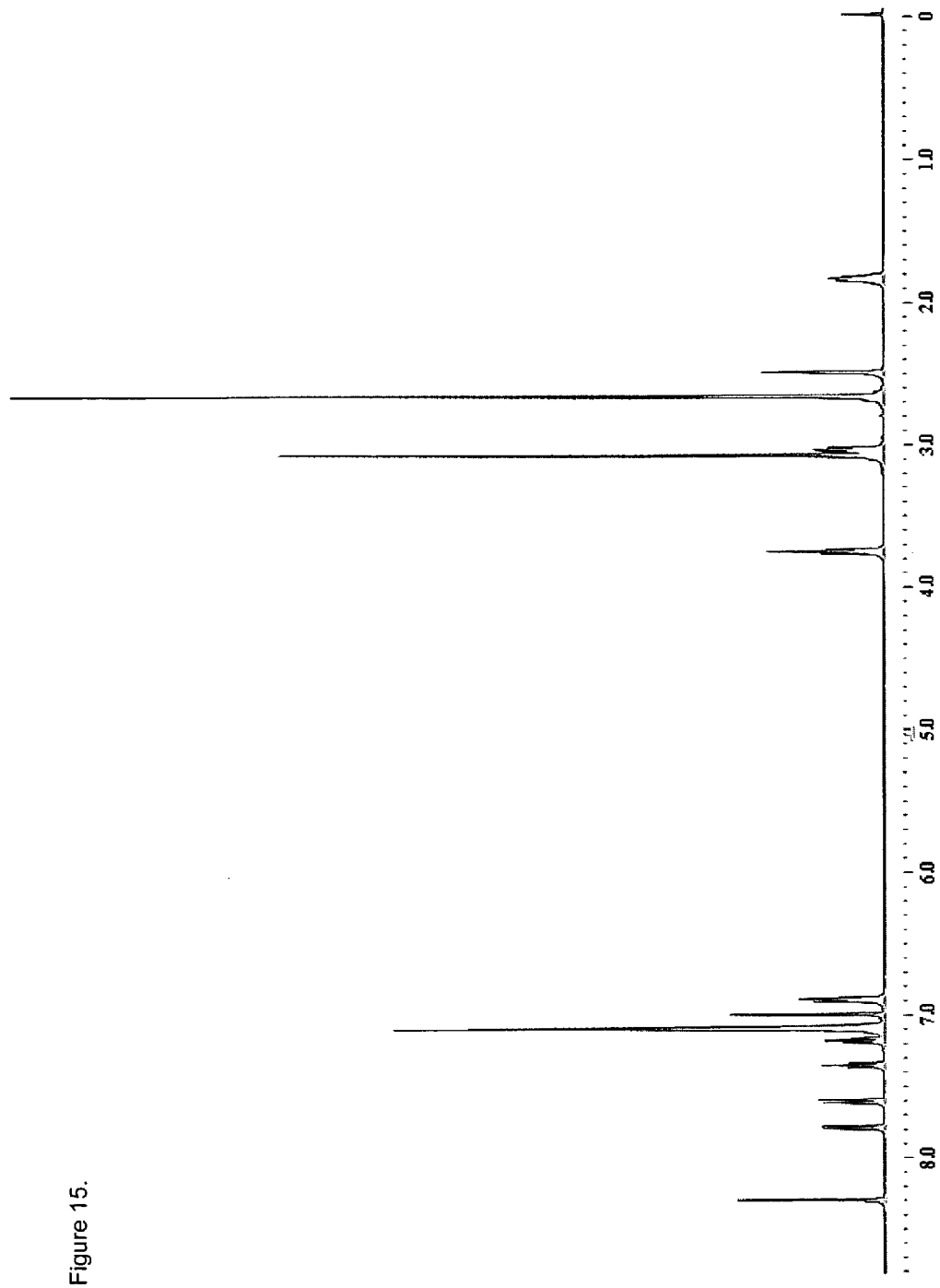
FIG. 15 is an $^1$H NMR spectrum of imipramine xinafoate.

To a solution containing 7.7 g of 3-hydroxy-2-naphoic acid in 75.0 g of USP water was added as necessary dilute HCl or NaOH solution to adjust the solution to about pH 9.4. To a second solution of 13.6 g of imipramine HCl in 100.0 g of USP water was added as necessary dilute HCl or NaOH solution to adjust the solution to about pH 4.5. The imipramine HCl solution was added to the 3-hydroxy-2-napthoic sodium salt solution over a period of about 2 h. The mixture was stirred and held at around 50° C. for approximately 18 h. The mixture was cooled to below about 25° C. and the solids were collected by filtration. The solid cake was washed with USP water (2×100 g). The solid cake was dried at about 105° C. under vacuum to yield a powder (12.7 g) and characterized by DSC (FIG. 13), FTIR (FIG. 14) and $^1$H NMR (FIG. 15).

Example 7

Preparation of Clomipramine Pamoate Form I

Figure 16:
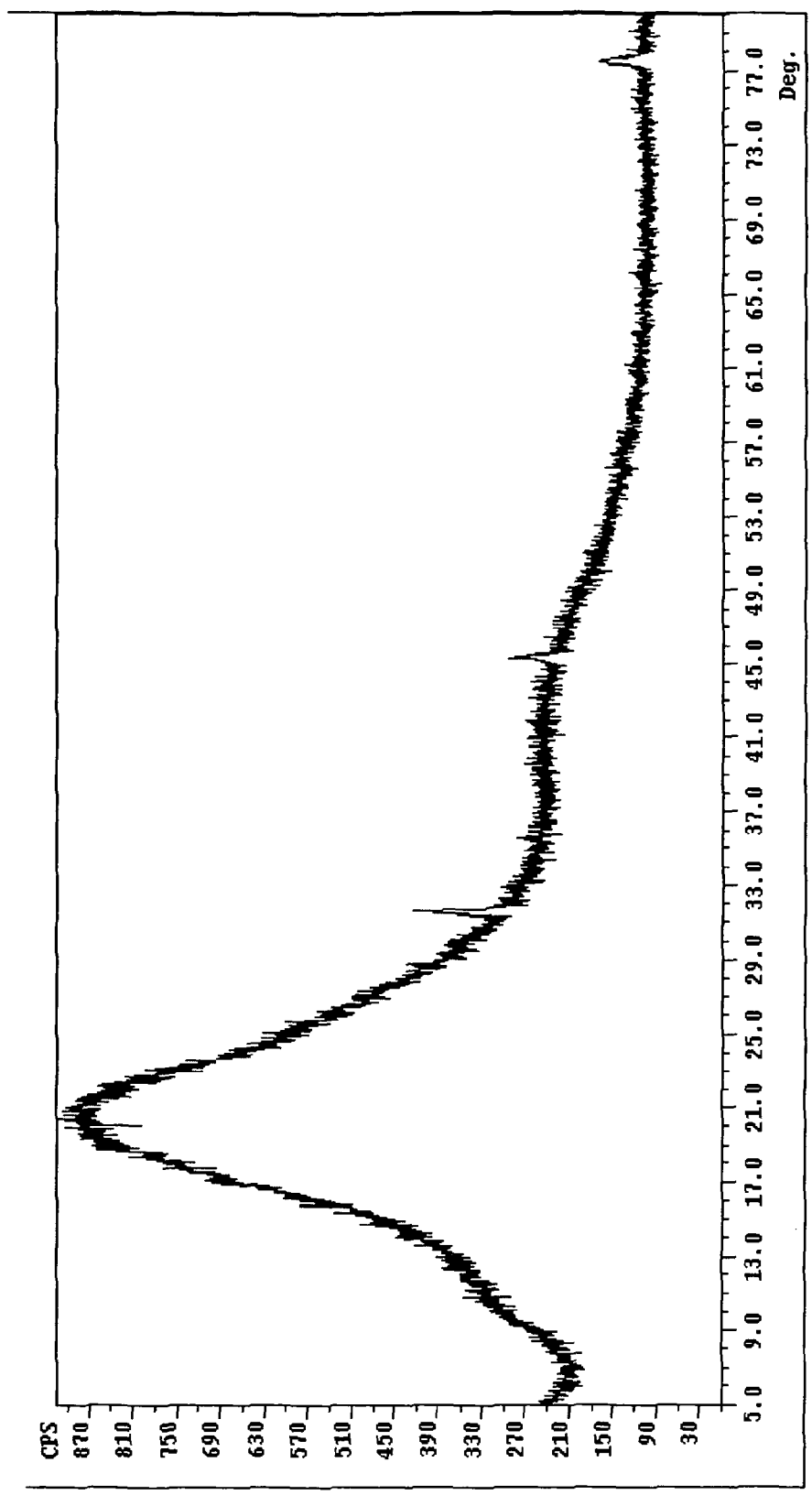
FIG. 16 is a PXRD diffractogram of clomipramine pamoate Form I.
Figure 18:
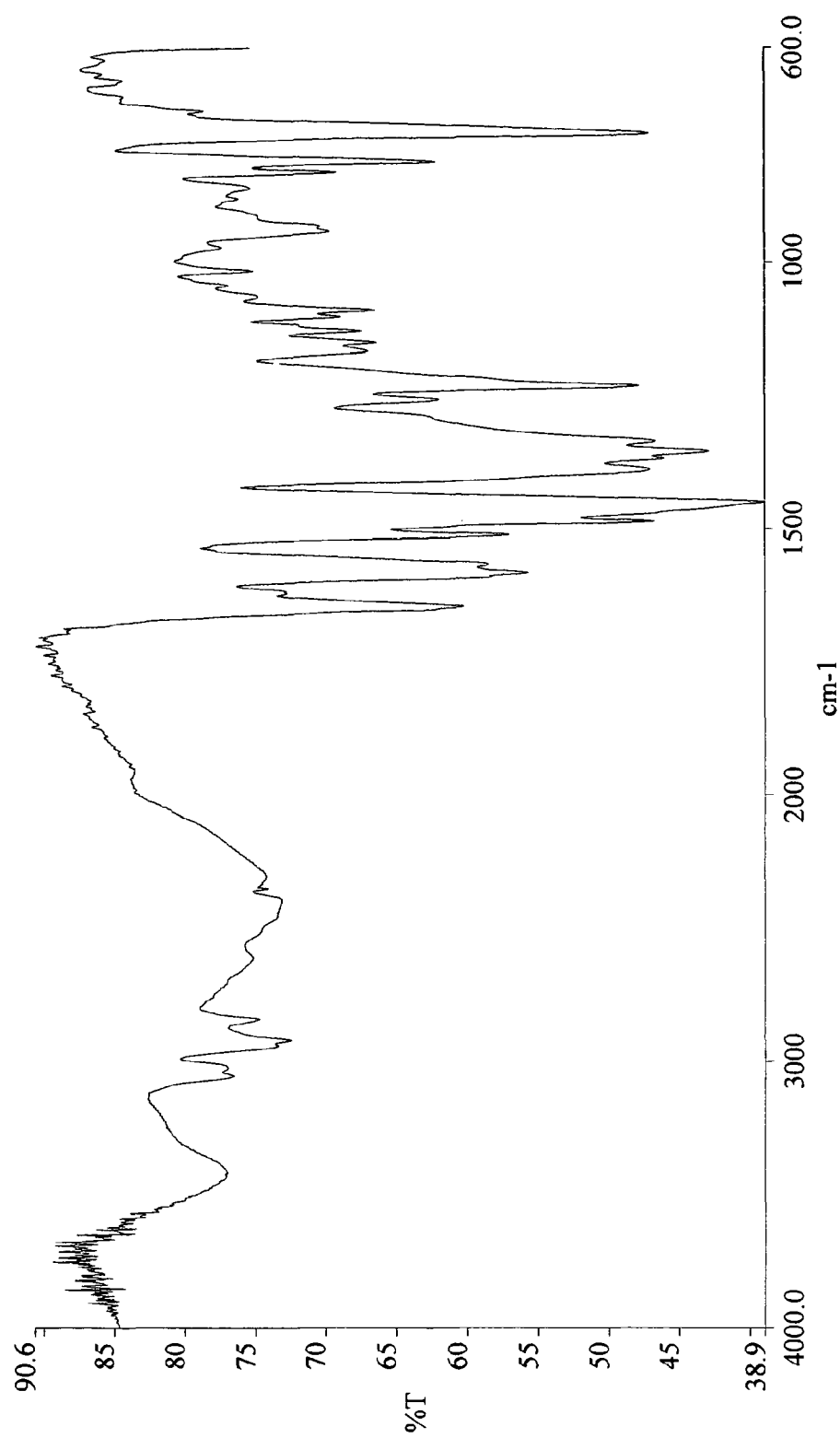
FIG. 18 is a FTIR spectrum of clomipramine pamoate Form I.
Figure 20:
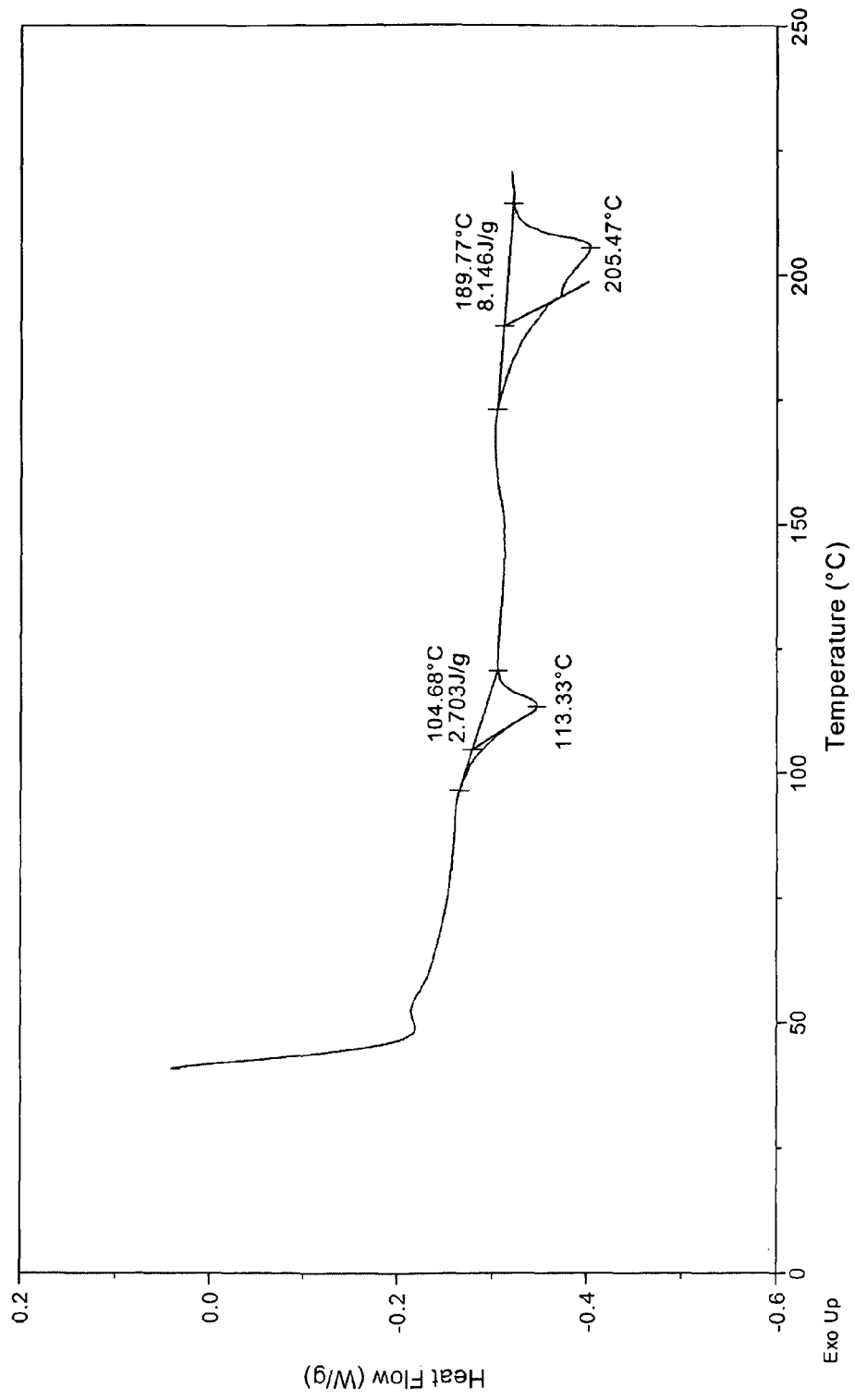
FIG. 20 is a DSC thermogram of clomipramine pamoate Form I.
Figure 22:
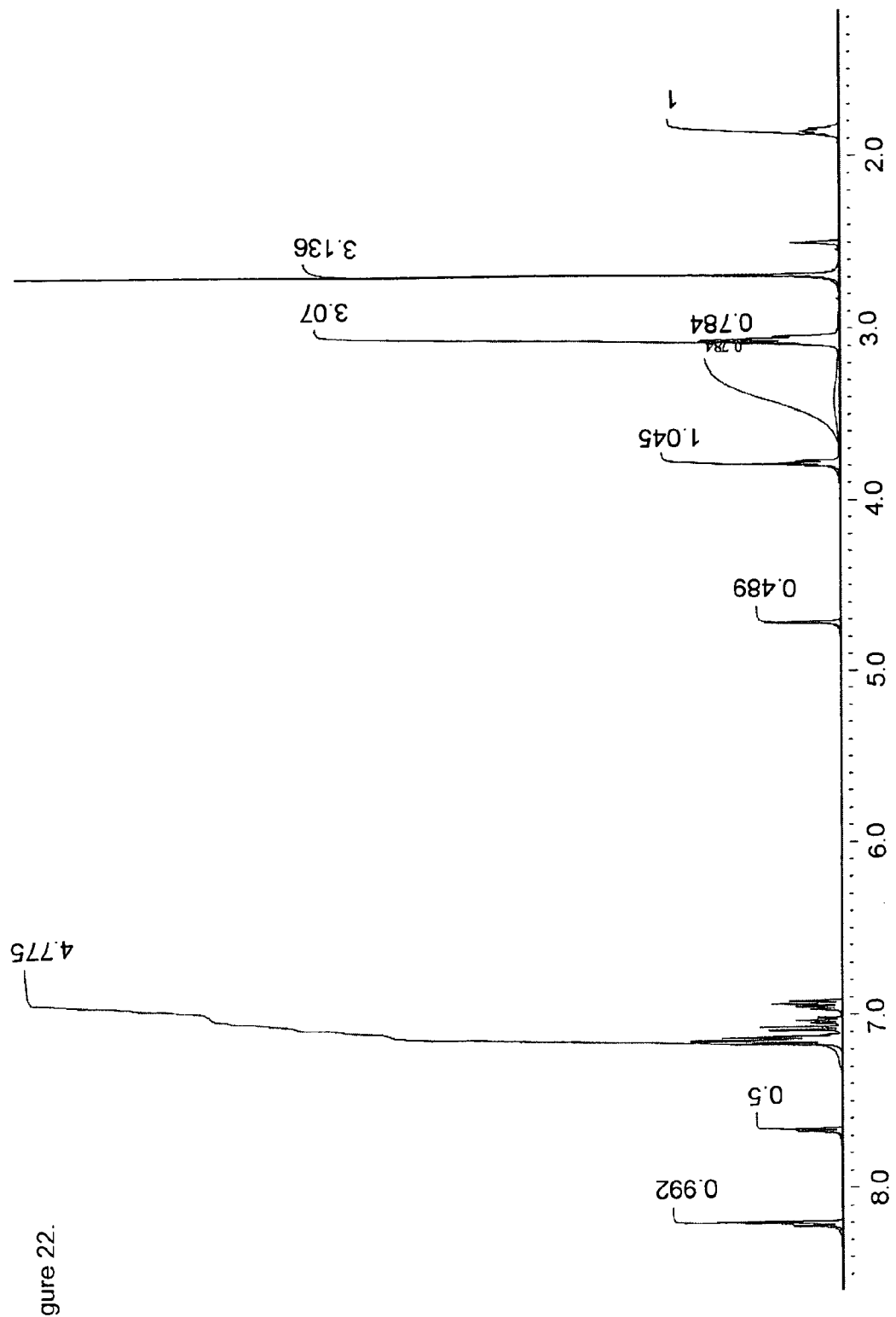
FIG. 22 is an $^1$H NMR spectrum of clomipramine pamoate Form I.
Figure 23:
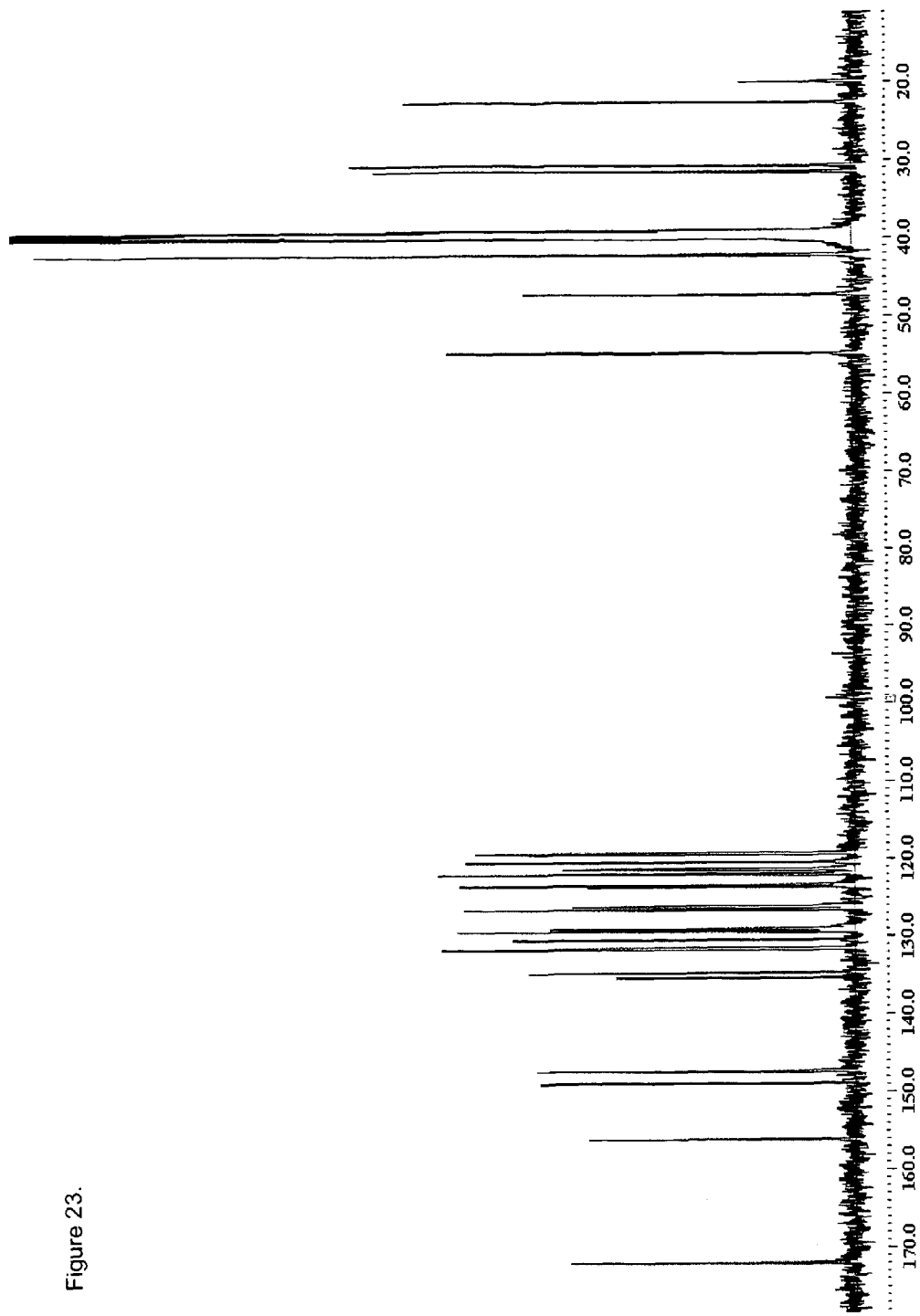
FIG. 23 is an $^{13}$C NMR spectrum of clomipramine pamoate Form I.

To a solution containing 2.83 g of disodium pamoate in 33.7 g of water was added a dilute HCl or NaOH solution to adjust the solution to about pH 9.4. To a second solution of 4.68 g of clomipramine HCl in 33.4 g of water was added dilute HCl or NaOH solution to adjust the solution to about pH 4.5. The clomipramine HCl solution was added to the disodium pamoate solution over a period of about 3 h. The mixture was stirred and held at about 30° C. for approximately 1 h. The mixture was cooled to below about 25° C. and the solids were collected by filtration. The solid cake was washed with water. The solid cake was dried at about 80° C. under vacuum to yield a powder (4.6 g). The material was characterized by 1H (FIG. 22) and 13 C (FIG. 23) NMR as the 2:1 pamoate salt. The material was defined as amorphous Form I by PXRD (FIG. 16), FTIR (FIG. 18) and DSC (FIG. 20).

Example 8

Figure 17:
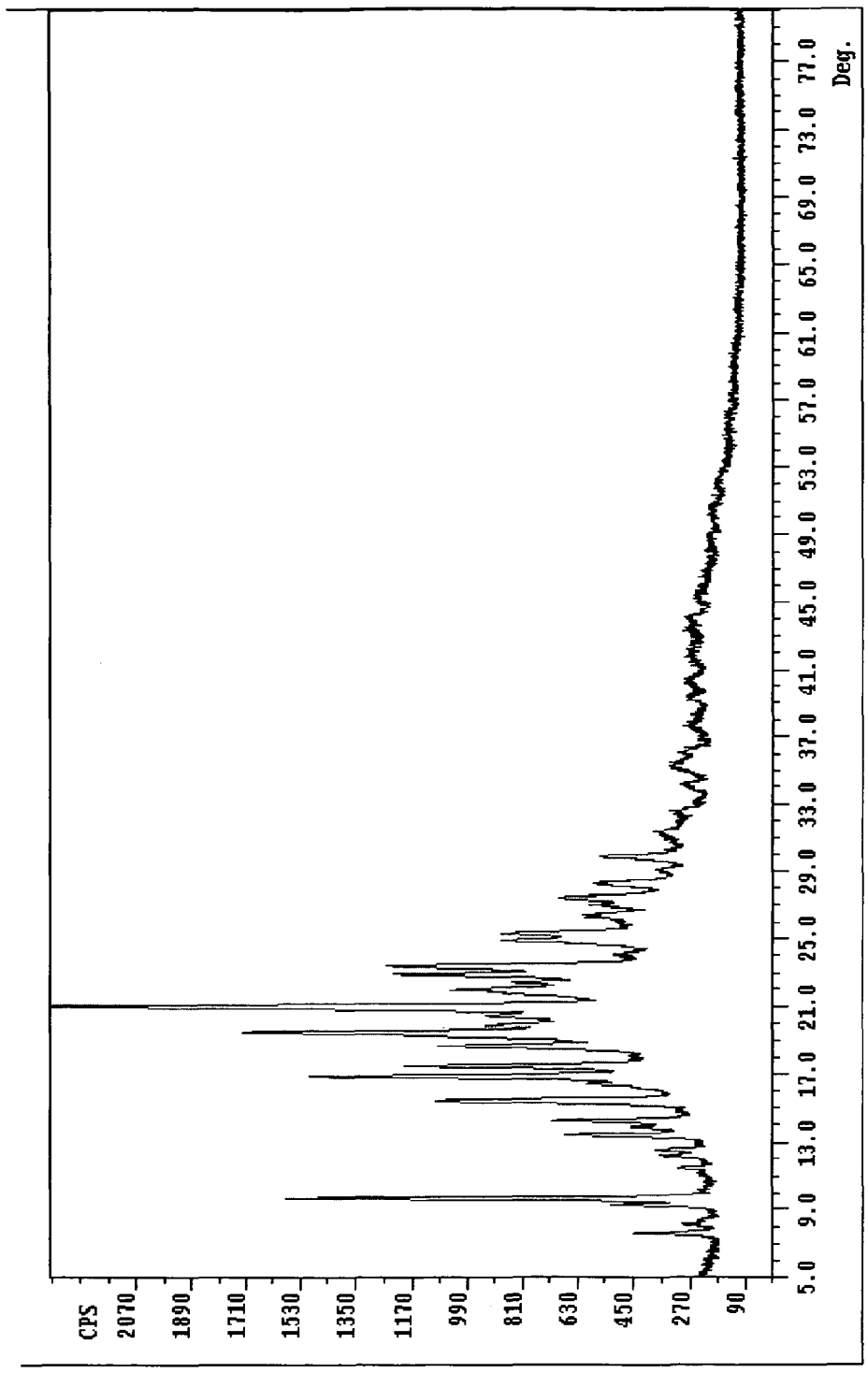
FIG. 17 is a PXRD diffractogram of clomipramine pamoate Form II.
Figure 19:
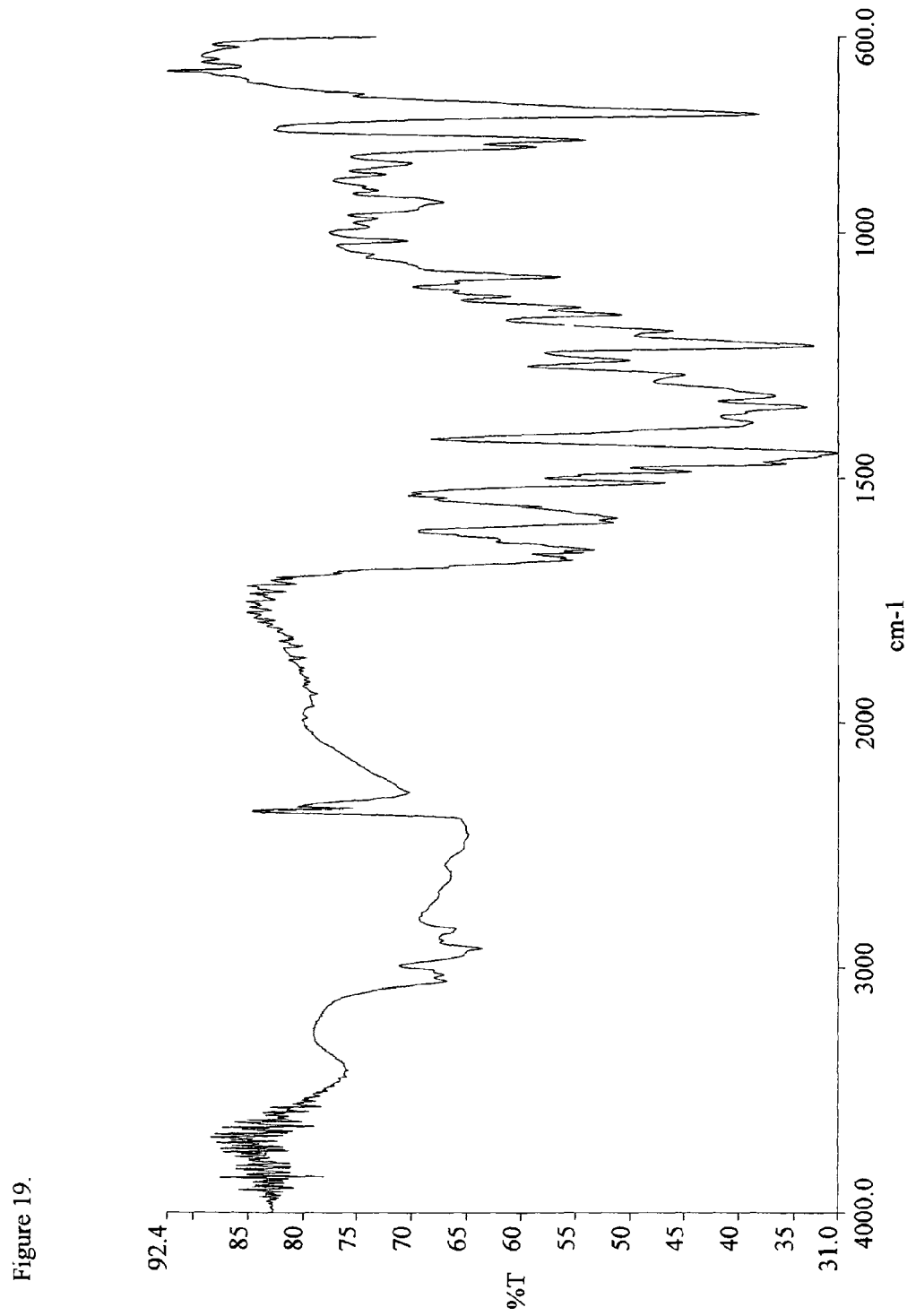
FIG. 19 is a FTIR spectrum of clomipramine pamoate Form II.
Figure 21:
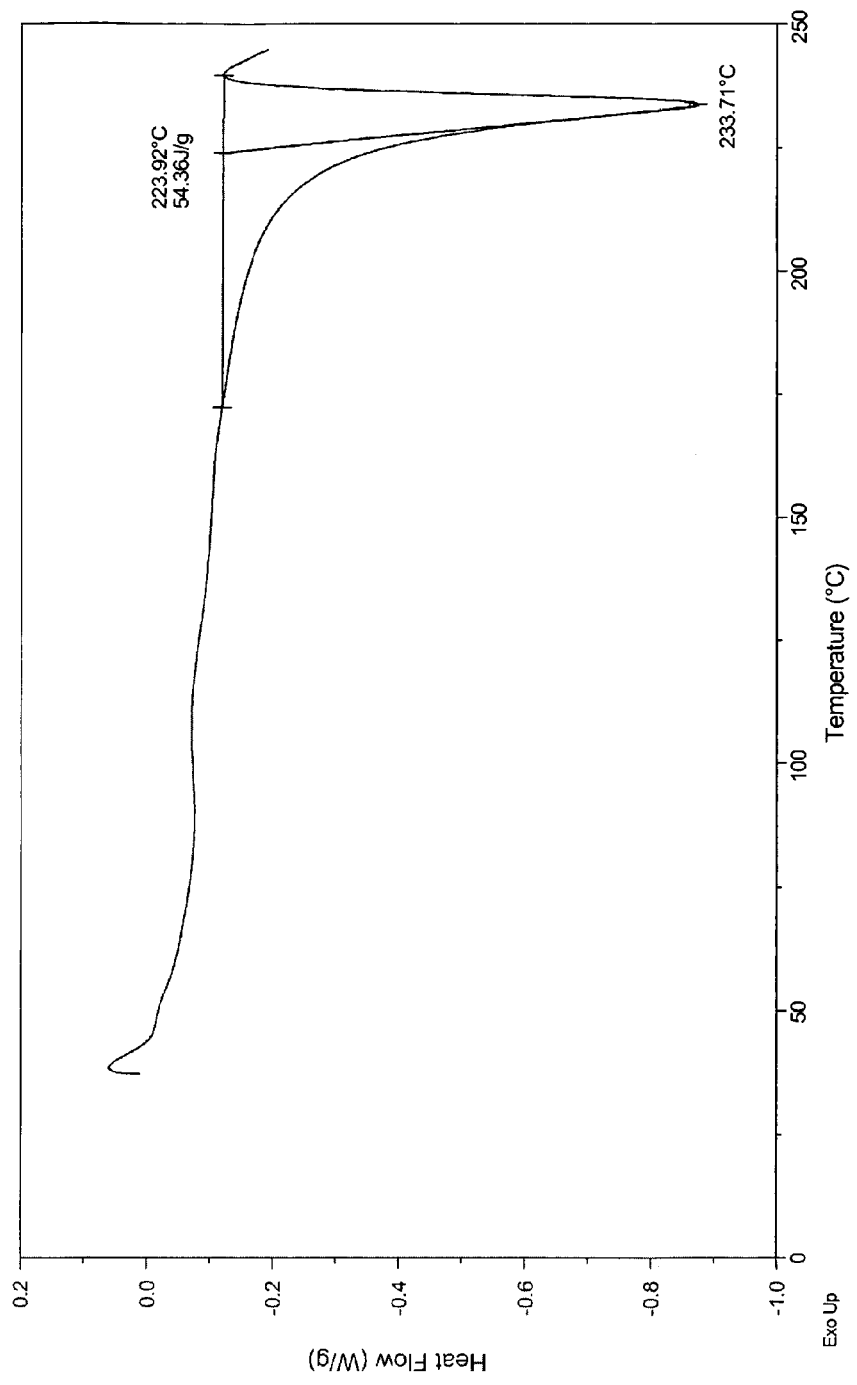
FIG. 21 is a DSC thermogram of clomipramine pamoate Form II.
Figure 24:
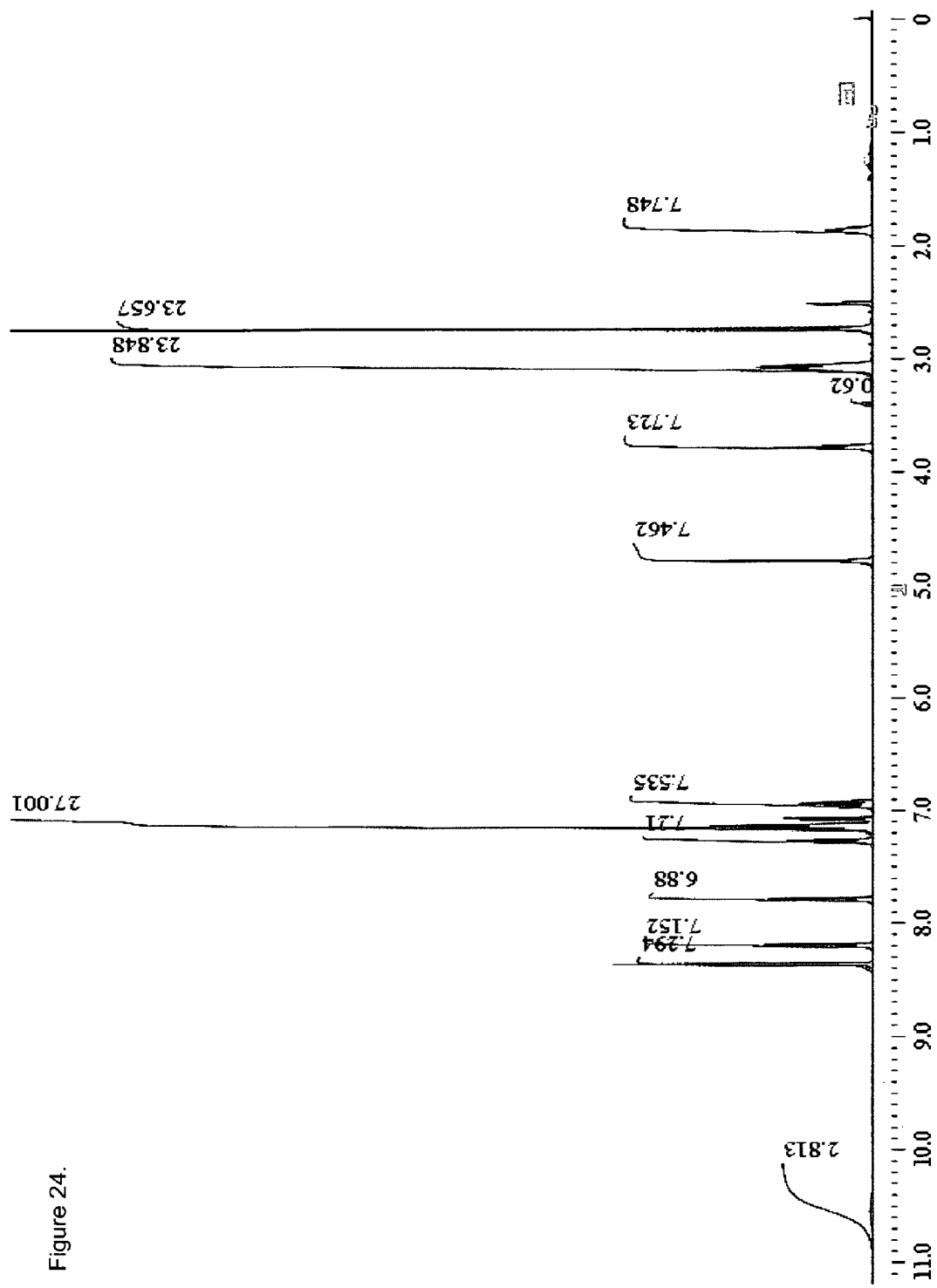
FIG. 24 is an $^1$H NMR spectrum of clomipramine pamoate Form II.
Figure 25:
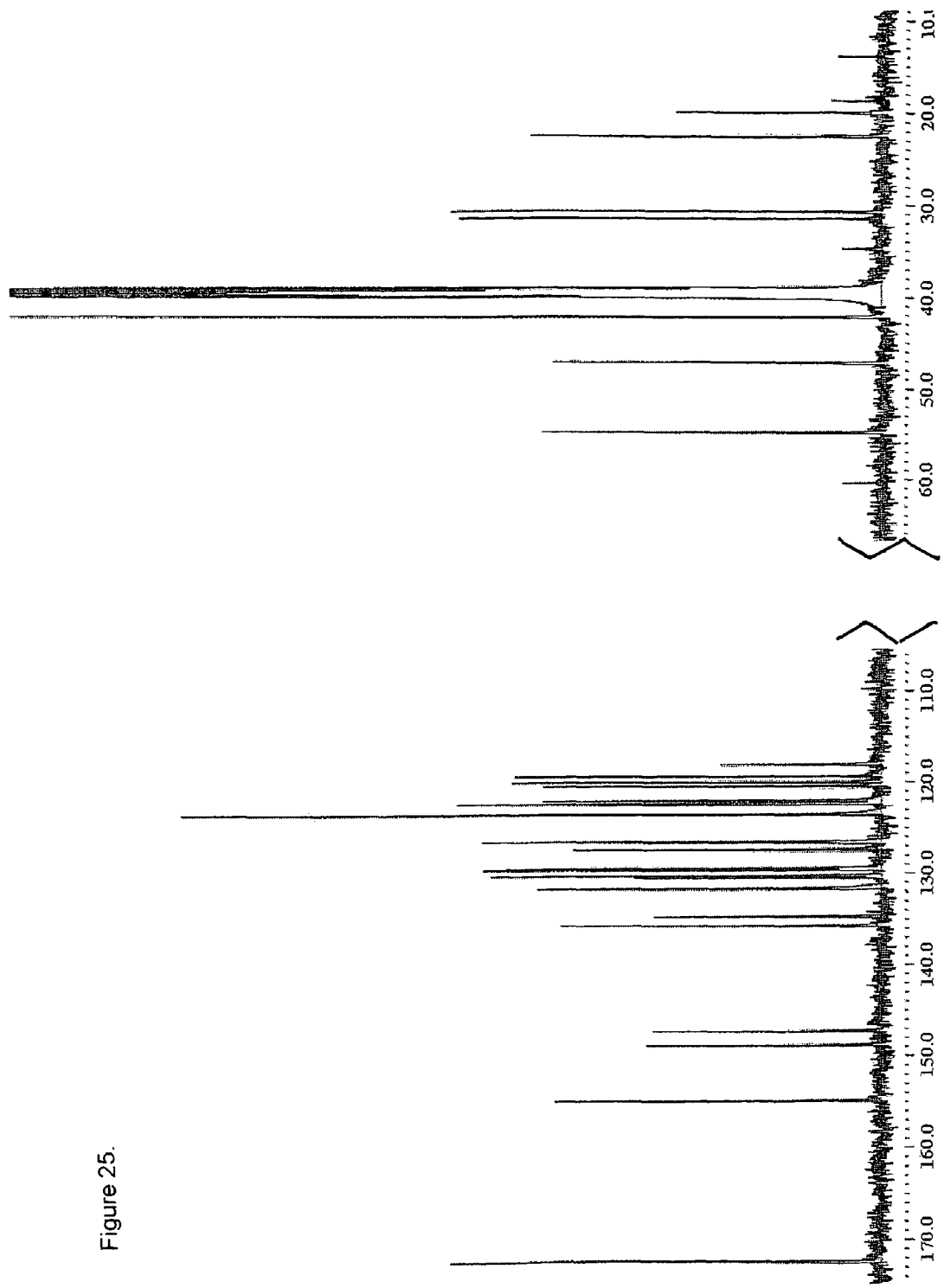
FIG. 25 is an $^{13}$C NMR spectrum of clomipramine pamoate Form II.

Preparation of Clomipramine Pamoate Form II 66.8 g of n-butanol was heated to about 40° C. and 1.0 g of clomipramine pamoate (Form I prepared according to the procedure described in Example 7 above) was added to the warm solvent. The mixture was stirred and heated at about 40° C. for approximately 1 h and then cooled to below about 25° C. The solids were collected by filtration and then dried at about 90° C. under vacuum to yield a powder (0.5 g). The material was characterized as the 1:1 pamoate salt according to $^1$H (FIG. 24) and $^{13}$C (FIG. 25) NMR. The material was defined as polymorphic Form II; PXRD (FIG. 17), FTIR (FIG. 19) and DSC (FIG. 21).

Example 9

Preparation of Promethazine Pamoate Form I and Form II

Figure 26:
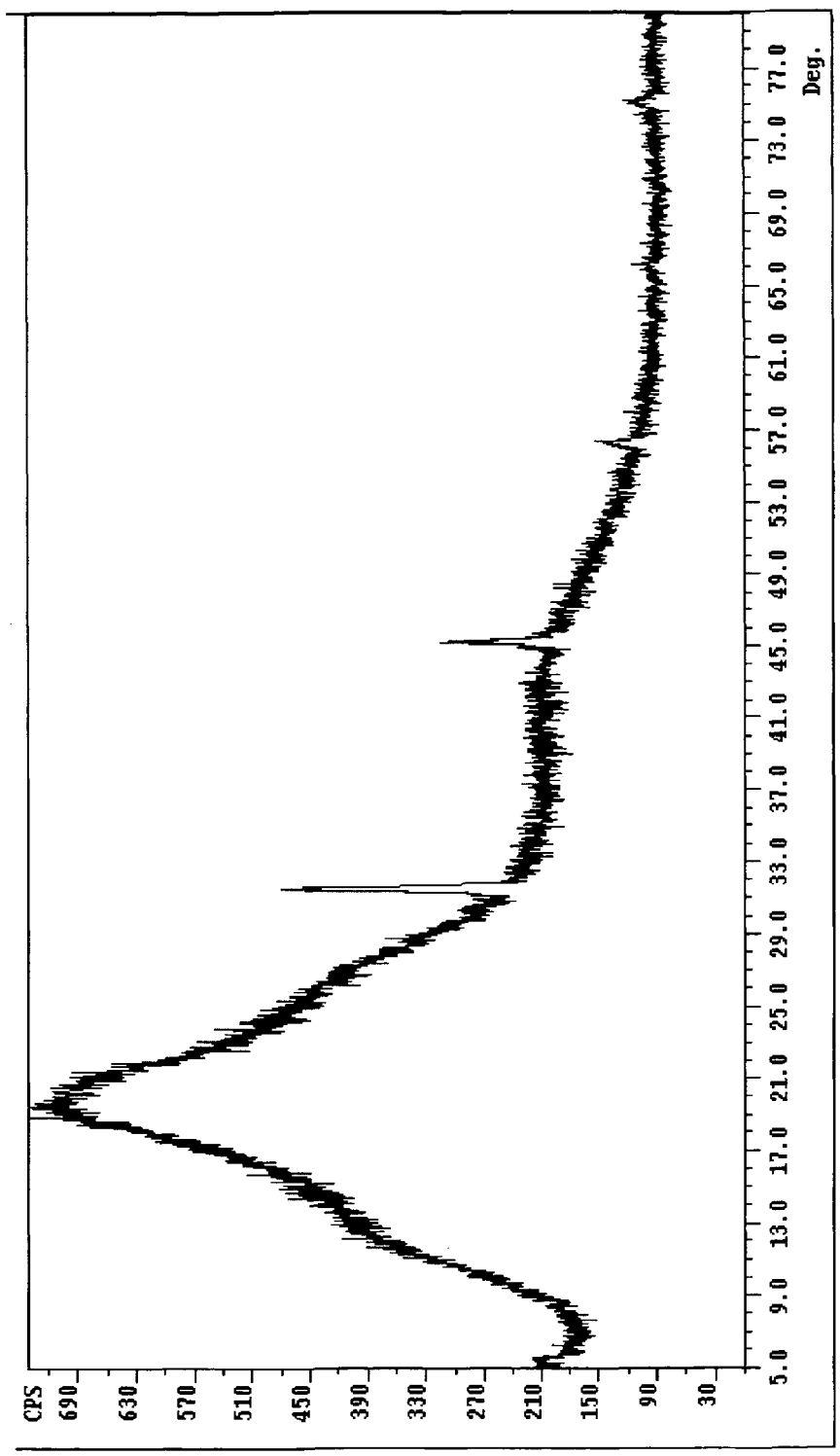
FIG. 26 is a PXRD diffractogram of promethazine pamoate Form I.
Figure 29:
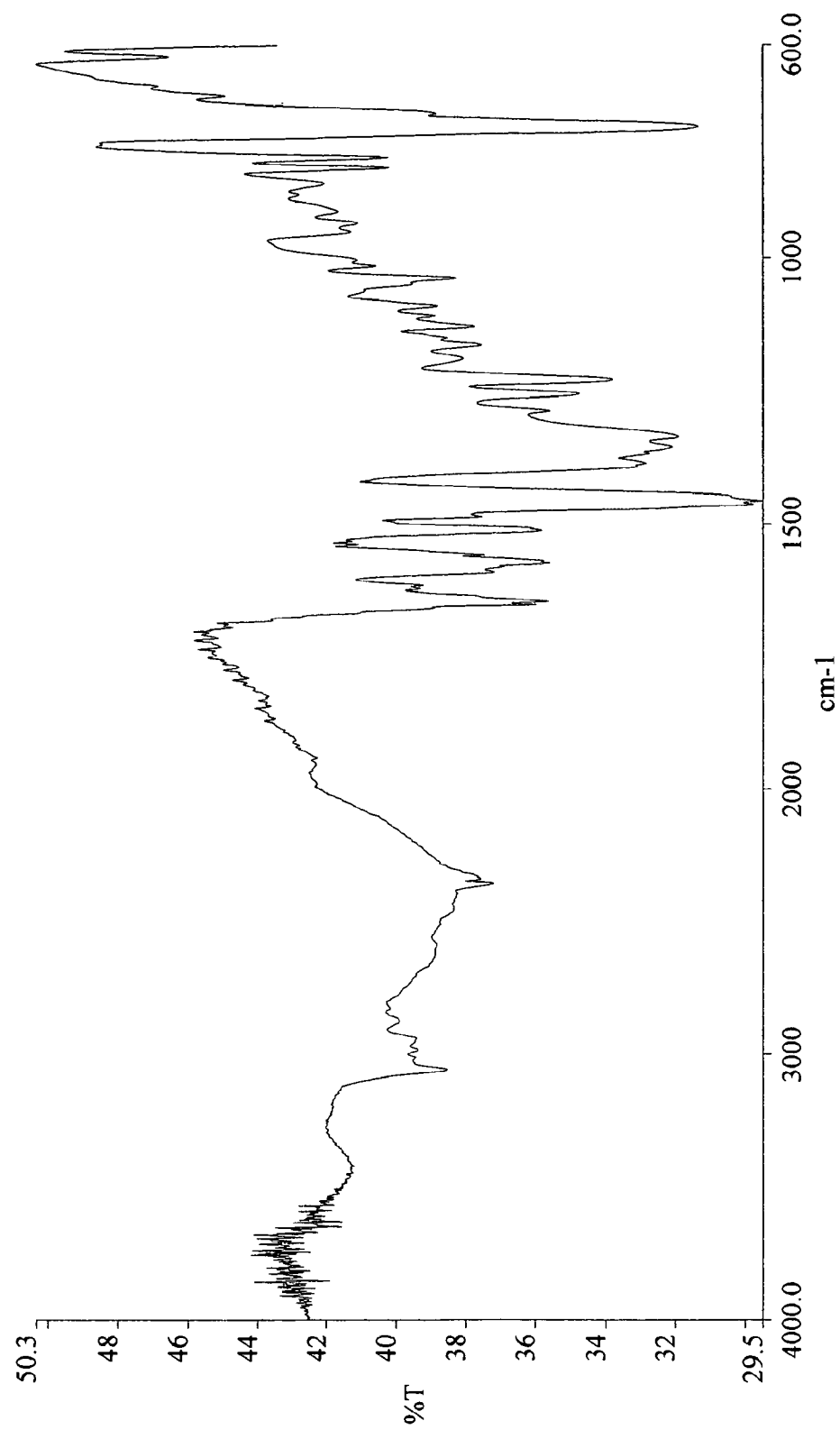
FIG. 29 is a FTIR spectrum of promethazine pamoate Form I.
Figure 32:
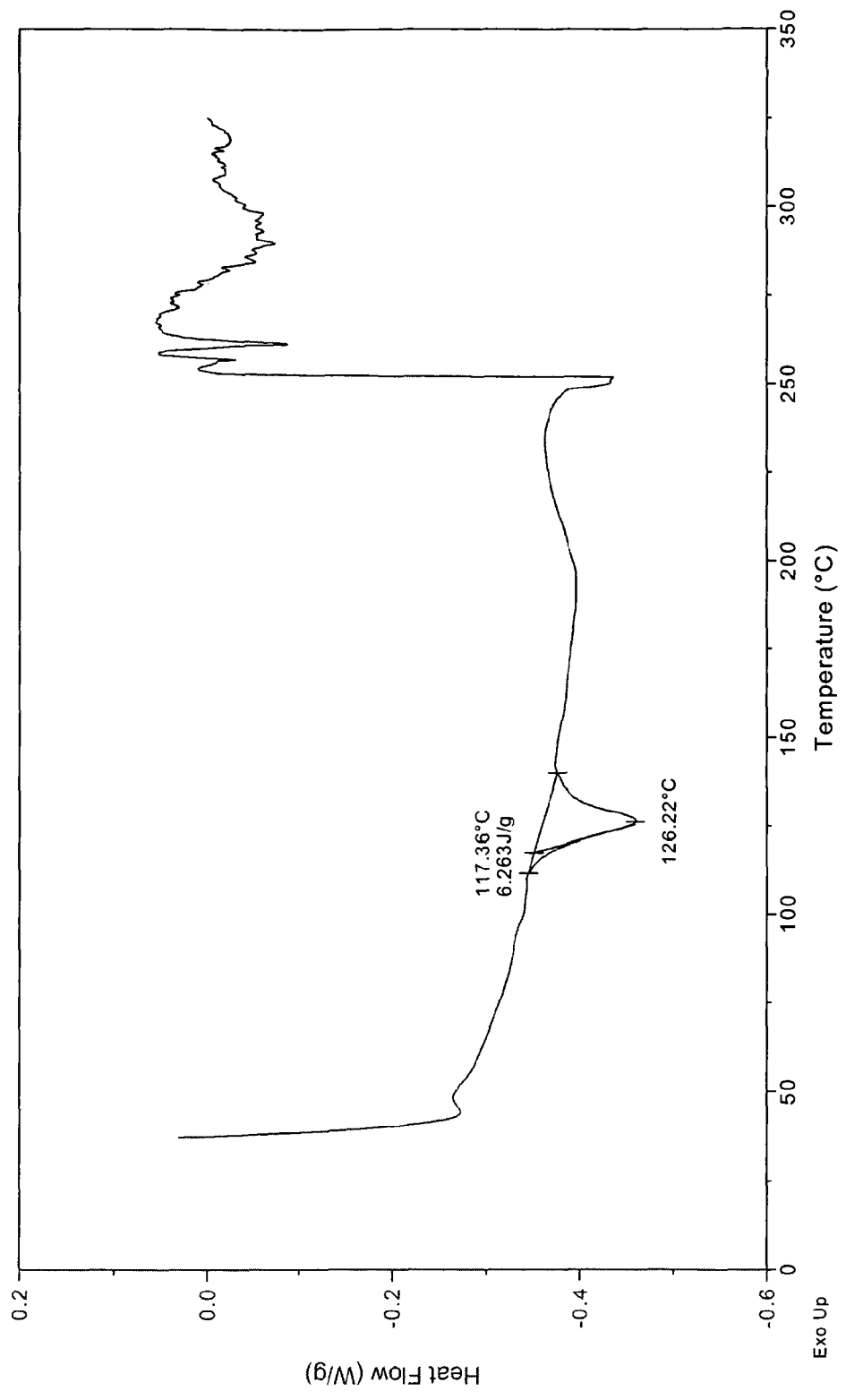
FIG. 32 is a DSC thermogram of promethazine pamoate Form I.

Disodium pamoate (36.20 g) was dissolved in USP water (420.0 g) and filtered to remove any residual particles. The filter was rinsed with USP water (2×15 g) and the filtrate was adjusted to about pH 9.5. Promethazine HCl (53.27 g) was dissolved in USP water (300.0 g). Any remaining residue was rinsed to the reactor with USP water (70.0 g) and the solution was adjusted to about pH 4.5. The promethazine HCl solution (426.2 g) was transferred to an addition funnel with a USP water rinse (10 g). The promethazine HCl solution was added to the disodium pamoate solution over approximately 2.5 h at about 26° C. After complete addition, the mixture was warmed slightly and a sample was taken at about 30° C. after approximately 15 min. The sample was collected by filtration, washed with USP water and dried (vacuum, about 85° C.) to provide promethazine pamoate Form I. The amorphous solid was characterized by PXRD (FIG. 26), FTIR (FIG. 29) and by DSC (FIG. 32).

Example 10

Preparation of Promethazine Pamoate Form II

Figure 27:
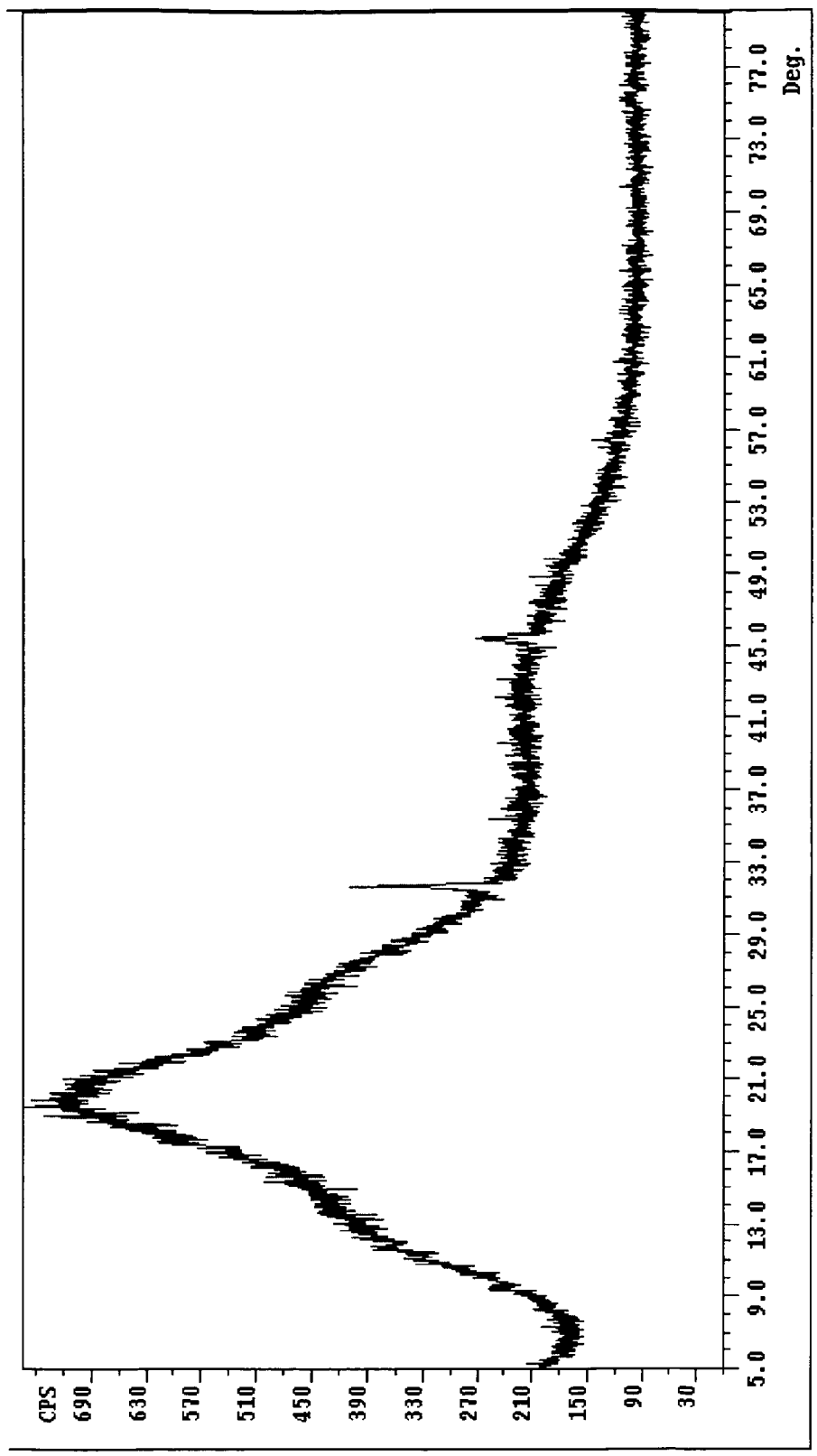
FIG. 27 is a PXRD diffractogram of promethazine pamoate Form II.
Figure 30:
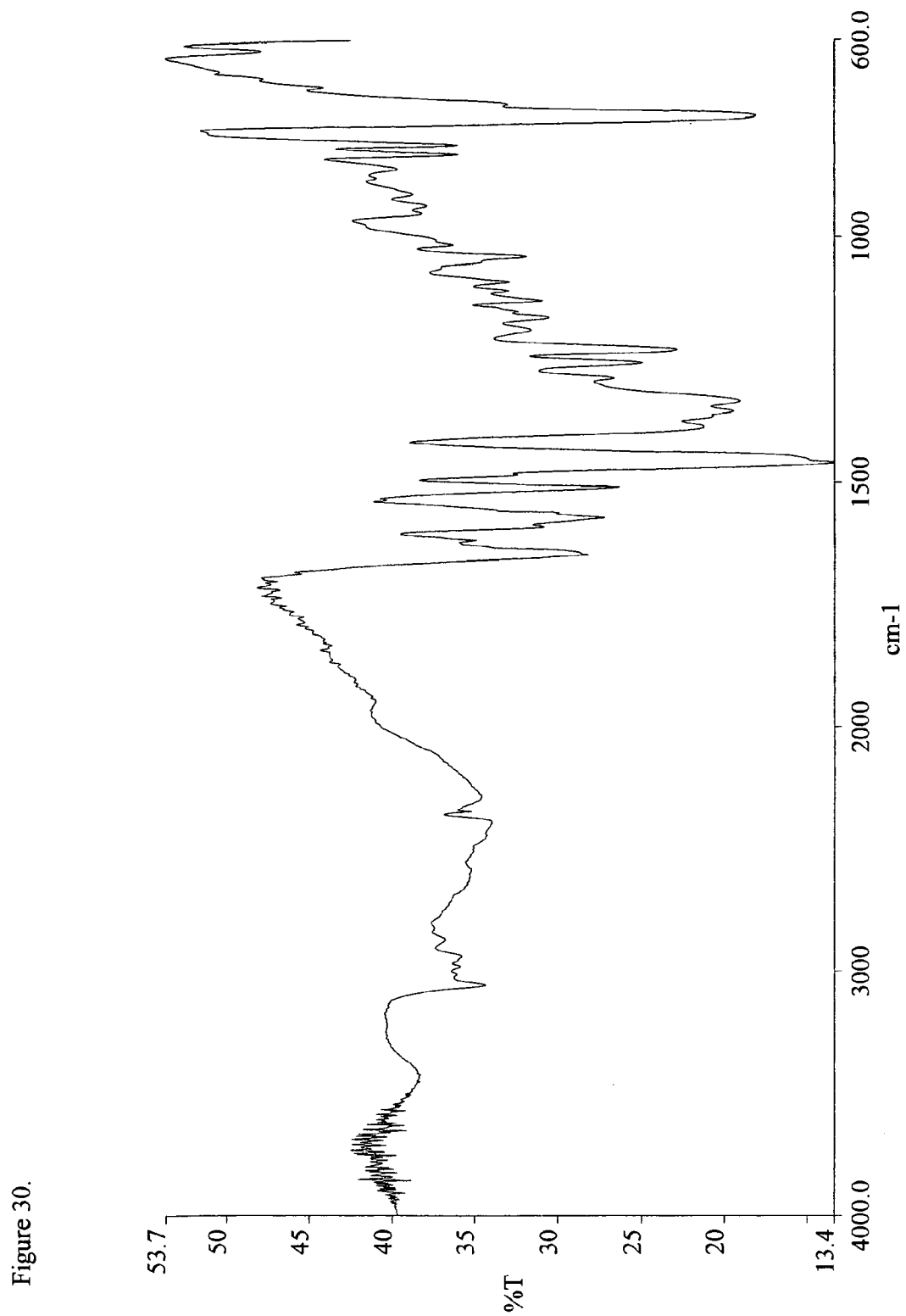
FIG. 30 is a FTIR spectrum of promethazine pamoate Form II.
Figure 33:
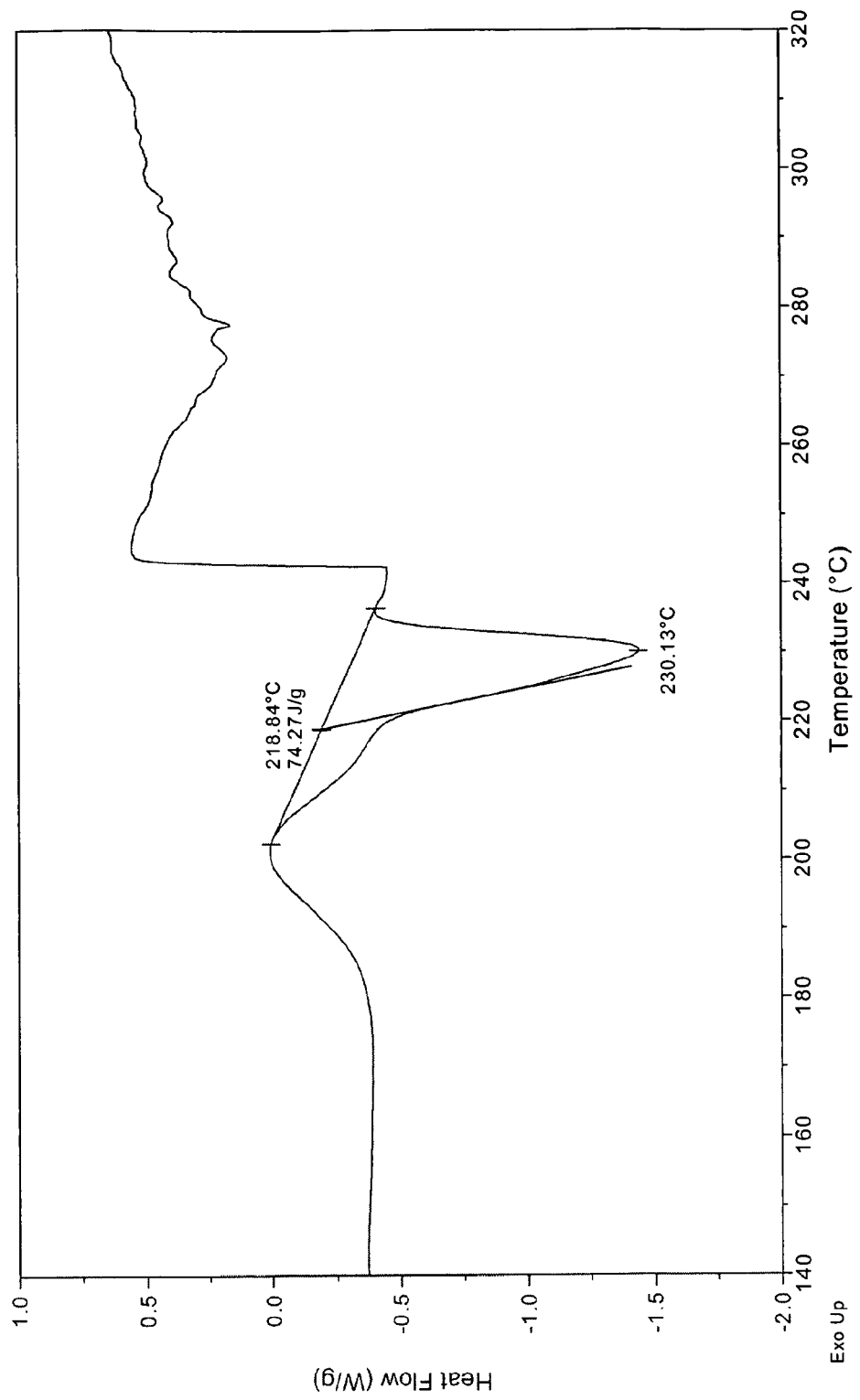
FIG. 33 is a DSC thermogram of promethazine pamoate Form II.

The remaining reaction mixture from Example 9 above was heated to about 53° C. and stirred for approximately 17 h. The reaction mixture was filtered and solids were washed with USP water and dried (vacuum, about 85° C.) to provide Form II. The solid was characterized by PXRD (FIG. 27), FTIR (FIG. 30), and DSC (FIG. 33).

Example 11

Preparation of Promethazine Pamoate Form III

Figure 28:
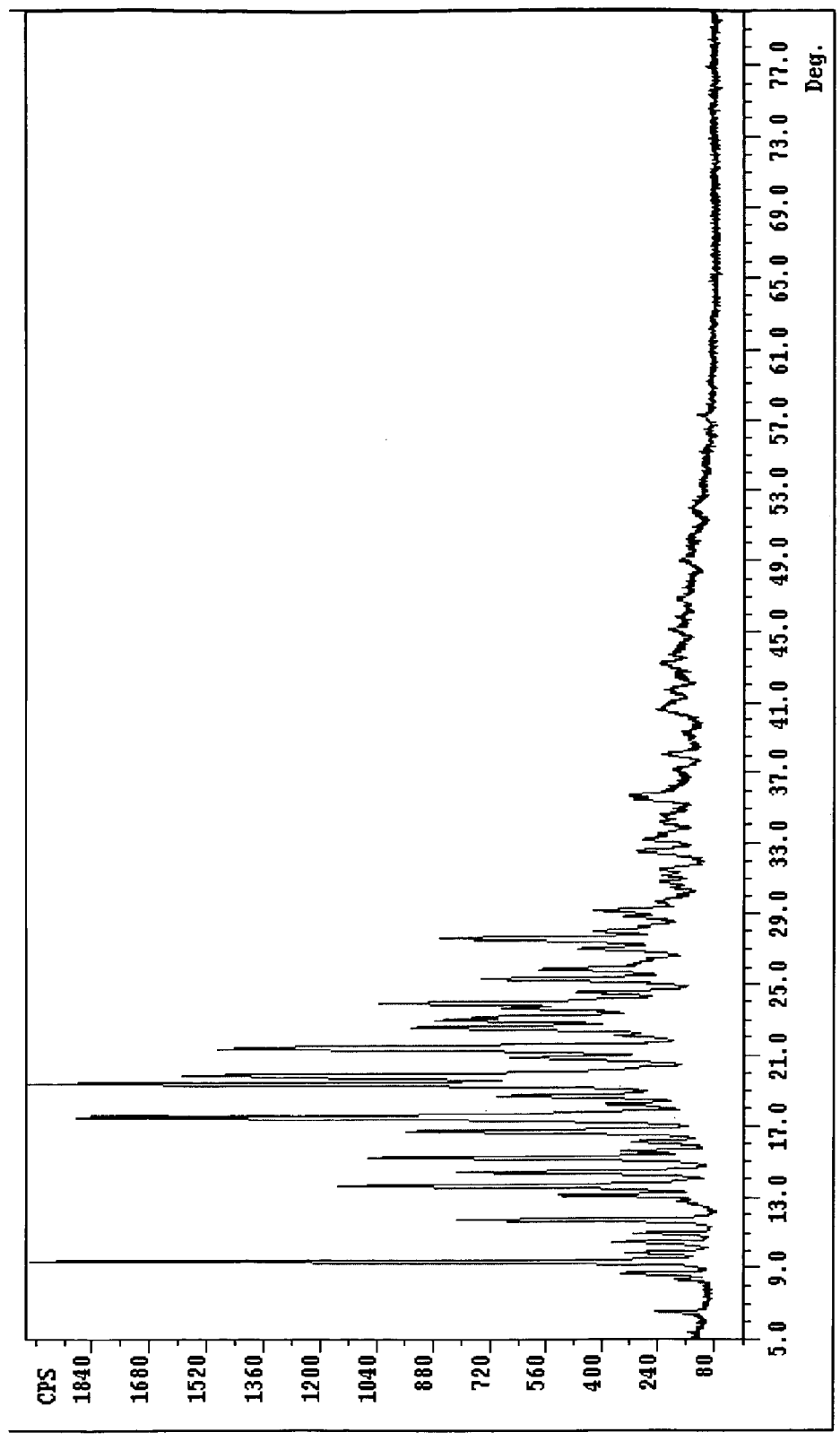
FIG. 28 is a PXRD diffractogram of promethazine pamoate Form III.
Figure 31:
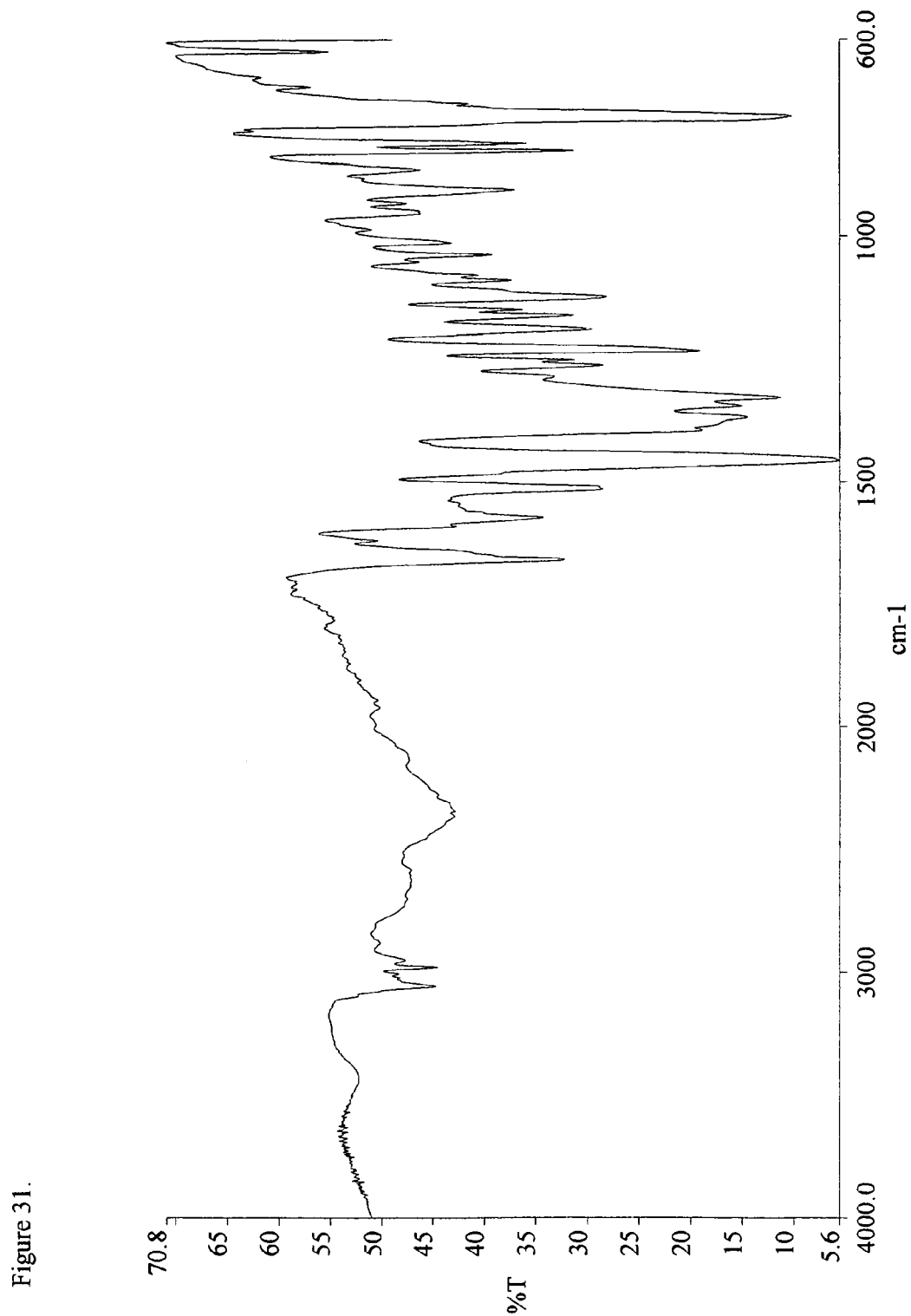
FIG. 31 is a FTIR spectrum of promethazine pamoate Form III.
Figure 34:
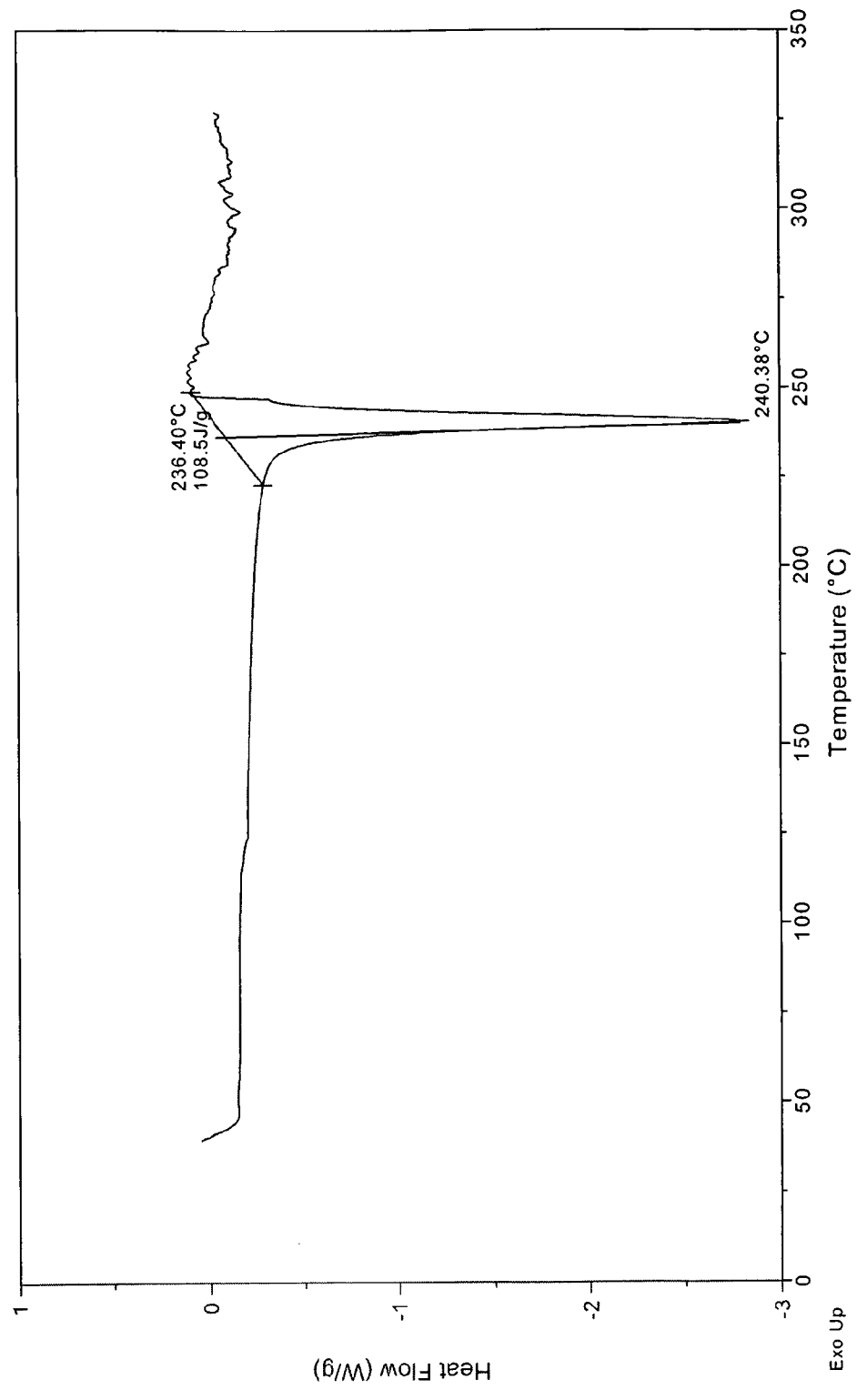
FIG. 34 is a DSC thermogram of promethazine pamoate Form III.
Figure 35:
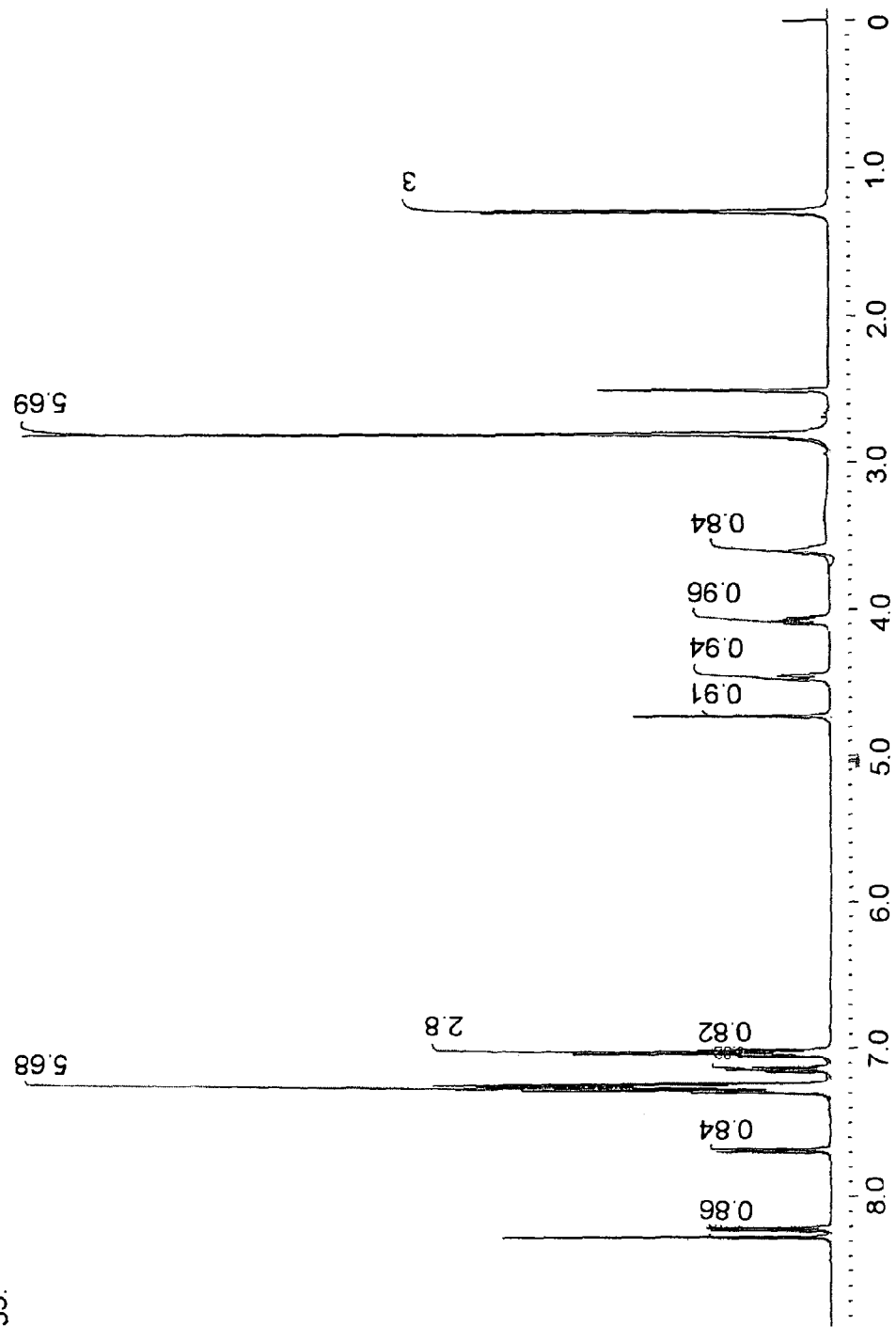
FIG. 35 is an $^1$H NMR spectrum of promethazine pamoate Form I.
Figure 36:
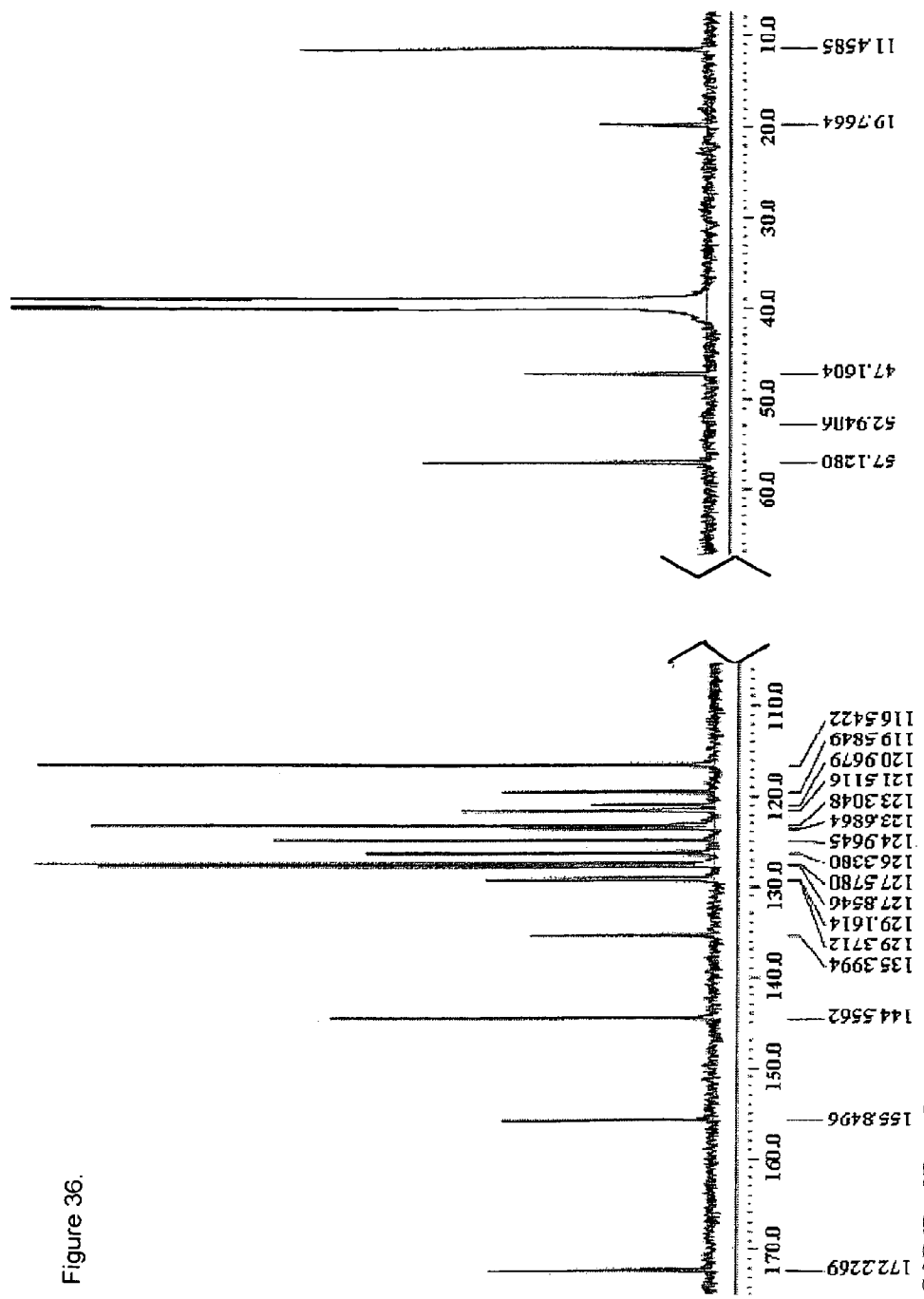
FIG. 36 is an $^{13}$C NMR spectrum of promethazine pamoate Form I.
Figure 37:
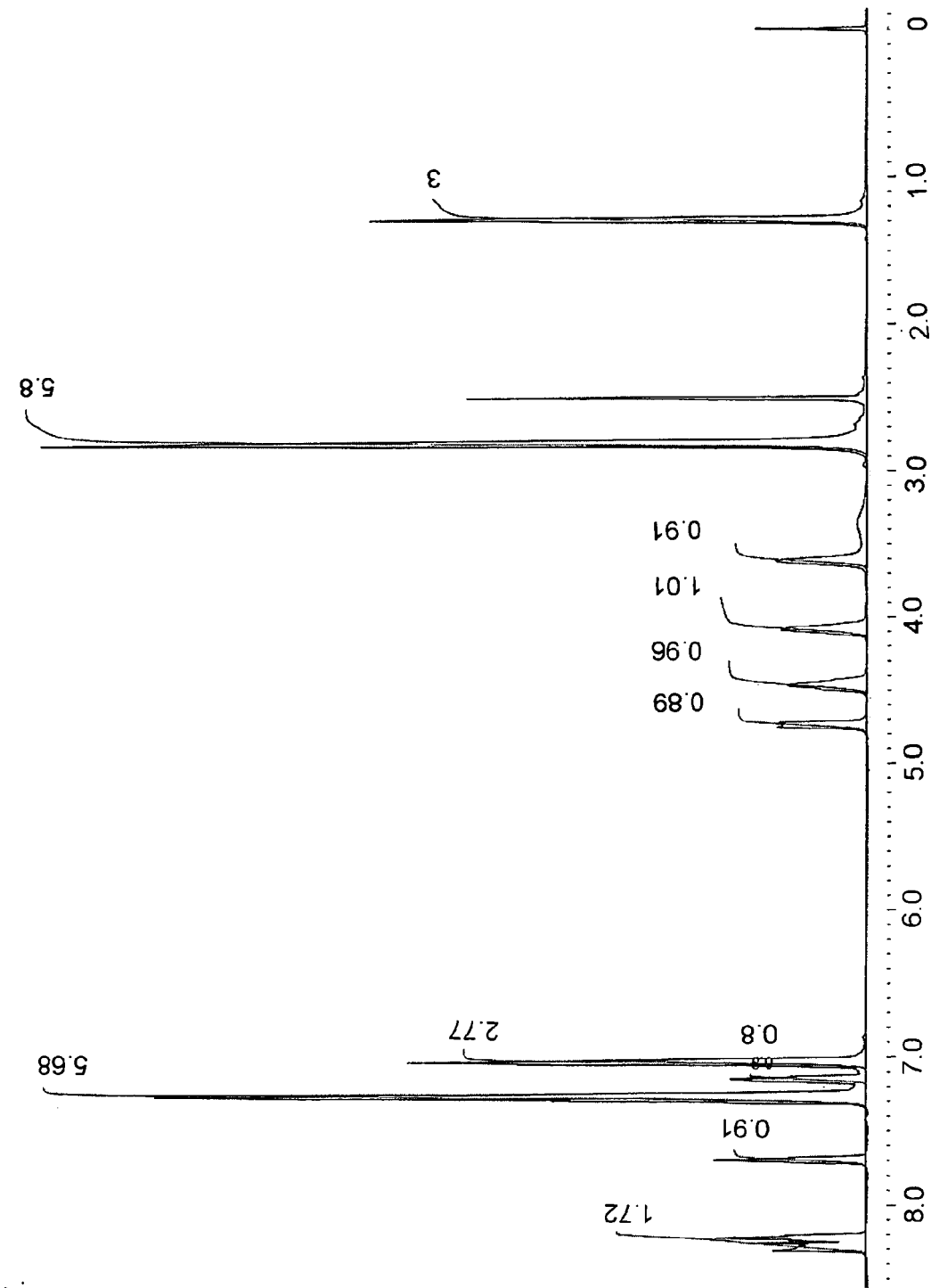
FIG. 37 is an $^1$H NMR spectrum of promethazine pamoate Form II.
Figure 38:
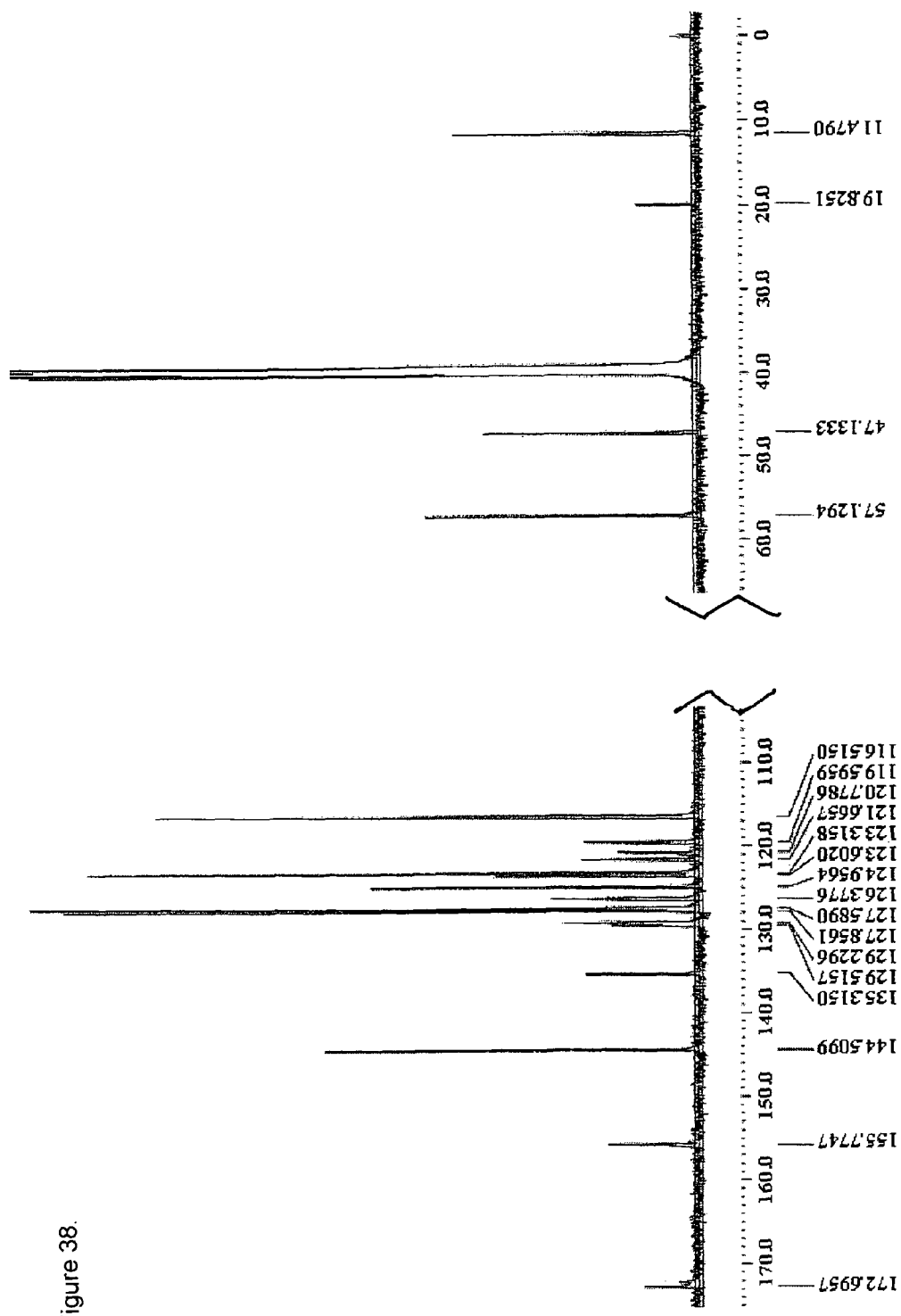
FIG. 38 is an $^{13}$C NMR spectrum of promethazine pamoate Form II.

Promethazine pamoate (46.1 g) was charged to an approximately 2% w/w mixture of ethanol-water (380 g). The residue was rinsed to the reactor with an approximately 2% w/w mixture ethanol-water (2×25 g). The mixture was heated from about 27° C. to about 77° C. over approximately 45 min. The mixture was heated at reflux for about 21 h. The mixture was cooled and filtered to collect solids. The reaction vessel was rinsed to the cake with ethanol (4×30 g). Solids (43.58 g) were dried on a Büchner funnel then transferred to a drying dish and placed in vacuum oven (about 50° C.). Promethazine pamoate Form III (43.38 g; 94%) was recovered. Form III was characterized by PXRD (FIG. 28), FTIR (FIG. 31) and DSC (FIG. 34).

Example 12

Preparation of Imipramine Salicylate

Imipramine salicylate was prepared and characterized according to example 8 found in co-pending United States patent application, 1234-56 entitled, "Salts of Physiologically Active and Psychoactive Alkaloids and Amines Simultaneously Exhibiting Bioavailability and Abuse Resistance".

Example 13

Dissolution Testing Procedure

The Distek Dissolution System was arranged in an Apparatus II configuration as per United States Pharmacopeia equilibrium solubility testing procedure USP <711> employing paddles and a 100 RPM spindle speed. The water bath temperature was set and controlled at 37±1° C.

The dissolution tests on drug pamoates, xinafoate, and salicylate were performed as separate experimental sets. Each experimental set was subjected to simulated gastric conditions by employing a standardized (and traceable) buffered 0.1N HCl solution supplied by VWR.

Each test sample was filled into a clear gelatin capsule (Capsuline Size "2"). The pharmaceutical grade gelatin capsules are derived from bovine raw materials from BSE-free countries. The gelatin is 100% HIDE gelatin. A wire (~1.7-2.0 g) was coiled around each capsule to assure the capsule did not float in the test medium. The amount of each API filled into an individual capsule was determined based on twice the highest unit dose available for a commercialized drug product.

Prior to use, the 0.1N HCl solution was warmed to 38-42° C. with adequate stirring and then degassed for 30 minutes with helium passed through a sparge stone attached to Tygon tubing. The degassed buffered solution was dispensed into each of five dissolution vessels (500 mL/vessel) using a volumetric flask. The vessels were immersed in the constant temperature bath and allowed to reach thermal equilibrium (37±1° C.). A single capsule (with wire weighting) and containing a specified drug salt was then added to each vessel, the paddles and spindles lowered into the solution and agitation initiated at 100 RPM. The covers with sampling ports were then placed on each vessel. Sampling was performed at regular time intervals on each vessel using a sampling syringe dedicated to each vessel. At each sampling time point about 10 mL of solution was removed from the vessel and filled into a test vial for HPLC analysis.

Example 10

Dissolution Monitoring by HPLC

Drug dissolution assays at specified time intervals were determined by a high pressure liquid chromatography (HPLC) method employing a Waters Atlantis column (dC18, 5 micron, 4.6×150 mm), or equivalent. The HPLC system was a Waters 2695 HPLC system equipped with a Waters 2996 photo diode array detector (detection wavelength: 265 nm extracted; 215 nm extracted). The eluant consisted of mobile phase A (0.1% TFA in water) and mobile phase B (acetonitrile). The gradient elution conditions were as tabulated below.

| Gradient Elution Table | | | |
|---|---|---|---|
| | Time min | % A | % B |
| 1 | | 80 | 20 |
| 2 | 6.00 | 80 | 20 |
| 3 | 10.00 | 52.00 | 48.00 |
| 4 | 25.00 | 52.00 | 48.00 |
| 5 | 25.10 | 80 | 20 |
| 6 | 33.00 | 80 | 20 |

The drug hydrochlorides were employed as reference comparisons for the dissolution of the corresponding organic acid addition salt of the drug. Reference standards are available from the United States Pharmacopeia; imipramine hydrochloride employed as reference standard was used "as is" and was available from Sigma-Aldrich Catalog #10899. Proceeding, 30-45 mg of the drug hydrochloride reference standard was accurately weighed into a 100 mL volumetric flask and diluted to volume with a previously prepared sample diluent consisting of a filtered 8:2 water:acetonitrile solution. Samples of the dissolution trial solutions were obtained at timed intervals and diluted prior to analysis to obtain targeted concentrations of approximately 45 micro grams/mL-75 micro grams/mL of active pharmaceutical ingredient (API). The prepared samples were then filtered through a 0.45 micron filter directly into an HPLC vial, labeled and loaded for injection into the HPLC system.

HPLC data collection was performed and concentrations determined for each dissolution time interval for each drug substance tested. Concentration assays were determined as a weight/weight percent based on the assay obtained from the reference standard. The data was plotted as a function of percent API salt released versus the sampling interval time wherein the percent API salt released corresponds to a mass assay of the active species found by HPLC analysis of each dissolution time point divided by the available mass initially delivered to the test solution in the capsule.

The present invention has been described with particular reference to the preferred embodiments without limit thereto. It would be apparent to one of skill in the art that additional embodiments, modifications and alterations are available without departure from the scope of the invention which is more specifically set forth in the claims appended hereto.

The invention claimed is:

1. A pharmaceutical drug product comprising at least one drug substance selected from the group consisting of:
   amorphous sibutramine pamoate characterized by at least one method selected from:
      a PXRD diffractogram of FIG. 1;
      a DSC thermogram of FIG. 5; and
      an FTIR spectrum of FIG. 3;
   polymorphic sibutramine pamoate characterized by at least one method selected from:
      a PXRD diffractogram of FIG. 2;
      a DSC thermogram of FIG. 6; and
      an FTIR spectrum of FIG. 4;
   amorphous nortriptyline pamoate characterized by at least one method selected from:
      a DSC thermogram of FIG. 9; and
      an FTIR spectrum of FIG. 11;
   polymorphic nortriptyline pamoate characterized by at least one method selected from:
      a DSC thermogram of FIG. 10; and
      an FTIR spectrum of FIG. 12;
   amorphous clomipramine pamoate characterized by at least one method selected from:
      a PXRD diffractogram of FIG. 16;
      a DSC thermogram of FIG. 20; and
      an FTIR spectrum of FIG. 18;
   polymorphic clomipramine pamoate characterized by at least one method selected from:
      a PXRD diffractogram of FIG. 17;
      a DSC thermogram of FIG. 21; and
      an FTIR of FIG. 19;
   amorphous promethazine pamoate characterized by at least one method selected from:
      a PXRD diffractogram of FIG. 26;
      a DSC thermogram of FIG. 32;
      an FTIR spectrum of FIG. 29;
      a PXRD diffractogram of FIG. 27;
      a DSC thermogram of FIG. 33; and
      an FTIR spectrum of FIG. 30;
   and
   polymorphic promethazine pamoate characterized by at least one method selected from:
      a PXRD diffractogram of FIG. 28;
      a DSC thermogram of FIG. 34; and
      an FTIR spectrum of FIG. 31.

2. The pharmaceutical drug product of claim 1 wherein said drug substance is amorphous sibutramine pamoate characterized by a PXRD diffractogram of FIG. 1.

3. The pharmaceutical drug product of claim 1 wherein said drug substance is amorphous sibutramine pamoate characterized by an FTIR spectrum of FIG. 3.

4. The pharmaceutical drug product of claim 1 wherein said drug substance is amorphous sibutramine pamoate characterized by a DSC thermogram of FIG. 5.

5. The pharmaceutical drug product of claim 1 wherein said drug substance is polymorphic sibutramine pamoate characterized by a PXRD diffractogram of FIG. 2.

6. The pharmaceutical drug product of claim 1 wherein said drug substance is polymorphic sibutramine pamoate characterized by an FTIR spectrum of FIG. 4.

7. The pharmaceutical drug product of claim 1 wherein said drug substance is polymorphic sibutramine pamoate characterized by a DSC thermogram of FIG. 6.

8. The pharmaceutical drug product of claim 1 wherein said drug substance is amorphous nortriptyline pamoate characterized by a DSC thermogram of FIG. 9.

9. The pharmaceutical drug product of claim 1 wherein said drug substance is amorphous nortriptyline pamoate characterized by an FTIR spectrum of FIG. 11.

10. The pharmaceutical drug product of claim 1 wherein said drug substance is polymorphic nortriptyline pamoate characterized by a DSC thermogram of FIG. 10.

11. The pharmaceutical drug product of claim 1 wherein said drug substance is polymorphic nortriptyline pamoate characterized by an FTIR spectrum of FIG. 12.

12. The pharmaceutical drug product of claim 1 wherein said drug substance is amorphous clomipramine pamoate characterized by a PXRD diffractogram of FIG. 16.

13. The pharmaceutical drug product of claim 1 wherein said drug substance is amorphous clomipramine pamoate characterized by an FTIR spectrum of FIG. 18.

14. The pharmaceutical drug product of claim 1 wherein said drug substance is amorphous clomipramine pamoate characterized by a DSC thermogram of FIG. 20.

15. The pharmaceutical drug product of claim 1 wherein said drug substance is polymorphic clomipramine pamoate characterized by a PXRD diffractogram of FIG. 17.

16. The pharmaceutical drug product of claim 1 wherein said drug substance is polymorphic clomipramine pamoate characterized by an FTIR of FIG. 19.

17. The pharmaceutical drug product of claim 1 wherein said drug substance is polymorphic clomipramine pamoate characterized by a DSC thermogram of FIG. 21.

18. The pharmaceutical drug product of claim 1 wherein said drug substance is amorphous promethazine pamoate having a PXRD diffractogram of FIG. 26.

19. The pharmaceutical drug product of claim 1 wherein said drug substance is amorphous promethazine pamoate having a PXRD diffractogram of FIG. 27.

20. The pharmaceutical drug product of claim 1 wherein said drug substance is amorphous promethazine pamoate having an FTIR spectrum of FIG. 29.

21. The pharmaceutical drug product of claim 1 wherein said drug substance is amorphous promethazine pamoate having an FTIR spectrum of FIG. 30.

22. The pharmaceutical drug product of claim 1 wherein said drug substance is amorphous promethazine pamoate having a DSC thermogram of FIG. 32.

23. The pharmaceutical drug product of claim 1 wherein said drug substance is amorphous promethazine pamoate having a DSC thermogram of FIG. 33.

24. The pharmaceutical drug product of claim 1 wherein said drug substance is polymorphic promethazine pamoate having a PXRD diffractogram of FIG. 28.

25. The pharmaceutical drug product of claim 1 wherein said drug substance is polymorphic promethazine pamoate having an FTIR spectrum of FIG. 31.

26. The pharmaceutical drug product of claim 1 wherein said drug substance is polymorphic promethazine pamoate having a DSC thermogram of FIG. 34.

27. A method of administering drug product to a patient comprising:
   providing said drug product to said patient as an oral dose wherein said drug product comprises at least one drug substance selected from the group consisting of:
      amorphous sibutramine pamoate characterized by at least one method selected from:
         a PXRD diffractogram of FIG. 1;
         a DSC thermogram of FIG. 5; and
         an FTIR spectrum of FIG. 3;
      polymorphic sibutramine pamoate characterized by at least one method selected from:
         a PXRD diffractogram of FIG. 2;
         a DSC thermogram of FIG. 6; and
         an FTIR spectrum of FIG. 4;
      amorphous nortriptyline pamoate characterized by at least one method selected from:
         a DSC thermogram of FIG. 9; and
         an FTIR spectrum of FIG. 11;
      polymorphic nortriptyline pamoate characterized by at least one method selected from:
         a DSC thermogram of FIG. 10; and
         an FTIR spectrum of FIG. 12;
      amorphous clomipramine pamoate characterized by at least one method selected from:
         a PXRD diffractogram of FIG. 16;
         a DSC thermogram of FIG. 20; and
         an FTIR spectrum of FIG. 18;
      polymorphic clomipramine pamoate characterized by at least one method selected from:
         a PXRD diffractogram of FIG. 17;
         a DSC thermogram of FIG. 21; and
         an FTIR of FIG. 19;
      amorphous promethazine pamoate characterized by at least one method selected from:
         a PXRD diffractogram of FIG. 26;
         a DSC thermogram of FIG. 32;
         an FTIR spectrum of FIG. 29;
         a PXRD diffractogram of FIG. 27;
         a DSC thermogram of FIG. 33; and
         an FTIR spectrum of FIG. 30;
      and
      polymorphic promethazine pamoate characterized by at least one method selected from:
         a PXRD diffractogram of FIG. 28;
         a DSC thermogram of FIG. 34; and
         an FTIR spectrum of FIG. 3;
   administering said oral dose to a patient wherein no more than 50%, by weight, of active pharmaceutical ingredient of said drug substance releases in a stomach and at least 50%, by weight, of said active pharmaceutical ingredient releases in an intestine.

28. The method of administering drug product to a patient of claim 27 wherein said drug substance is amorphous sibutramine pamoate characterized by a PXRD diffractogram of FIG. 1.

29. The method of administering drug product to a patient of claim 27 wherein said drug substance is amorphous sibutramine pamoate characterized by an FTIR spectrum of FIG. 3.

30. The method of administering drug product to a patient of claim 27 wherein said drug substance is amorphous sibutramine pamoate characterized by a DSC thermogram of FIG. 5.

31. The method of administering drug product to a patient of claim 27 wherein said drug substance is polymorphic sibutramine pamoate characterized by a PXRD diffractogram of FIG. 2.

32. The method of administering drug product to a patient of claim 27 wherein said drug substance is polymorphic sibutramine pamoate characterized by an FTIR spectrum of FIG. 4.

33. The method of administering drug product to a patient of claim 27 wherein said drug substance is polymorphic sibutramine pamoate characterized by a DSC thermogram of FIG. 6.

34. The method of administering drug product to a patient of claim 27 wherein said drug substance is amorphous nortriptyline pamoate characterized by a DSC thermogram of FIG. 9.

35. The method of administering drug product to a patient of claim 27 wherein said drug substance is amorphous nortriptyline pamoate characterized by an FTIR spectrum of FIG. 11.

36. The method of administering drug product to a patient of claim 27 wherein said drug substance is polymorphic nortriptyline pamoate characterized by a DSC thermogram of FIG. 10.

37. The method of administering drug product to a patient of claim 27 wherein said drug substance is polymorphic nortriptyline pamoate characterized by an FTIR spectrum of FIG. 12.

38. The method of administering drug product to a patient of claim 27 wherein said drug substance is amorphous clomipramine pamoate characterized by a PXRD diffractogram of FIG. 16.

39. The method of administering drug product to a patient of claim 27 wherein said drug substance is amorphous clomipramine pamoate characterized by an FTIR spectrum of FIG. 18.

40. The method of administering drug product to a patient of claim 27 wherein said drug substance is amorphous clomipramine pamoate characterized by a DSC thermogram of FIG. 20.

41. The method of administering drug product to a patient of claim 27 wherein said drug substance is polymorphic clomipramine pamoate characterized by a PXRD diffractogram of FIG. 17.

42. The method of administering drug product to a patient of claim 27 wherein said drug substance is polymorphic clomipramine pamoate characterized by an FTIR of FIG. 19.

43. The method of administering drug product to a patient of claim 27 wherein said drug substance is polymorphic clomipramine pamoate characterized by a DSC thermogram of FIG. 21.

44. The method of administering drug product to a patient of claim 27 wherein said drug substance is amorphous promethazine pamoate having a PXRD diffractogram of FIG. 26.

45. The method of administering drug product to a patient of claim 27 wherein said drug substance is amorphous promethazine pamoate having a PXRD diffractogram of FIG. 27.

46. The method of administering drug product to a patient of claim 27 wherein said drug substance is amorphous promethazine pamoate having an FTIR spectrum of FIG. 29.

47. The method of administering drug product to a patient of claim 27 wherein said drug substance is amorphous promethazine pamoate having an FTIR spectrum of FIG. 30.

48. The method of administering drug product to a patient of claim 27 wherein said drug substance is amorphous promethazine pamoate having a DSC thermogram of FIG. 32.

49. The method of administering drug product to a patient of claim 27 wherein said drug substance is amorphous promethazine pamoate having a DSC thermogram of FIG. 33.

50. The method of administering drug product to a patient of claim 27 wherein said drug substance is polymorphic promethazine pamoate having a PXRD diffractogram of FIG. 28.

51. The method of administering drug product to a patient of claim 27 wherein said drug substance is polymorphic promethazine pamoate having an FTIR spectrum of FIG. 31.

52. The method of administering drug product to a patient of claim 27 wherein said drug substance is polymorphic promethazine pamoate having a DSC thermogram of FIG. 34.

53. The method of administering drug product to a patient of claim 27 wherein said oral dose does not have an enteric coating.

54. The method of administering drug product to a patient of claim 27 wherein no more than 25%, by weight, of said active pharmaceutical ingredient releases in said stomach.

55. The method of administering drug product to a patient of claim 27 wherein at least 75%, by weight, of an active pharmaceutical ingredient of said drug substance releases in an intestine.

56. The method of administering drug product to a patient of claim 27 further comprising at least one treatment selected from the group consisting of enteric coating, granulation, encapsulation, bead impregnation and polymeric matrix formation.

57. The method of administering drug product to a patient of claim 27 wherein said drug product is an oral dose selected from a group consisting of tablet, capsule, suspension or gel capsule.

58. A method of administering an active pharmaceutical to a patient comprising:
providing a drug product comprising at least one drug substance to said patient wherein said drug substance is selected from the group consisting of:
amorphous sibutramine pamoate characterized by at least one method selected from:
a PXRD diffractogram of FIG. 1;
a DSC thermogram of FIG. 5; and
an FTIR spectrum of FIG. 3;
polymorphic sibutramine pamoate characterized by at least one method selected from:
a PXRD diffractogram of FIG. 2;
a DSC thermogram of FIG. 6; and
an FTIR spectrum of FIG. 4;
amorphous nortriptyline pamoate characterized by at least one method selected from:
a DSC thermogram of FIG. 9; and
an FTIR spectrum of FIG. 11;
polymorphic nortriptyline pamoate characterized by at least one method selected from:
a DSC thermogram of FIG. 10; and
an FTIR spectrum of FIG. 12;
amorphous clomipramine pamoate characterized by at least one method selected from:
a PXRD diffractogram of FIG. 16;
a DSC thermogram of FIG. 20; and
an FTIR spectrum of FIG. 18;
polymorphic clomipramine pamoate characterized by at least one method selected from:
a PXRD diffractogram of FIG. 17;
a DSC thermogram of FIG. 21; and
an FTIR of FIG. 19;
amorphous promethazine pamoate characterized by at least one method selected from:
a PXRD diffractogram of FIG. 26;
a DSC thermogram of FIG. 32;
an FTIR spectrum of FIG. 29;
a PXRD diffractogram of FIG. 27;
a DSC thermogram of FIG. 33; and
an FTIR spectrum of FIG. 30;
and
polymorphic promethazine pamoate characterized by at least one method selected from:
a PXRD diffractogram of FIG. 28;
a DSC thermogram of FIG. 34; and
an FTIR spectrum of FIG. 31;
introducing said drug substance to a first drug absorption location of said patient wherein a portion of said active pharmaceutical in said drug substance is released from said drug substance yielding a released active pharmaceutical and a modified drug substance comprising a second ratio of said active pharmaceutical to said organic counterion of less than 2:1;
introducing said modified drug substance to a second drug absorption location of said patient wherein a remainder of said active pharmaceutical is released yielding an active ingredient and a free organic counterion.

59. The method of administering drug product to a patient of claim 58 wherein said drug substance is amorphous sibutramine pamoate characterized by a PXRD diffractogram of FIG. 1.

60. The method of administering drug product to a patient of claim 58 wherein said drug substance is amorphous sibutramine pamoate characterized by an FTIR spectrum of FIG. 3.

61. The method of administering drug product to a patient of claim 58 wherein said drug substance is amorphous sibutramine pamoate characterized by a DSC thermogram of FIG. 5.

62. The method of administering drug product to a patient of claim 58 wherein said drug substance is polymorphic sibutramine pamoate characterized by a PXRD diffractogram of FIG. 2.

63. The method of administering drug product to a patient of claim 58 wherein said drug substance is polymorphic sibutramine pamoate characterized by an FTIR spectrum of FIG. 4.

64. The method of administering drug product to a patient of claim 58 wherein said drug substance is polymorphic sibutramine pamoate characterized by a DSC thermogram of FIG. 6.

65. The method of administering drug product to a patient of claim 58 wherein said drug substance is amorphous nortriptyline pamoate characterized by a DSC thermogram of FIG. 9.

66. The method of administering drug product to a patient of claim 58 wherein said drug substance is amorphous nortriptyline pamoate characterized by an FTIR spectrum of FIG. 11.

67. The method of administering drug product to a patient of claim 58 wherein said drug substance is polymorphic nortriptyline pamoate characterized by a DSC thermogram of FIG. 10.

68. The method of administering drug product to a patient of claim 58 wherein said drug substance is polymorphic nortriptyline pamoate characterized by an FTIR spectrum of FIG. 12.

69. The method of administering drug product to a patient of claim 58 wherein said drug substance is amorphous clomipramine pamoate characterized by a PXRD diffractogram of FIG. 16.

70. The method of administering drug product to a patient of claim 58 wherein said drug substance is amorphous clomipramine pamoate characterized by an FTIR spectrum of FIG. 18.

71. The method of administering drug product to a patient of claim 58 wherein said drug substance is amorphous clomipramine pamoate characterized by a DSC thermogram of FIG. 20.

72. The method of administering drug product to a patient of claim 58 wherein said drug substance is polymorphic clomipramine pamoate characterized by a PXRD diffractogram of FIG. 17.

73. The method of administering drug product to a patient of claim 58 wherein said drug substance is polymorphic clomipramine pamoate characterized by an FTIR of FIG. 19.

74. The method of administering drug product to a patient of claim 58 wherein said drug substance is polymorphic clomipramine pamoate characterized by a DSC thermogram of FIG. 21.

75. The method of administering drug product to a patient of claim 58 wherein said drug substance amorphous promethazine pamoate having a PXRD diffractogram of FIG. 26.

76. The method of administering drug product to a patient of claim 58 wherein said drug substance is amorphous promethazine pamoate having a PXRD diffractogram of FIG. 27.

77. The method of administering drug product to a patient of claim 58 wherein said drug substance is amorphous promethazine pamoate having an FTIR spectrum of FIG. 29.

78. The method of administering drug product to a patient of claim 58 wherein said drug substance is amorphous promethazine pamoate having an FTIR spectrum of FIG. 30.

79. The method of administering drug product to a patient of claim 58 wherein said drug substance is amorphous promethazine pamoate having a DSC thermogram of FIG. 32.

80. The method of administering drug product to a patient of claim 58 wherein said drug substance is amorphous promethazine pamoate having a DSC thermogram of FIG. 33.

81. The method of administering drug product to a patient of claim 58 wherein said drug substance is polymorphic promethazine pamoate having a PXRD diffractogram of FIG. 28.

82. The method of administering drug product to a patient of claim 58 wherein said drug substance is polymorphic promethazine pamoate having an FTIR spectrum of FIG. 31.

83. The method of administering drug product to a patient of claim 58 wherein said drug substance is polymorphic promethazine pamoate having a DSC thermogram of FIG. 34.

84. The method of administering drug product to a patient of claim 25 wherein said first drug absorption location and said second drug absorption location are independently selected from mucosal membranes, stomach and intestine.

85. The method of administering drug product to a patient of claim 84 wherein said first drug absorption location is said stomach.

86. The method of administering drug product to a patient of claim 84 wherein said second drug absorption location is said intestine.

87. The method of administering drug product to a patient of claim 58 wherein said active pharmaceutical is provided in an oral dose and said oral dose does not have an enteric coating.

88. The method of administering drug product to a patient of claim 58 wherein said second ratio is at least 1:1.

89. The method of administering drug product to a patient of claim 58 wherein said second ratio no more than 1:1.

90. The method of administering drug product to a patient of claim 58 wherein said active pharmaceutical ingredient exhibits anti-convulsant, anti-depressant, analgesic, anesthetic, anxiolytic, psychotropic, hallucinogenic, hypnotic, anorexic, cough remedy, cold remedy, sinus remedy, irritable bowel syndrome treatment, urinary incontinence, anti-neoplastic, anti-emetic, anti-biotic or adjuvant therapy.

91. The method of administering drug product to a patient of claim 58 wherein no more than 25%, by weight, of an active pharmaceutical ingredient of said drug substance releases in said stomach.

92. The method of administering drug product to a patient of claim 58 wherein at least 75%, by weight, of an active pharmaceutical ingredient of said drug substance releases in an intestine.

93. The method of administering drug product to a patient of claim 58 wherein said drug product further comprises a second drug substance comprising a second active pharmaceutical ingredient and a second organic counterion.

94. The method of administering drug product to a patient of claim 93 wherein said drug substance comprises an active pharmaceutical ingredient and wherein said active pharmaceutical ingredient and said second active pharmaceutical ingredient are the same.

95. The method of administering drug product to a patient of claim 93 wherein said drug substance comprises an organic counterion and wherein said organic counterion and said second organic counterion are the same.

96. The method of administering drug product to a patient of claim 93 wherein each of said drug substance and said second drug substance is selected from an amorphous drug substance and a morphological drug substance.

97. The method of administering drug product to a patient of claim 96 wherein said morphological drug substance has a stoichiometric ratio of said active pharmaceutical ingredient to said second organic counterion selected from 2:1 and 1:1.

98. The method of administering drug product to a patient of claim 96 comprising a predetermined ratio of said amorphous drug substance and said morphological drug substance wherein said predetermined ratio defines a dissolution profile of said pharmaceutical drug substance.

99. The method of administering drug product to a patient of claim 96 wherein said amorphous drug substance and said morphological drug substance have different dissolution rates.

100. The method of administering drug product to a patient of claim 99 wherein said morphological drug substance has a phase transition of at least 75 J/g.

101. The method of administering drug product to a patient of claim 100 wherein said amorphous drug substance has a faster dissolution rate than said morphological drug substance.

102. The method of administering drug product to a patient of claim 99 wherein said amorphous drug substance has a slower dissolution rate than said morphological drug substance.

103. The method of administering drug product to a patient of claim 96 wherein at least one of said amorphous drug substance and said morphological drug substance exhibits immediate release and is immediately available at a therapeutic concentration when administered to a patient and wherein the other at least one of said amorphous drug substance and said morphological drug substance becomes available as a function of time.

104. The method of administering an drug product to a patient of claim 58 wherein said drug product further comprises at least one treatment selected from the group consisting of enteric coating, granulation, encapsulation, bead impregnation and polymeric matrix formation.

105. The method of administering drug product to a patient of claim 58 wherein said drug product is an oral dose selected from a group consisting of tablet, capsule, suspension or gel capsule.

106. A pharmaceutical drug product comprising:
an amorphous drug substance selected from the group consisting of:
amorphous sibutramine pamoate characterized by at least one method selected from:
a PXRD diffractogram of FIG. 1;
a DSC thermogram of FIG. 5; and
an FTIR spectrum of FIG. 3;
amorphous nortriptyline pamoate characterized by at least one method selected from:
a DSC thermogram of FIG. 9; and
an FTIR spectrum of FIG. 11;
amorphous clomipramine pamoate characterized by at least one method selected from:
a PXRD diffractogram of FIG. 16;
a DSC thermogram of FIG. 20; and
an FTIR spectrum of FIG. 18; and
amorphous promethazine pamoate characterized by at least one method selected from:
a PXRD diffractogram of FIG. 26;
a DSC thermogram of FIG. 32;
an FTIR spectrum of FIG. 29;
a PXRD diffractogram of FIG. 27;
a DSC thermogram of FIG. 33; and
an FTIR spectrum of FIG. 30;
and
a morphological drug substance comprising an active pharmaceutical ingredient and an organic counterion;
wherein said organic counterion is defined by:

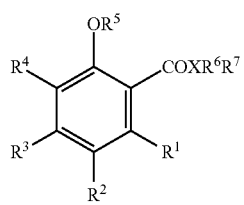

Structure A

Structure A
wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6$+$R^7$ may represent an alkali earth cation, ammonium or together form a heterocyclic moiety.

107. The pharmaceutical drug product of claim 106 wherein said amorphous drug substance is amorphous sibutramine pamoate characterized by a PXRD diffractogram of FIG. 1.

108. The pharmaceutical drug product of claim 106 wherein said drug substance is amorphous sibutramine pamoate characterized by an FTIR spectrum of FIG. 3.

109. The pharmaceutical drug product of claim 106 wherein said drug substance is amorphous sibutramine pamoate characterized by a DSC thermogram of FIG. 5.

110. The pharmaceutical drug product of claim 106 wherein said amorphous drug substance is amorphous nortriptyline pamoate characterized by a DSC thermogram of FIG. 9.

111. The pharmaceutical drug product of claim 106 wherein said drug substance is amorphous nortriptyline pamoate characterized by an FTIR spectrum of FIG. 11.

112. The pharmaceutical drug product of claim 106 wherein said amorphous drug substance is amorphous clomipramine pamoate characterized by a PXRD diffractogram of FIG. 16.

113. The pharmaceutical drug product of claim 106 wherein said drug substance is amorphous clomipramine pamoate characterized by an FTIR spectrum of FIG. 18.

114. The pharmaceutical drug product of claim 106 wherein said drug substance is amorphous clomipramine pamoate characterized by a DSC thermogram of FIG. 20.

115. The pharmaceutical drug product of claim 106 wherein said amorphous drug substance is amorphous promethazine pamoate having a PXRD diffractogram of FIG. 26.

116. The pharmaceutical drug product of claim 106 wherein said amorphous drug substance is amorphous promethazine pamoate having a PXRD diffractogram of FIG. 27.

117. The pharmaceutical drug product of claim 106 wherein said drug substance is amorphous promethazine pamoate having an FTIR spectrum of FIG. 29.

118. The pharmaceutical drug product of claim 106 wherein said drug substance is amorphous promethazine pamoate having an FTIR spectrum of FIG. 30.

119. The pharmaceutical drug product of claim 106 wherein said drug substance is amorphous promethazine pamoate having a DSC thermogram of FIG. 32.

120. The pharmaceutical drug product of claim 106 wherein said drug substance is amorphous promethazine pamoate having a DSC thermogram of FIG. 33.

121. The pharmaceutical drug product of claim 106 wherein said drug product does not contain an enteric coating.

122. The pharmaceutical drug product of claim 106 wherein at least one of said organic counterion is defined by

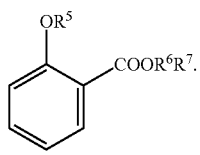

Structure B

123. The pharmaceutical drug product of claim 106 wherein said organic counterion is defined by

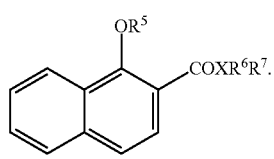

Structure C

124. The pharmaceutical drug product of claim 106 wherein said organic counterion is defined by

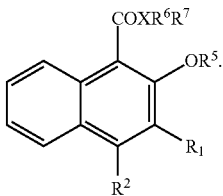

Structure D

125. The pharmaceutical drug product of claim 106 wherein said organic counterion is defined by

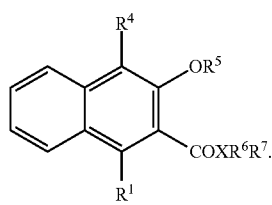

Structure E

126. The pharmaceutical drug product of claim 106 wherein said organic counterion is defined by

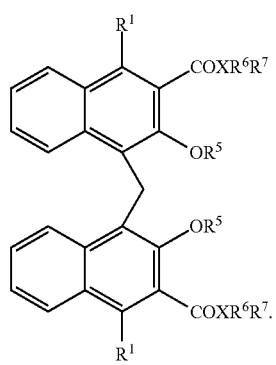

Structure F

127. The pharmaceutical drug product of claim 106 wherein said organic counterion is defined by

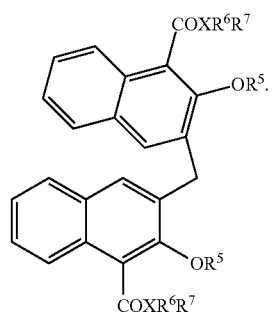

Structure G

128. The pharmaceutical drug product of claim 106 wherein said organic counterion is selected from a group consisting of salicylic acid, 1,2-hydroxynaphthoic acid, 2,3-hydroxynapthoic acid, pamoic acid and their synthetic equivalents.

129. A pharmaceutical drug product comprising:
an amorphous drug substance comprising an active pharmaceutical ingredient and a organic counterion; and
a morphological drug substance selected from the group consisting of:
polymorphic sibutramine pamoate characterized by at least one method selected from:
a PXRD diffractogram of FIG. 2;
a DSC thermogram of FIG. 6; and
an FTIR spectrum of FIG. 4;
polymorphic nortriptyline pamoate characterized by at least one method selected from:
a DSC thermogram of FIG. 10; and
an FTIR spectrum of FIG. 12;
polymorphic clomipramine pamoate characterized by at least one method selected from:
a PXRD diffractogram of FIG. 17;
a DSC thermogram of FIG. 21; and
an FTIR of FIG. 19;
and
polymorphic promethazine pamoate characterized by at least one method selected from:
a PXRD diffractogram of FIG. 28;
a DSC thermogram of FIG. 34; and
an FTIR spectrum of FIG. 3;
wherein said organic counterion is defined by Structure A

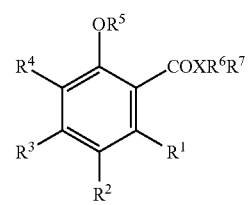

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6$+$R^7$ may represent an alkali earth cation, ammonium or together form a heterocyclic moiety.

130. The pharmaceutical drug product of claim 129 wherein said morphological drug substance is polymorphic sibutramine pamoate characterized by a PXRD diffractogram of FIG. 2.

131. The pharmaceutical drug product of claim 129 wherein said drug substance is polymorphic sibutramine pamoate characterized by an FTIR spectrum of FIG. 4.

132. The pharmaceutical drug product of claim 129 wherein said drug substance is polymorphic sibutramine pamoate characterized by a DSC thermogram of FIG. 6.

133. The pharmaceutical drug product of claim 129 wherein said morphological drug substance is polymorphic nortriptyline pamoate characterized by a DSC thermogram of FIG. 10.

134. The pharmaceutical drug product of claim 129 wherein said drug substance is polymorphic nortriptyline pamoate characterized by an FTIR spectrum of FIG. 12.

135. The pharmaceutical drug product of claim 129 wherein said morphological drug substance is polymorphic clomipramine pamoate characterized by a PXRD diffractogram of FIG. 17.

136. The pharmaceutical drug product of claim 129 wherein said drug substance is polymorphic clomipramine pamoate characterized by an FTIR of FIG. 19.

137. The pharmaceutical drug product of claim 129 wherein said drug substance is polymorphic clomipramine pamoate characterized by a DSC thermogram of FIG. 21.

138. The pharmaceutical drug product of claim 129 wherein said drug substance is polymorphic promethazine pamoate having a PXRD diffractogram of FIG. 28.

139. The pharmaceutical drug product of claim 129 wherein said drug substance is polymorphic promethazine pamoate having an FTIR spectrum of FIG. 31.

140. The pharmaceutical drug product of claim 129 wherein said drug substance is polymorphic promethazine pamoate having a DSC thermogram of FIG. 34.

141. The pharmaceutical drug product of claim 129 wherein said drug product does not contain an enteric coating.

142. The pharmaceutical drug product of claim 129 wherein said organic counterion is defined by

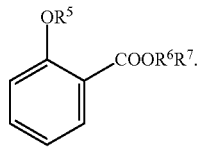

Structure B

143. The pharmaceutical drug product of claim 129 wherein said organic counterion is defined by

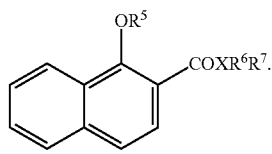

Structure C

144. The pharmaceutical drug product of claim 129 wherein at said organic counterion is defined by

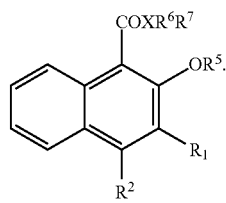

Structure D

145. The pharmaceutical drug product of claim 129 wherein said organic counterion is defined by

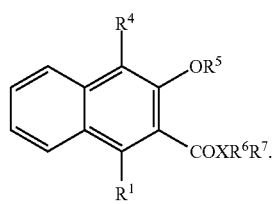

Structure E

146. The pharmaceutical drug product of claim 129 wherein said organic counterion is defined by

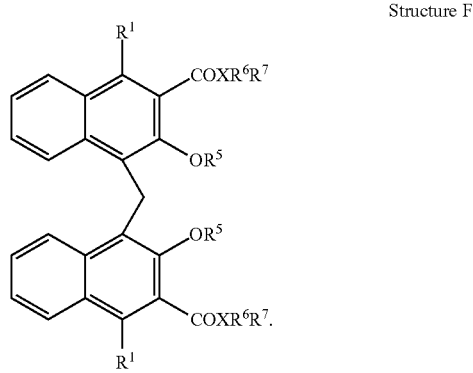

Structure F

147. The pharmaceutical drug product of claim 129 wherein said organic counterion is defined by

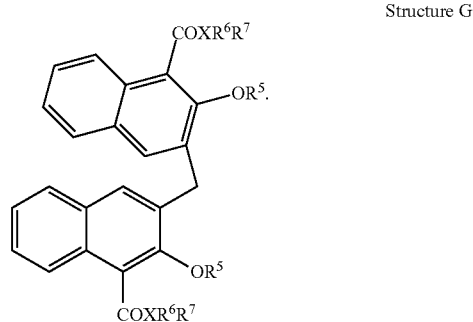

Structure G

148. The pharmaceutical drug product of claim 129 wherein said organic counterion is selected from a group consisting of salicylic acid, 1,2-hydroxynaphthoic acid, 2,3-hydroxynapthoic acid, pamoic acid and their synthetic equivalents.

149. The pharmaceutical drug product of claim 129 wherein said drug product is an oral dose selected from a group consisting of tablet, capsule, suspension or gel capsule.

* * * * *

UNITED STATES PATENT AND TRADEMARK OFFICE
CERTIFICATE OF CORRECTION

PATENT NO. : 8,883,863 B1  
APPLICATION NO. : 13/723323  
DATED : November 11, 2014  
INVENTOR(S) : King et al.

Page 1 of 1

It is certified that error appears in the above-identified patent and that said Letters Patent is hereby corrected as shown below:

On the Title Page, item (54), and in the Specification, Column 1, lines 1-2, the title of the invention should read as follows:

DRUG RELEASE PROPERTIES OF POLYMORPHIC PHARMACEUTICAL SUBSTANCES

On the Title Page, item (72), the inventors should be listed as follows:

Clifford Riley King, Hendersonville, NC (US); Joseph Pike Mitchner, Flat Rock, NC (US); David William Bristol, Mills River, NC (US); Vicki Haynes Audia, Mills River, NC (US).

Signed and Sealed this  
Twenty-fourth Day of February, 2015

Michelle K. Lee  
*Deputy Director of the United States Patent and Trademark Office*